United States Patent
Kingsman et al.

US007259015B2

(10) Patent No.: US 7,259,015 B2
(45) Date of Patent: Aug. 21, 2007

(54) VECTOR SYSTEM

(75) Inventors: Alan John Kingsman, The Oxford Science Park (GB); Nicholas D. Mazarakis, The Oxford Science Park (GB); Enca Martin-Rendon, Sanford-on-Thames (GB); Mimoun Azzouz, The Oxford Science Park (GB); Jonathan Rohll, The Oxford Science Park (GB)

(73) Assignee: Oxford Biomedia (UK) Limited, Oxford (GB)

( * ) Notice: Subject to any disclaimer, the term of this patent is extended or adjusted under 35 U.S.C. 154(b) by 631 days.

(21) Appl. No.: 10/408,456

(22) Filed: Apr. 7, 2003

(65) Prior Publication Data

US 2004/0013648 A1 Jan. 22, 2004

Related U.S. Application Data

(63) Continuation-in-part of application No. PCT/GB01/04433, filed on Oct. 5, 2001.

(30) Foreign Application Priority Data

Oct. 6, 2000 (GB) .................................. 0024550.6

(51) Int. Cl.
*C12N 15/867* (2006.01)
*C12N 15/63* (2006.01)
*C12N 15/64* (2006.01)
*C12N 5/10* (2006.01)
*A61K 48/00* (2006.01)

(52) U.S. Cl. .................. 435/456; 435/320.1; 435/325; 435/366; 435/455

(58) Field of Classification Search ..................... None
See application file for complete search history.

(56) References Cited

U.S. PATENT DOCUMENTS

| | | | |
|---|---|---|---|
| 6,103,226 A | 8/2000 | Kang et al. | |
| 6,506,378 B1 * | 1/2003 | Kang | 424/93.21 |
| 6,555,342 B1 * | 4/2003 | Kappes et al. | 435/69.1 |
| 6,958,226 B1 * | 10/2005 | Gray et al. | 435/91.4 |

FOREIGN PATENT DOCUMENTS

| | | |
|---|---|---|
| WO | WO93/03143 | 2/1993 |
| WO | WO94/24870 | 11/1994 |
| WO | WO97/18319 | 5/1997 |
| WO | WO98/12338 | 3/1998 |

OTHER PUBLICATIONS

Stripecke et al., Blood, Aug. 15, 2000, vol. 96, No. 4, pp. 1317-1326.*
Olsen, Gene Therapy, 1998, vol. 5, pp. 1481-1487.*
Mitrophanous et al., Gene Therapy, 1999, vol. 6, pp. 1808-1818.*
Aran et al., PNAS, 1994, vol. 91, pp. 3176-3180.*
Horvath et al., PNAS, Feb. 15, 2000, vol. 97, No. 4, pp. 1914-1919.*
Moffat et al., "L-Dopa and Dopamine-Producing Gene Cassettes for Gene Therapy Approaches to Parkinson's Disease", Experimental Neurology, vol. 11, No. 1, pp. 69-73, Mar. 1, 1997.
Robbins, et al., "Viral Vectors for Gene Therapy", Trends in Biotechnology, Elsevier Publications, Cambridge, GB, vol. 16, No. 1, pp. 35-40, 1998.
Hsieh et al., "Improved Gene Expression by a Modified Bicistronic Retroviral Vector", Biochemical and Biophysical Research Communications, vol. 214, pp. 910-917, 1995.
During et al., "In Vivo Expression of Therapeutic Human Genes for Dopamine Production in the Caudates of MPTP-Treated Monkeys Using an AAV Vector", Gene Therapy, vol. 5, pp. 820-827, 1998.
Metz et al., "Construction and Characterization of Single-Transcript Tricistronic Retroviral Vectors Using Two Internal Ribosome Entry Sites", Somatic Cell and Molecular Genetics, vol. 24, No. 1, pp. 53-69, 1998.
Nam-Hee Shin, et al., Replication of Lengthened Maloney Marine Leukemia Virus Genomes Is Impaired at Multiple Stages, Journal of Virology, 2000, vol. 74, No. 6, p. 2694-2702.
Didier Trono, HIV-based Vectors: Getting the Best Out Of The Worst, J Gene Med, 2000, vol. 2, p. 61-63.

\* cited by examiner

*Primary Examiner*—David Guzo
(74) *Attorney, Agent, or Firm*—Frommer Lawrence & Haug LLP; Thomas J. Kowalski; Anne-Marie C. Yvon

(57) ABSTRACT

Provided are retroviral vector genomes and vector systems comprising the genomes. In particular, a retroviral vector genome comprising two or more NOIs, operably linked by one or more Internal Ribosome Entry Site(s); a lentiviral vector genome comprising two or more NOIs suitable for treating a neurodegenerative disorder; and a lentiviral vector genome which encodes tyrosine hydroxylase, GTP-cyclohydrolase I and, optionally, Aromatic Amino Acid Dopa Decarboxylase are provided.

52 Claims, 35 Drawing Sheets

Figure 1

5'hTH2

Figure 2:
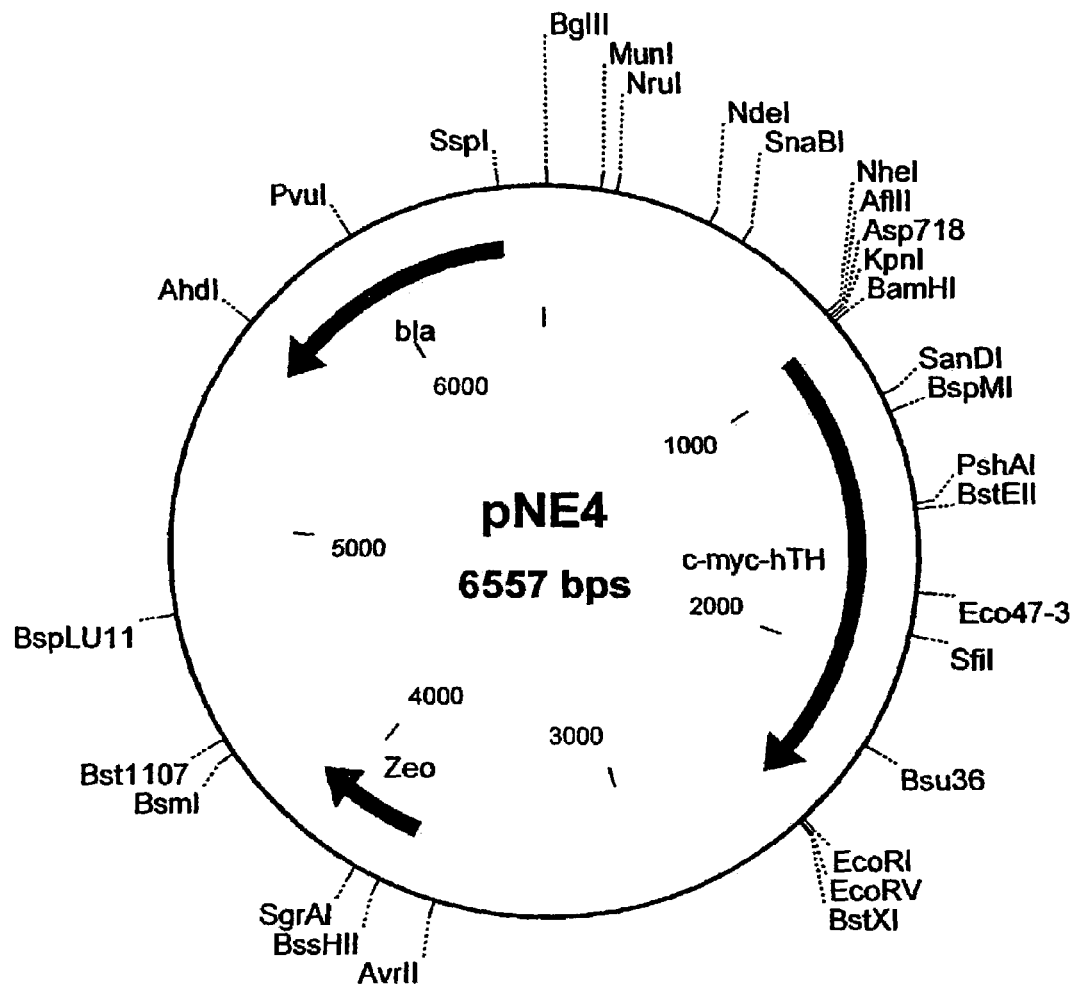

5'-GC GGATCC GCC ACC ATG GAA AAA CTC ATC TCA GAA GAG GAT
      BamH I

CTG CCC ACCCCC GAC GCC ACC ACG –3' (SEQ ID NO: 8)

3'hTH2

5'- GAA CCG CGG GGA CTG CCC TCT TAC C- 3' (SEQ ID NO: 9)

5'hTH3

5'-GGT AAA GAG GGC AGT CCC CGC GGT TC- 3' (SEQ ID NO: 10)

3'-hTH1

5'- CG AAGCTT CTA GCC AATGGC ACT CAG CGC ATG GGC-3' (SEQ ID NO: 11)
      HindIII

Figure 3

5'hAADC

5'- CG <u>AGA TCT</u> *GCC ACC* ATG TAC CCC TAC GAC GTG CCC GAC TAC
       Bgl II

GCC AAC GCA AGT GAA TTC CGA AGG-3' (SEQ ID NO: 12)

3'hAADC

5'- CG <u>AAG CTT</u> CTA CTC CCT CTC TGC TCG C-3' (SEQ ID NO: 13)
      HindIII

Figure 5

5'hGTP

5'- CG <u>AGA TCT</u> *GCC ACC* ATG GAC TAC AAG GAC GAC GAT GAC GAG
      Bgl II

AAG GGC CCT GTG CGG CG-3' (SEQ ID NO: 14)

3'hGTP

5'- CG <u>AAG CTT</u> TCA GCT CCT AAT GAG AGT CAG GAA-3' (SEQ ID NO: 15)
      HindIII

Figure 7

5'hTHt

5'-CG <u>AAG CTT</u> <u>GGA TCC</u> *GCC ACC* ATG GAA CAA AAA CTC ATC TCA
      HindIII    BamHI

GAA GAG GAT CTG AAG GTC CCC TGG TTC CCA AGA AAA-3' (SEQ ID NO: 16)

3'hTHt

5'- CG <u>GAA TTC</u> CTA GCC AAT GGC ACT CAG CGC ATG GGC-3' (SEQ ID NO: 17)
     EcoRI

Comparison of Lentiviral preps by PERT/RNA ratio

Rat 24
7 days post

Figure 24.A

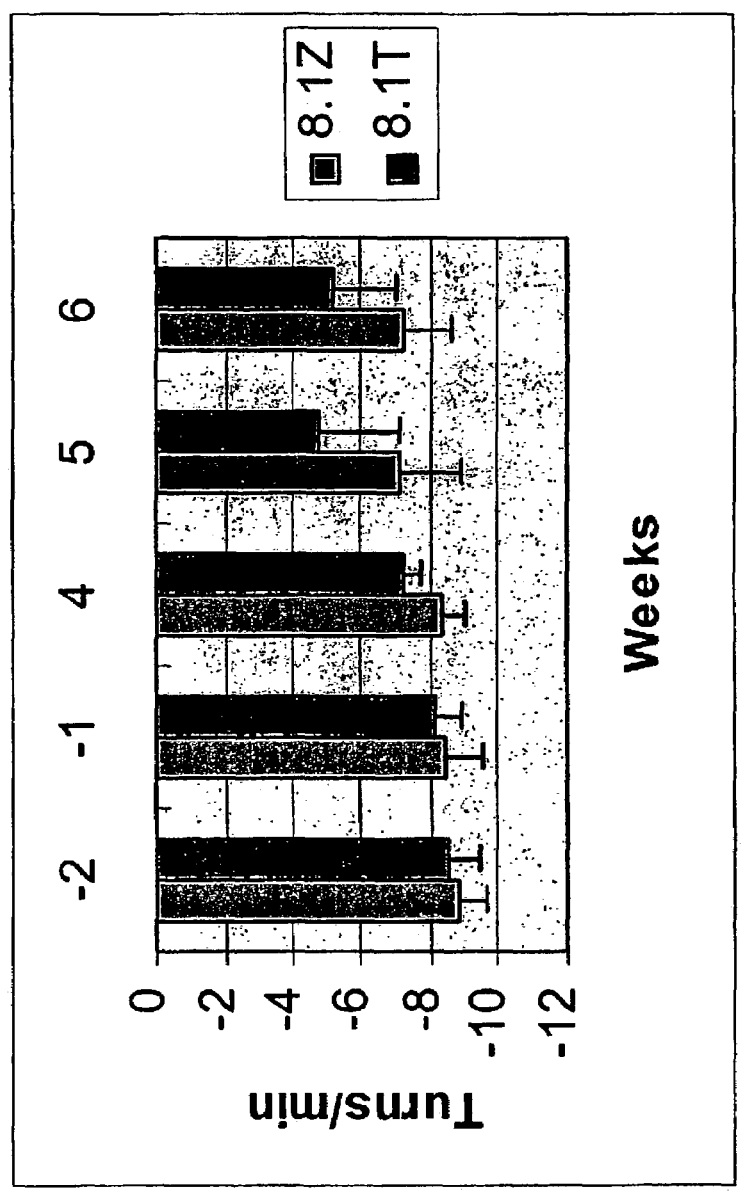
Figure 24.B

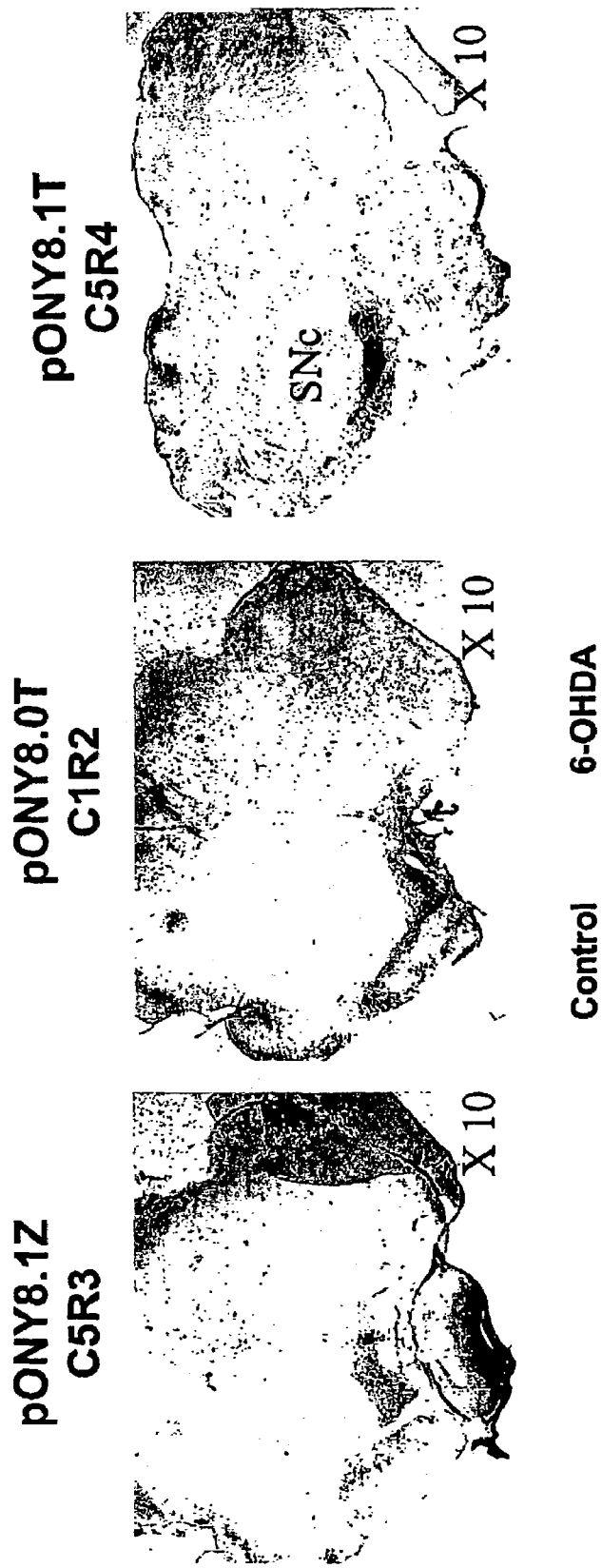
Figure 25.A

Figure 25.B
pONY8.1Z
C3R4
pONY8.1T
C3R5
X 10
pONY8.0T
C5R5
Control
6-OHDA

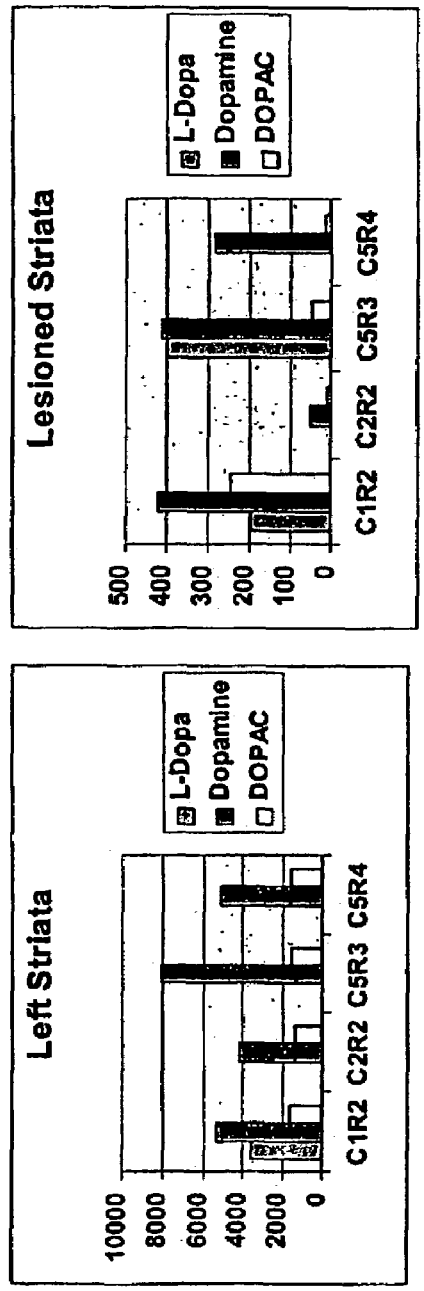
Figure 26: Catecholamines (pg/mg wet tissue)

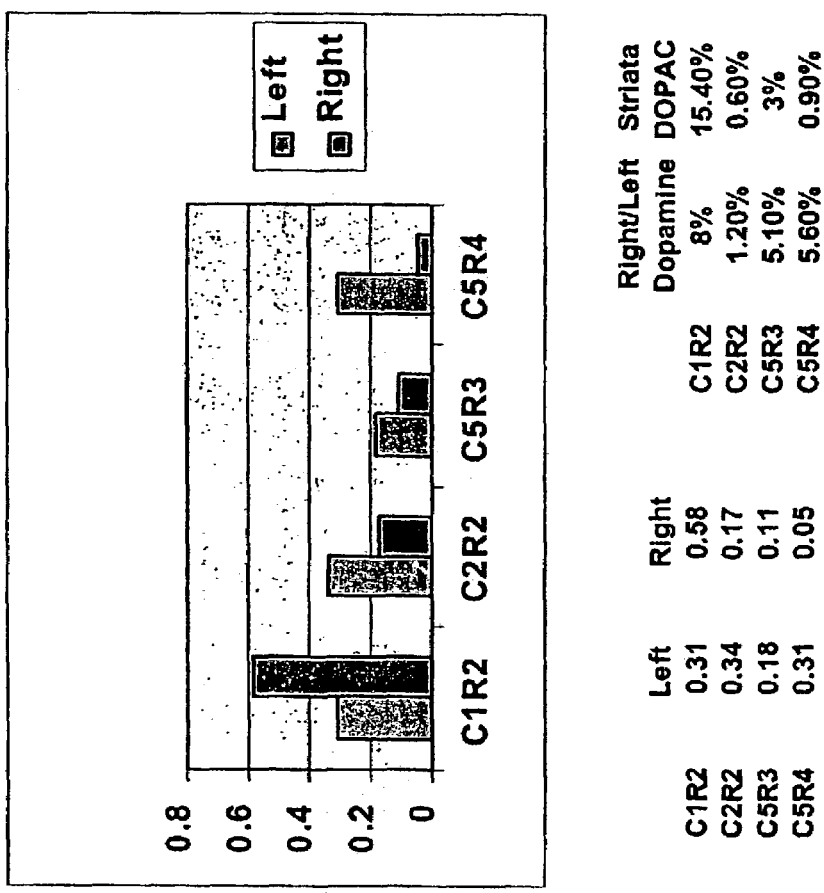
Figure 27: DOPAC/Dopamine ratio

Figure 28

Fig. 28A. Amino acid sequence of codon-optimized GTP-cyclohydrolase I (SEQ ID NO:18)

```
  1 MEKGPVRAPA EKPRGARCSN GFPERDPPRP GPSRPAEKPP RPEAKSAQPA
 51 DGWKGERPRS EEDNELNLPN LAAAYSSILS SLGENPQRQG LLKTPWRAAS
101 AMQFFTKGYQ ETISDVLNDA IFDEDHDEMV IVKDIDMFSM CEHHLVPFVG
151 KVHIGYLPNK QVLGLSKLAR IVEIYSRRLQ VQERLTKQIA VAITEALRPA
201 GVGVVVEATH MCMVMRGVQK MNSKTVTSTM LGVFREDPKT REEFLTLIRS
```

Fig. 28B. Nucleotide sequence of codon-optimized GTP-cyclohydrolase I (SEQ ID NO:19)

atggagaagggccctgtgcgcgccccggccgagaagccgcgcggcgcccgctgcagcaatgggttccccgagcgcgacc
cgccgcgccccgggcccagcaggccggccgagaagccccgcgccccgaggccaagagcgcgcagcccgcggacgg
ctggaagggcgagcgccccgcagcgaggaggacaacgagctgaacctccctaacctggccgccgcctactcctccatcct
gagctcgctgggcgagaaccccagcggcaggggctgctcaagaccccctggagggcggcctcggccatgcagttcttcac
caagggctaccaggagaccatctcagacgtcctgaacgacgctatcttcgacgaagatcacgatgagatggtgatcgtgaag
gacatagacatgttctccatgtgcgagcaccacctggtgccatttgtgggaaaggtccatatcggctacctgcctaacaagcag
gtcctgggcctcagcaagctggcgaggattgtggaaatctatagtagaagactacaggttcaggagcgccttaccaaacaaat
tgctgtggcaatcacggaagccttgcggcctgctggagtcgggtcgtggtggaagcaacacacatgtgtatggtgatgcgag
gtgtacagaaaatgaacagcaaaaccgtgaccagcacaatgctgggtgtgttccgggaggatccaaagactcgggaagag
ttcctgactctcatcaggagctga

Fig. 28C. Amino acid sequence of wild type GTP-cyclohydrolase I (SEQ ID NO:20)

```
  1 MEKGPVRAPA EKPRGARCSN GFPERDPPRP GPSRPAEKPP RPEAKSAQPA
 51 DGWKGERPRS EEDNELNLPN LAAAYSSILS SLGENPQRQG LLKTPWRAAS
101 AMQFFTKGYQ ETISDVLNDA IFDEDHDEMV IVKDIDMFSM CEHHLVPFVG
151 KVHIGYLPNK QVLGLSKLAR IVEIYSRRLQ VQERLTKQIA VAITEALRPA
201 GVGVVVEATH MCMVMRGVQK MNSKTVTSTM LGVFREDPKT REEFLTLIRS
```

Fig. 28D. Nucleotide sequence of wild type GTP-cyclohydrolase I (SEQ ID NO:21)

atggagaagggccctgtgcgggcaccggcggagaagccgcggggcgccaggtgcagcaatgggttccccgagcgggatc
cgccgcggccccgggcccagcaggccggcggagaagccccgcggcccgaggccaagagcgcgcagcccgcggacgg
ctggaagggcgagcggccccgcagcgaggaggataacgagctgaacctccctaacctggcagccgcctactcgtccatcct
gagctcgctgggcgagaaccccagcggcaagggctgctcaagacgccctggagggcggcctcggccatgcagttcttcac
caagggctaccaggagaccatctcagatgtcctaaacgatgctatatttgatgaagatcatgatgagatggtgattgtgaagga
catagacatgttttccatgtgtgagcatcacttggttccatttgttggaaaggtccatattggttatcttcctaacaagcaagtccttgg
cctcagcaaacttgcgaggattgtagaaatctatagtagaagactacaagttcaggagcgccttacaaaacaaattgctgtagc
aatcacggaagccttgcggcctgctggagtcggggtagtggttgaagcaacacacatgtgtatggtaatgcgaggtgtacaga
aaatgaacagcaaaactgtgaccagcacaatgttgggtgtgttccgggaggatccaaagactcgggaagagttcctgactctc
attaggagctga

Figure 29

Fig. 29A. Amino acid sequence of codon-optimized truncated tyrosine hydroxylase, type 2, from 8.9.4 MV opti Y (SEQ ID NO:22)

```
  1 MVKVPWFPRK VSELDKCHHL VTKFDPDLDL DHPGFSDQVY RQRRKLIAEI
 51 AFQYRHGDPI PRVEYTAEEI ATWKEVYTTL KGLYATHACG EHLEAFALLE
101 RFSGYREDNI PQLEDVSRFL KERTGFQLRP VAGLLSARDF LASLAFRVFQ
151 CTQYIRHASS PMHSPEPDCC HELLGHVPML ADRTFAQFSQ DIGLASLGAS
201 DEEIEKLSTL YWFTVEFGLC KQNGEVKAYG AGLLSSYGEL LHCLSEEPEI
251 RAFDPEAAAV QPYQDQTYQS VYFVSESFSD AKDKLRSYAS RIQRPFSVKF
301 DPYTLAIDVL DSPQAVRRSL EGVQDELDTL AHALSAIG
```

Fig. 29B. Nucleotide sequence of codon-optimized truncated tyrosine hydroxylase, type 2, from 8.9.4 MV opti Y (SEQ ID NO:23)

atggtgaaggtaccctggttcccaagaaaagtgtcagagctggacaagtgtcatcacctggtcaccaagttcgaccccgacct
ggacttggaccaccccggcttctcggaccaggtgtaccgccagcgcaggaagctgatcgctgagatcgccttccagtacagg
cacggcgacccgatcccccgtgtggagtacaccgccgaggagatcgccacctggaaggaggtctacaccaccctgaaggg
cctctacgccacccacgcctgcggggagcacctggaggcctttgctttgctggagcgcttcagcggctaccgggaagacaac
atcccccagctggaggacgtctcccgcttcctgaaggagcgcacaggcttccagctgcggcccgtggccggcctgctgtccgc
ccgggacttcctggccagcctggccttccgcgtgttccagtgcacccagtatatccgccacgcgtcctcgcccatgcactcccct
gagccggactgctgccacgagctgctggggcacgtgcccatgctggccgaccgcaccttcgcgcagttcagccaggacatc
ggcctggcgtccctgggggccagcgatgaggaaatcgagaagctgtccactctgtactggttcacggtggagttcgggctgtgt
aagcagaacggggaggtgaaggcctatggtgccgggctgctgtcctcctacggggagctcctgcactgcctgtctgaggagc
ctgagatccggccttcgaccctgaggctgcggccgtgcagccctaccaagaccagacgtaccagtcagtctacttcgtgtctg
agagcttcagcgacgccaaggacaagctcaggagctatgccagccgcatccagcgcccttctccgtgaagttcgacccgta
caccctggccatcgacgtgctggacagcccccaggccgtgcggcgctccctggagggtgtccaggatgagctggacacccttt
gcccatgcgctgagcgccatcggc

Fig. 29C. Amino acid sequence of codon-optimized truncated tyrosine hydroxylase, type 2 with serine at position 211 (SEQ ID NO:24)

```
  1 MVKVPWFPRK VSELDKCHHL VTKFDPDLDL DHPGFSDQVY RQRRKLIAEI
 51 AFQYRHGDPI PRVEYTAEEI ATWKEVYTTL KGLYATHACG EHLEAFALLE
101 RFSGYREDNI PQLEDVSRFL KERTGFQLRP VAGLLSARDF LASLAFRVFQ
151 CTQYIRHASS PMHSPEPDCC HELLGHVPML ADRTFAQFSQ DIGLASLGAS
201 DEEIEKLSTL SWFTVEFGLC KQNGEVKAYG AGLLSSYGEL LHCLSEEPEI
251 RAFDPEAAAV QPYQDQTYQS VYFVSESFSD AKDKLRSYAS RIQRPFSVKF
301 DPYTLAIDVL DSPQAVRRSL EGVQDELDTL AHALSAIG*
```

Figure 29 (cont.)

Fig. 29D. Nucleotide sequence of codon-optimized tyrosine hydroxylase, type 2 with serine encoded by nucleotides 631-633 (SEQ ID NO:25)

atggtgaaggtaccctggttcccaagaaaagtgtcagagctggacaagtgtcatcacctggtcaccaagttcgaccccgacct
ggacttggaccaccccggcttctcggaccaggtgtaccgccagcgcaggaagctgatcgctgagatcgccttccagtacagg
cacggcgacccgatccccgtgtggagtacaccgccgaggagatcgccacctggaaggaggtctacaccaccctgaaggg
cctctacgccacccacgcctgcggggagcacctggaggcctttgctttgctggagcgcttcagcggctaccgggaagacaac
atcccccagctggaggacgtctcccgcttcctgaaggagcgcacaggcttccagctgcggcccgtggccggcctgctgtccgc
ccgggacttcctggccagcctggccttccgcgtgttccagtgcacccagtatatccgccacgcgtcctcgcccatgcactcccct
gagccggactgctgccacgagctgctggggcacgtgcccatgctggccgaccgcaccttcgcgcagttcagccaggacatc
ggcctggcgtccctgggggccagcgatgaggaaatcgagaagctgtccactctgtcatggttcacggtggagttcgggctgtgt
aagcagaacggggaggtgaaggcctatggtgccgggctgctgtcctcctacggggagctcctgcactgcctgtctgaggagc
ctgagatccgggccttcgaccctgaggctgcggccgtgcagccctaccaagaccagacgtaccagtcagtctacttcgtgtctg
agagcttcagcgacgccaaggacaagctcaggagctatgccagccgcatccagcgcccccttctccgtgaagttcgacccgta
caccctggccatcgacgtgctggacagcccccaggccgtgcggcgctccctggagggtgtccaggatgagctggacacccttt
gcccatgcgctgagcgccatcggctga

Fig. 29E. Amino acid sequence of wild type truncated tyrosine hydroxylase, type 2 with tyrosine at position 211 (SEQ ID NO:26)

```
  1  MVKVPWFPRK  VSELDKCHHL  VTKFDPDLDL  DHPGFSDQVY  RQRRKLIAEI
 51  AFQYRHGDPI  PRVEYTAEEI  ATWKEVYTTL  KGLYATHACG  EHLEAFALLE
101  RFSGYREDNI  PQLEDVSRFL  KERTGFQLRP  VAGLLSARDF  LASLAFRVFQ
151  CTQYIRHASS  PMHSPEPDCC  HELLGHVPML  ADRTFAQFSQ  DIGLASLGAS
201  DEEIEKLSTL  YWFTVEFGLC  KQNGEVKAYG  AGLLSSYGEL  LHCLSEEPEI
251  RAFDPEAAAV  QPYQDQTYQS  VYFVSESFSD  AKDKLRSYAS  RIQRPFSVKF
301  DPYTLAIDVL  DSPQAVRRSL  EGVQDELDTL  AHALSAIG
```

Fig. 29F. Nucleotide sequence of truncated wild type tyrosine hydroxylase, type 2, with tyrosine encoded by nucleotides 631-633 (SEQ ID NO:27)

atggtgaaggtaccctggttcccaagaaaagtgtcagagctggacaagtgtcatcacctggtcaccaagttcgacctgacctg
gacttggaccacccgggcttctcggaccaggtgtaccgccagcgcaggaagctgattgctgagatcgccttccagtacaggc
acggcgacccgattccccgtgtggagtacaccgccgaggagattgccacctggaaggaggtctacaccacgctgaagggc
ctctacgccacgcacgcctgcggggagcacctggaggcctttgctttgctggagcgcttcagcggctaccgggaagacaatat
cccccagctggaggacgtctcccgcttcctgaaggagcgcacgggcttccagctgcggcctgtggccggcctgctgtccgccc
gggacttcctggccagcctggccttccgcgtgttccagtgcacccagtatatccgccacgcgtcctcgcccatgcactcccctga
gccggactgctgccacgagctgctggggcacgtgcccatgctggccgaccgcaccttcgcgcagttctcgcaggacattggc
ctggcgtccctgggggcctcggatgaggaaattgagaagctgtccacgctgtactggttcacggtggagttcgggctgtgtaag
cagaacggggaggtgaaggcctatggtgccgggctgctgtcctcctacggggagctcctgcactgcctgtctgaggagcctga
gattcgggccttcgaccctgaggctgcggccgtgcagccctaccaagaccagacgtaccagtcagtctacttcgtgtctgagag
cttcagtgacgccaaggacaagctcaggagctatgcctcacgcatccagcgcccccttctccgtgaagttcgacccgtacacgc
tggccatcgacgtgctggacagcccccaggccgtgcggcgctccctggagggtgtccaggatgagctggacacccttgccca
tgcgctgagtgccattggctag

Figure 29 (cont.)

Fig. 29G. Amino acid sequence of full-length tyrosine hydroxylase, type 2, with tyrosine at position 374 (SEQ ID NO:28)

```
  1   MPTPDATTPQ  AKGFRRAVSE  LDAKQAEAIM  VRGQSPRFIG  RRQSLIEDAR
 51   KEREAAVAAA  AAAVPSEPGD  PLEAVAFEEK  EGKAVLNLLF  SPRATKPSAL
101   SRAVKVFETF  EAKIHHLETR  PAQRPRAGGP  HLEYFVRLEV  RRGDLAALLS
151   GVRQVSEDVR  SPAGPKVPWF  PRKVSELDKC  HHLVTKFDPD  LDLDHPGFSD
201   QVYRQRRKLI  AEIAFQYRHG  DPIPRVEYTA  EEIATWKEVY  TTLKGLYATH
251   ACGEHLEAFA  LLERFSGYRE  DNIPQLEDVS  RFLKERTGFQ  LRPVAGLLSA
301   RDFLASLAFR  VFQCTQYIRH  ASSPMHSPEP  DCCHELLGHV  PMLADRTFAQ
351   FSQDIGLASL  GASDEEIEKL  STLYWFTVEF  GLCKQNGEVK  AYGAGLLSSY
401   GELLHCLSEE  PEIRAFDPEA  AAVQPYQDQT  YQSVYFVSES  FSDAKDKLRS
451   YASRIQRPFS  VKFDPYTLAI  DVLDSPQAVR  RSLEGVQDEL  DTLAHALSAI
501   G*
```

Fig. 29H. Nucleotide sequence of full-length tyrosine hydroxylase, type 2, which encodes tyrosine with nucleotides 1120-1122 (SEQ ID NO:29)

atgcccaccccgacgccaccacgccacaggccaagggcttccgcagggccgtgtctgagctggacgccaagcaggcagaggccat
catggtaagagggcagtccccgcggttcattgggcgcaggcagagcctcatcgaggacgcccgcaaggagcgggaggcggcggtgg
cagcagcggccgctgcagtcccctcggagccggggacccctggaggctgtggcctttgaggagaaggaggggaaggccgtgctaa
acctgctcttctccccgagggccaccaagccctcggcgctgtccgagctgtgaaggtgtttgagacgtttgaagccaaaatccaccatcta
gagaccggcccgcccagaggccgcgagctgggggcccccacctggagtacttcgtgcgcctcgaggtgcgccgaggggacctggcc
gccctgctcagtggtgtgcgccaggtgtcagaggacgtgcgcagccccgcggggcccaaggtcccctggttcccaagaaaagtgtcaga
gctggacaagtgtcatcacctggtcaccaagttcgaccctgacctggacttggaccacccgggcttctcggaccaggtgtaccgccagcgc
aggaagctgattgctgagatcgccttccagtacaggcacggcgaccgattccccgtgtggagtacaccgccgaggagattgccacctgg
aaggaggtctacaccacgctgaagggcctctacgccacgcacgcctgcggggagcacctggaggcctttgctttgctggagcgcttcagc
ggctaccgggaagacaatatcccccagctggaggacgtctccgcttcctgaaggagcgcacgggcttccagctgcggcctgtggccgg
cctgctgtccgcccgggacttcctggccagcctggcttccgcgtgttccagtgcacccagtatatccgccacgcgtcctcgcccatgcactc
ccctgagccggactgctgccacgagctgctggggcacgtgcccatgctggccgaccgcaccttcgcgcagttctcgcaggacattggcct
ggcgtccctgggggcctcggatgaggaaattgagaagctgtccacgctgtactggttcacggtggagttcgggctgtgtaagcagaacgg
ggaggtgaaggcctatggtgccgggctgctgtcctcctacggggagctcctgcactgcctgtctgaggagcctgagattcgggccttcgacc
ctgaggctgcggccgtgcagccctaccaagaccagacgtaccagtcagtctacttcgtgtctgagagcttcagtgacgccaaggacaagc
tcaggagctatgcctcacgcatccagcgccccttctccgtgaagttcgaccgtacacgctggccatcgacgtgctggacagcccccaggc
cgtgcggcgctccctggagggtgtccaggatgagctggacacccttgcccatgcgctgagtgccattggctag

Figure 30

Fig. 30A. Amino acid sequence of codon-optimized aromatic amino acid decarboxylase in pONY8.9.4 MV opti Y (SEQ ID NO:30)

```
  1  MDASEFRRRG  KEMVDYVANY  MEGIEGRQVY  PDVEPGYLRP  LIPAAAPQEP
 51  DTFEDIINDV  EKIIMPGVTH  WHSPYFFAYF  PTASSYPAML  ADMLCGAIGC
101  IGFSWAASPA  CTELETVMMD  WLGKMLELPK  AFLNEKAGEG  GGVIQGSASE
151  ATLVALLAAR  TKVIHRLQAA  SPELTQAAIM  EKLVAYSSDQ  AHSSVERAGL
201  IGGVKLKAIP  SDGNFAMRAS  ALQEALERDK  AAGLIPFFMV  ATLGTTTCCS
251  FDNLLEVGPI  CNKEDIWLHV  DAAYAGSAFI  CPEFRHLLNG  VEFADSFNFN
301  PHKWLLVNFD  CSAMWVKKRT  DLTGAFRLDP  TYLKHSHQDS  GLITDYRHWQ
351  IPLGRRFRSL  KMWFVFRMYG  VKGLQAYIRK  HVQLSHEFES  LVRQDPRFEI
401  CVEVILGLVC  FRLKGSNKVN  EALLQRINSA  KKIHLVPCHL  RDKFVLRFAI
451  CSRTVESAHV  QRAWEHIKEL  AADVLRAERE  *
```

Fig. 30B. Nucleotide sequence of codon-optimized aromatic amino acid decarboxylase in pONY8.9.4 MV opti Y (SEQ ID NO:31)

atggacgccagtgagttccgaaggcgcggcaaggagatggtggactacgtggccaactacatggaaggcatcgagggccg
ccaagtctaccccgacgtggagcccggctacctgcgcccgctgatccccgccgctgcccctcaggagcccgacaccttcgag
gacatcatcaacgacgtggagaagatcatcatgcctggcgtgacgcactggcacagcccctacttcttcgcctacttcccccacc
gccagctcgtacccggccatgctggcggacatgctgtgcggggccattggctgcatcggcttctcctgggcggcgagcccagc
gtgcaccgagctggagaccgtgatgatggactggctcgggaagatgctggagctcccaaaggcgttcttgaacgagaaggct
ggcgaggggggcggcgtgatccagggcagcgccagcgaggccaccctggtggccctgctggccgctcggaccaaagtga
tccaccggctgcaggcagcgtcccagagctcacccaggccgctatcatggagaagctggtggcttactcctccgatcaggc
acactcctccgtggaacgcgctgggctcattggtggagtgaagctcaaggccatcccagcgatggcaacttcgccatgcgtg
cgagcgccctgcaggaagccctggagagagacaaggcggctggcctgattcctttcttcatggtggccaccctggggaccac
aacatgctgctccttcgacaacctcctcgaagtcggtcctatctgcaacaaggaagacatctggctgcacgttgatgcagcctac
gcaggcagcgcattcatctgccctgagttccggcaccttctgaacggagtggagttcgcagatagcttcaacttcaatccccaca
agtggctattggtgaatttcgactgcagcgccatgtgggtgaagaagcgcaccgacctcacgggagccttccgcctggacccc
acttacctgaagcacagccaccaggattcagggcttatcactgactaccggcactggcagatcccactgggccgcagattccg
cagcttgaagatgtggttcgtattcaggatgtatggagtcaagggactgcaggcttatatccgcaagcatgtccagctgtcccatg
agtttgagtcactggtgcgccaggatccccgctttgaaatctgtgtggaagtcattctggggcttgtctgctttcggctaaagggttc
caacaaagtgaatgaagctcttctgcaaaggatcaacagtgccaaaaaaatccacttggttccatgtcacctcagggacaagt
ttgtcctgcgctttgccatctgttctcgcaccgtggaatctgcccatgtgcagcgggcctgggaacacatcaaagagctggcggc
cgacgtgctgcgagcagagagggagtag

Figure 30 (cont.)

Fig. 30C. Amino acid sequence of wild type aromatic amino acid decarboxylase (SEQ ID NO:32)

```
  1  MNASEFRRRG  KEMVDYVANY  MEGIEGRQVY  PDVEPGYLRP  LIPAAAPQEP
 51  DTFEDIINDV  EKIIMPGVTH  WHSPYFFAYF  PTASSYPAML  ADMLCGAIGC
101  IGFSWAASPA  CTELETVMMD  WLGKMLELPK  AFLNEKAGEG  GGVIQGSASE
151  ATLVALLAAR  TKVIHRLQAA  SPELTQAAIM  EKLVAYSSDQ  AHSSVERAGL
201  IGGVKLKAIP  SDGNFAMRAS  ALQEALERDK  AAGLIPFFMV  ATLGTTTCCS
251  FDNLLEVGPI  CNKEDIWLHV  DAAYAGSAFI  CPEFRHLLNG  VEFADSFNFN
301  PHKWLLVNFD  CSAMWVKKRT  DLTGAFRLDP  TYLKHSHQDS  GLITDYRHWQ
351  IPLGRRFRSL  KMWFVFRMYG  VKGLQAYIRK  HVQLSHEFES  LVRQDPRFEI
401  CVEVILGLVC  FRLKGSNKVN  EALLQRINSA  KKIHLVPCHL  RDKFVLRFAI
451  CSRTVESAHV  QRAWEHIKEL  AADVLRAERE  *
```

Fig. 30D. Nucleotide sequence of wild type aromatic amino acid decarboxylase (SEQ ID NO:33)

atgaacgcaagtgaattccgaaggagagggaaggagatggtggattacgtggccaactacatggaaggcattgagggacg
ccaggtctaccctgacgtggagcccgggtacctgcggccgctgatccctgccgctgcccctcaggagccagacacgtttgag
gacatcatcaacgacgttgagaagataatcatgcctggggtgacgcactggcacagcccctacttcttcgcctacttcccactg
ccagctcgtacccggccatgcttgcggacatgctgtgcggggccattggctgcatcggcttctcctgggcggcaagcccagcat
gcacagagctggagactgtgatgatggactggctcgggaagatgctggaactaccaaaggcattttgaatgagaaagctgg
agaaggggaggagtgatccagggaagtgccagtgaagccaccctggtggccctgctggccgctcggaccaaagtgatcc
atcggctgcaggcagcgtccccagagctcacacaggccgctatcatggagaagctggtggcttactcatccgatcaggcaca
ctcctcagtggaaagagctgggttaattggtggagtgaaattaaaagccatcccctcagatggcaacttcgccatgcgtgcgtct
gccctgcaggaagccctggagagagacaaagcggctggcctgattcctttctttatggttgccaccctggggaccacaacatg
ctgctcctttgacaatctcttagaagtcggtcctatctgcaacaaggaagacatatggctgcacgttgatgcagcctacgcaggc
agtgcattcatctgccctgagttccggcaccttctgaatggagtggagtttgcagattcattcaactttaatccccacaaatggctatt
ggtgaattttgactgttctgccatgtgggtgaaaaagagaacagacttaacgggagcctttagactggaccccacttacctgaag
cacagccatcaggattcagggcttatcactgactaccggcattggcagataccactgggcagaagatttcgctctttgaaaatgt
ggtttgtatttaggatgtatggagtcaaaggactgcaggcttatatccgcaagcatgtccagctgtcccatgagtttgagtcactgg
tgcgccaggatccccgctttgaaatctgtgtggaagtcattctggggcttgtctgctttcggctaaagggttccaacaaagtgaatg
aagctcttctgcaaagaataaacagtgccaaaaaaatccacttggttccatgtcacctcagggacaagtttgtcctgcgctttgcc
atctgttctcgcacggtggaatctgcccatgtgcagcgggcctgggaacacatcaaagagctggcggccgacgtgctgcgag
cagagagggagtag

SEQUENCE LISTING

<160> NUMBER OF SEQ ID NOS: 34

<210> SEQ ID NO 1
<211> LENGTH: 8531
<212> TYPE: DNA
<213> ORGANISM: Equine Infectious Anemia Virus

<400> SEQUENCE: 1

| | | | | | | |
|---|---|---|---|---|---|---|
| agatcttgaa | taataaaatg | tgtgtttgtc | cgaaatacgc | gttttgagat | ttctgtcgcc | 60 |
| gactaaattc | atgtcgcgcg | atagtggtgt | ttatcgccga | tagagatggc | gatattggaa | 120 |
| aaattgatat | ttgaaaatat | ggcatattga | aaatgtcgcc | gatgtgagtt | tctgtgtaac | 180 |
| tgatatcgcc | atttttccaa | aagtgatttt | tgggcatacg | cgatatctgg | cgatagcgct | 240 |
| tatatcgttt | acggggatg | gcgatagacg | actttggtga | cttgggcgat | tctgtgtgtc | 300 |
| gcaaatatcg | cagtttcgat | ataggtgaca | gacgatatga | ggctatatcg | ccgatagagg | 360 |
| cgacatcaag | ctggcacatg | gccaatgcat | atcgatctat | acattgaatc | aatattggcc | 420 |
| attagccata | ttattcattg | gttatatagc | ataaatcaat | attggctatt | ggccattgca | 480 |
| tacgttgtat | ccatatcgta | atatgtacat | ttatattggc | tcatgtccaa | cattaccgcc | 540 |
| atgttgacat | tgattattga | ctagttatta | atagtaatca | attacggggt | cattagttca | 600 |
| tagcccatat | atggagttcc | gcgttacata | acttacggta | aatggcccgc | ctggctgacc | 660 |
| gcccaacgac | ccccgcccat | tgacgtcaat | aatgacgtat | gttcccatag | taacgccaat | 720 |
| agggactttc | cattgacgtc | aatgggtgga | gtatttacgg | taaactgccc | acttggcagt | 780 |
| acatcaagtg | tatcatatgc | caagtccgcc | ccctattgac | gtcaatgacg | gtaaatggcc | 840 |
| cgcctggcat | tatgcccagt | acatgacctt | acgggacttt | cctacttggc | agtacatcta | 900 |
| cgtattagtc | atcgctatta | ccatggtgat | gcggttttgg | cagtacacca | atgggcgtgg | 960 |
| atagcggttt | gactcacggg | gatttccaag | tctccacccc | attgacgtca | atgggagttt | 1020 |
| gttttggcac | caaaatcaac | gggactttcc | aaaatgtcgt | aacaactgcg | atcgcccgcc | 1080 |
| ccgttgacgc | aaatgggcgg | taggcgtgta | cggtgggagg | tctatataag | cagagctcgt | 1140 |
| ttagtgaacc | gggcactcag | attctgcggt | ctgagtccct | tctctgctgg | gctgaaaagg | 1200 |
| cctttgtaat | aaatataatt | ctctactcag | tccctgtctc | tagtttgtct | gttcgagatc | 1260 |
| ctacagttgg | cgcccgaaca | gggacctgag | aggggcgcag | accctacctg | ttgaacctgg | 1320 |
| ctgatcgtag | gatccccggg | acagcagagg | agaacttaca | gaagtcttct | ggaggtgttc | 1380 |
| ctggccagaa | cacaggagga | caggtaagat | tgggagaccc | tttgacattg | gagcaaggcg | 1440 |
| ctcaagaagt | tagagaaggt | gacggtacaa | gggtctcaga | aattaactac | tggtaactgt | 1500 |
| aattgggcgc | taagtctagt | agacttattt | catgatacca | actttgtaaa | agaaaaggac | 1560 |
| tggcagctga | gggatgtcat | tccattgctg | aagatgtaa | ctcagacgct | gtcaggacaa | 1620 |
| gaaagagagg | cctttgaaag | aacatggtgg | gcaatttctg | ctgtaaagat | gggcctccag | 1680 |
| attaataatg | tagtagatgg | aaaggcatca | ttccagctcc | taagagcgaa | atatgaaaag | 1740 |
| aagactgcta | ataaaaagca | gtctgagccc | tctgaagaat | atctctagaa | ctagtggatc | 1800 |
| ccccgggctg | caggagtggg | gaggcacgat | ggccgctttg | gtcgaggcgg | atccggccat | 1860 |
| tagccatatt | attcattggt | tatatagcat | aaatcaatat | tggctattgg | ccattgcata | 1920 |
| cgttgtatcc | atatcataat | atgtacattt | atattggctc | atgtccaaca | ttaccgccat | 1980 |
| gttgacattg | attattgact | agttattaat | agtaatcaat | tacgggtca | ttagttcata | 2040 |

-continued

```
gcccatatat ggagttccgc gttacataac ttacggtaaa tggcccgcct ggctgaccgc    2100
ccaacgaccc ccgcccattg acgtcaataa tgacgtatgt tcccatagta acgccaatag    2160
ggactttcca ttgacgtcaa tgggtggagt atttacggta aactgcccac ttggcagtac    2220
atcaagtgta tcatatgcca agtacgcccc ctattgacgt caatgacggt aaatggcccg    2280
cctggcatta tgcccagtac atgaccttat gggactttcc tacttggcag tacatctacg    2340
tattagtcat cgctattacc atggtgatgc ggttttggca gtacatcaat gggcgtggat    2400
agcggtttga ctcacgggga tttccaagtc tccaccccat tgacgtcaat gggagtttgt    2460
tttggcacca aaatcaacgg gactttccaa aatgtcgtaa caactccgcc ccattgacgc    2520
aaatgggcgg taggcatgta cggtgggagg tctatataag cagagctcgt ttagtgaacc    2580
gtcagatcgc ctggagacgc catccacgct gttttgacct ccatagaaga caccgggacc    2640
gatccagcct ccgcggcccc aagcttgttg gatccaccg tcgccacca tggtgagcaa    2700 gggcgaggag ctgttcaccg gggtggtgcc catcctggtc gagctggacg gcgacgtaaa    2760
cggccacaag ttcagcgtgt ccggcgaggg cgagggcgat gccacctacg gcaagctgac    2820
cctgaagttc atctgcacca ccggcaagct gcccgtgccc tggcccaccc tcgtgaccac    2880
cctgacctac ggcgtgcagt gcttcagccg ctaccccgac cacatgaagc agcacgactt    2940
cttcaagtcc gccatgcccg aaggctacgt ccaggagcgc accatcttct tcaaggacga    3000
cggcaactac aagacccgcg ccgaggtgaa gttcgagggc gacaccctgg tgaaccgcat    3060
cgagctgaag ggcatcgact tcaaggagga cggcaacatc ctggggcaca gctggagta    3120 caactacaac agccacaacg tctatatcat ggccgacaag cagaagaacg gcatcaaggt    3180
gaacttcaag atccgccaca acatcgagga cggcagcgtg cagctcgccg accactacca    3240
gcagaacacc cccatcggcg acggccccgt gctgctgccc gacaaccact acctgagcac    3300
ccagtccgcc ctgagcaaag accccaacga gaagcgcgat cacatggtcc tgctggagtt    3360
cgtgaccgcc gccgggatca ctctcggcat ggacgagctg tacaagtaaa gcggccgcga    3420
ctctagagtc gacctgcagg catgcaagct tcagctgctc gagggggggc ccggtaccca    3480
gcttttgttc cctttagtga gggttaattg cgcgggaagt atttatcact aatcaagcac    3540
aagtaataca tgagaaactt ttactacagc aagcacaatc ctccaaaaaa ttttgttttt    3600
acaaaatccc tggtgaacat gattggaagg gacctactag ggtgctgtgg aagggtgatg    3660
gtgcagtagt agtaatgat gaaggaaagg gaataattgc tgtaccatta accaggacta    3720
agttactaat aaaaccaaat tgagtattgt tgcaggaagc aagacccaac taccattgtc    3780
agctgtgttt cctgacctca atatttgtta taaggtttga tatgaatccc aggggaatc    3840 tcaacccta ttacccaaca gtcagaaaaa tctaagtgtg aggagaacac aatgtttcaa    3900
ccttattgtt ataataatga cagtaagaac agcatggcag aatcgaagga agcaagagac    3960
caagaatgaa cctgaaagaa gaatctaaag aagaaaaag aagaaatgac tggtggaaaa    4020
taggtatgtt tctgttatgc ttagcaggaa ctactggagg aatactttgg tggtatgaag    4080
gactcccaca gcaacattat atagggttgg tggcgatagg gggaagatta aacggatctg    4140
gccaatcaaa tgctatagaa tgctgggggtt ccttcccggg gtgtagacca tttcaaaatt    4200
acttcagtta tgagaccaat agaagcatgc atatggataa taatactgct acattattag    4260
aagctttaac caatataact gctctataaa taacaaaaca gaattagaaa catggaagtt    4320
agtaaagact tctggcataa ctcctttacc tatttcttct gaagctaaca ctggactaat    4380
```

```
tagacataag agagattttg gtataagtgc aatagtggca gctattgtag ccgctactgc    4440
tattgctgct agcgctacta tgtcttatgt tgctctaact gaggttaaca aaataatgga    4500
agtacaaaat catactttg aggtagaaaa tagtactcta aatggtatgg atttaataga    4560
acgacaaata aagatattat atgctatgat tcttcaaaca catgcagatg ttcaactgtt    4620
aaaggaaaga caacaggtag aggagacatt taatttaatt ggatgtatag aaagaacaca    4680
tgtattttgt catactggtc atccctggaa tatgtcatgg ggacatttaa atgagtcaac    4740
acaatgggat gactgggtaa gcaaaatgga agatttaaat caagagatac taactacact    4800
tcatggagcc aggaacaatt tggcacaatc catgataaca ttcaatacac cagatagtat    4860
agctcaattt ggaaaagacc tttggagtca tattggaaat tggattcctg gattgggagc    4920
ttccattata aaatatatag tgatgttttt gcttattat ttgttactaa cctcttcgcc    4980
taagatcctc agggccctct ggaaggtgac cagtggtgca gggtcctccg gcagtcgtta    5040
cctgaagaaa aaattccatc acaaacatgc atcgcgagaa cacactgggg accaggccca    5100
acacaacata cacctagcag gcgtgaccgg tgatcaggg acaaatact acaagcagaa    5160
gtactccagg aacgactgga atggagaatc agaggagtac aacaggcggc caaagagctg    5220
ggtgaagtca atcgaggcat ttggagagag ctatatttcc gagaagacca aggggagat    5280
ttctcagcct ggggcggcta tcaacgagca caagaacggc tctggggga acaatcctca    5340
ccaagggtcc ttagacctgg agattcgaag cgaaggagga acatttatg actgttgcat    5400
taaagcccaa gaaggaactc tcgctatccc ttgctgtgga ttcccttat ggctattttg    5460
gggactagta attatagtag gacgcatagc aggctatgga ttacgtggac tcgctgttat    5520
aataaggatt tgtattagag gcttaaattt gatatttgaa ataatcagaa aaatgcttga    5580
ttatattgga agagctttaa atcctggcac atctcatgta tcaatgcctc agtatgttta    5640
gaaaaacaag gggggaactg tggggtttt atgaggggtt ttataaatga ttataagagt    5700
aaaaagaaag ttgctgatgc tctcataacc ttgtataacc caaggacta gctcatgttg    5760
ctaggcaact aaaccgcaat aaccgcattt gtgacgcgag ttccccattg gtgacgcgtt    5820
aacttcctgt ttttacagta tataagtgct tgtattctga caattgggca ctcagattct    5880
gcggtctgag tcccttctct gctgggctga aaaggccttt gtaataaata taattctcta    5940
ctcagtccct gtctctagtt tgtctgttcg agatcctaca gagctcatgc cttggcgtaa    6000
tcatggtcat agctgtttcc tgtgtgaaat tgttatccgc tcacaattcc acacaacata    6060
cgagccggaa gcataaagtg taaagcctgg ggtgcctaat gagtgagcta actcacatta    6120
attgcgttgc gctcactgcc cgcttttccag tcgggaaacc tgtcgtgcca gctgcattaa    6180
tgaatcggcc aacgcgcggg gagaggcggt ttgcgtattg ggcgctcttc cgcttcctcg    6240
ctcactgact cgctgcgctc ggtcgttcgg ctgcggcgag cggtatcagc tcactcaaag    6300
gcggtaatac ggttatccac agaatcaggg gataacgcag gaaagaacat gtgagcaaaa    6360
ggccagcaaa aggccaggaa ccgtaaaaag gccgcgttgc tggcgttttt ccataggctc    6420
cgcccccctg acgagcatca caaaaatcga cgctcaagtc agaggtggcg aaacccgaca    6480
ggactataaa gataccaggc gtttccccct ggaagctccc tcgtgcgctc tcctgttccg    6540
accctgccgc ttaccggata cctgtccgcc tttctccctt cgggaagcgt ggcgctttct    6600
catagctcac gctgtaggta tctcagttcg gtgtaggtcg ttcgctccaa gctgggctgt    6660
gtgcacgaac cccccgttca gcccgaccgc tgcgccttat ccggtaacta tcgtcttgag    6720
tccaacccgg taagacacga cttatcgcca ctggcagcag ccactggtaa caggattagc    6780
```

-continued

```
agagcgaggt atgtaggcgg tgctacagag ttcttgaagt ggtggcctaa ctacggctac      6840
actagaagga cagtatttgg tatctgcgct ctgctgaagc cagttacctt cggaaaaaga      6900
gttggtagct cttgatccgg caaacaaacc accgctggta gcggtggttt ttttgtttgc      6960
aagcagcaga ttacgcgcag aaaaaaagga tctcaagaag atcctttgat cttttctacg      7020
gggtctgacg ctcagtggaa cgaaaactca cgttaaggga ttttggtcat gagattatca      7080
aaaaggatct tcacctagat ccttttaaat taaaaatgaa gttttaaatc aatctaaagt      7140
atatatgagt aaacttggtc tgacagttac caatgcttaa tcagtgaggc acctatctca      7200
gcgatctgtc tatttcgttc atccatagtt gcctgactcc ccgtcgtgta gataactacg      7260
atacgggagg gcttaccatc tggccccagt gctgcaatga taccgcgaga cccacgctca      7320
ccggctccag atttatcagc aataaaccag ccagccggaa gggccgagcg cagaagtggt      7380
cctgcaactt tatccgcctc catccagtct attaattgtt gccgggaagc tagagtaagt      7440
agttcgccag ttaatagttt gcgcaacgtt gttgccattg ctacaggcat cgtggtgtca      7500
cgctcgtcgt ttggtatggc ttcattcagc tccggttccc aacgatcaag gcgagttaca      7560
tgatccccca tgttgtgcaa aaaagcggtt agctccttcg gtcctccgat cgttgtcaga      7620
agtaagttgg ccgcagtgtt atcactcatg gttatggcag cactgcataa ttctcttact      7680
gtcatgccat ccgtaagatg cttttctgtg actggtgagt actcaaccaa gtcattctga      7740
gaatagtgta tgcggcgacc gagttgctct tgcccggcgt caatacggga taataccgcg      7800
ccacatagca gaactttaaa agtgctcatc attggaaaac gttcttcggg gcgaaaactc      7860
tcaaggatct taccgctgtt gagatccagt tcgatgtaac ccactcgtgc acccaactga      7920
tcttcagcat cttttacttt caccagcgtt tctgggtgag caaaaacagg aaggcaaaat      7980
gccgcaaaaa agggaataag ggcgacacgg aaatgttgaa tactcatact cttccttttt      8040
caatattatt gaagcattta tcagggttat tgtctcatga gcggatacat atttgaatgt      8100
atttagaaaa ataaacaaat aggggttccg cgcacatttc cccgaaaagt gccacctaaa      8160
ttgtaagcgt taatattttg ttaaaattcg cgttaaattt ttgttaaatc agctcatttt      8220
ttaaccaata ggccgaaatc ggcaaaatcc cttataaatc aaaagaatag accgagatag      8280
ggttgagtgt tgttccagtt tggaacaaga gtccactatt aaagaacgtg gactccaacg      8340
tcaaagggcg aaaaaccgtc tatcagggcg atggcccact acgtgaacca tcaccctaat      8400 caagttttt ggggtcgagg tgccgtaaag cactaaatcg gaaccctaaa gggagccccc      8460
gatttagagc ttgacgggga agccaacct ggcttatcga aattaatacg actcactata      8520
gggagaccgg c                                                          8531
```

<210> SEQ ID NO 2
<211> LENGTH: 6418
<212> TYPE: DNA
<213> ORGANISM: Equine Infectious Anemia Virus

<400> SEQUENCE: 2

```
agatcttgaa taataaaatg tgtgtttgtc cgaaatacgc gttttgagat ttctgtcgcc        60
gactaaattc atgtcgcgcg atagtggtgt ttatcgccga tagagatggc gatattggaa       120
aaattgatat ttgaaaatat ggcatattga aaatgtcgcc gatgtgagtt tctgtgtaac       180
tgatatcgcc attttccaa aagtgatttt tgggcatacg cgatatctgg cgatagcgct       240
tatatcgttt acggggatg gcgatagacg actttggtga cttgggcgat tctgtgtgtc       300
```

-continued

```
gcaaatatcg cagtttcgat ataggtgaca gacgatatga ggctatatcg ccgatagagg      360
cgacatcaag ctggcacatg gccaatgcat atcgatctat acattgaatc aatattggcc      420
attagccata ttattcattg gttatatagc ataaatcaat attggctatt ggccattgca      480
tacgttgtat ccatatcgta atatgtacat ttatattggc tcatgtccaa cattaccgcc      540
atgttgacat tgattattga ctagttatta atagtaatca attacggggt cattagttca      600
tagcccatat atggagttcc gcgttacata acttacggta aatggcccgc ctggctgacc      660
gcccaacgac ccccgcccat tgacgtcaat aatgacgtat gttcccatag taacgccaat      720
agggactttc cattgacgtc aatgggtgga gtatttacgg taaactgccc acttggcagt      780
acatcaagtg tatcatatgc caagtccgcc ccctattgac gtcaatgacg gtaaatggcc      840
cgcctggcat tatgcccagt acatgacctt acgggactttc ctacttggc agtacatcta      900 cgtattagtc atcgctatta ccatggtgat gcggttttgg cagtacacca atgggcgtgg      960
atagcggttt gactcacggg gatttccaag tctccacccc attgacgtca atgggagttt     1020
gttttggcac caaaatcaac gggactttcc aaaatgtcgt aacaactgcg atcgcccgcc     1080
ccgttgacga aatgggcgg taggcgtgta cggtgggagg tctatataag cagagctcgt      1140
ttagtgaacc gggcactcag attctgcggt ctgagtccct tctctgctgg gctgaaaagg     1200
cctttgtaat aaatataatt ctctactcag tccctgtctc tagtttgtct gttcgagatc     1260
ctacagttgg cgcccgaaca gggacctgag aggggcgcag accctacctg ttgaacctgg     1320
ctgatcgtag gatccccggg acagcagagg agaacttaca gaagtcttct ggaggtgttc     1380
ctggccagaa cacaggagga caggtaagat tgggagaccc tttgacattg gagcaaggcg     1440
ctcaagaagt tagagaaggt gacggtacaa gggtctcaga aattaactac tggtaactgt     1500
aattgggcgc taagtctagt agacttattt catgatacca actttgtaaa agaaaaggac     1560
tggcagctga gggatgtcat tccattgctg gaagatgtaa ctcagacgct gtcaggacaa     1620
gaaagagagg cctttgaaag aacatggtgg gcaatttctg ctgtaaagat gggcctccag     1680
attaataatg tagtagatgg aaaggcatca ttccagctcc taagagcgaa atatgaaaag     1740
aagactgcta ataaaaagca gtctgagccc tctgaagaat atctctagaa ctagtggatc     1800
ccccgggctg caggagtggg gaggcacgat ggccgctttg gtcgaggcgg atccggccat     1860
tagccatatt attcattggt tatatagcat aaatcaatat ggctattgg ccattgcata     1920 cgttgtatcc atatcataat atgtacattt atattggctc atgtccaaca ttaccgccat     1980
gttgacattg attattgact agttattaat agtaatcaat tacggggtca ttagttcata     2040
gcccatatat ggagttccgc gttacataac ttacggtaaa tggcccgcct ggctgaccgc     2100
ccaacgaccc ccgcccattg acgtcaataa tgacgtatgt tcccatagta acgccaatag     2160
ggactttcca ttgacgtcaa tgggtggagt atttacggta aactgcccac ttggcagtac     2220
atcaagtgta tcatatgcca gtacgcccc ctattgacgt caatgacggt aaatggcccg      2280
cctggcatta tgcccagtac atgaccttat gggactttcc tacttggcag tacatctacg     2340
tattagtcat cgctattacc atggtgatgc ggttttggca gtacatcaat gggcgtggat     2400
agcggtttga ctcacgggga tttccaagtc tccacccat tgacgtcaat gggagtttgt      2460
tttggcacca aaatcaacgg gactttccaa aatgtcgtaa caactccgcc ccattgacgc     2520 aaatggcgg taggcatgta cggtgggagg tctatataag cagagctcgt ttagtgaacc      2580
gtcagatcgc ctggagacgc catccacgct gttttgacct ccatagaaga caccgggacc     2640
gatccagcct ccgcggcccc aagcttgttg ggatccaccg gtcgccacca tggtgagcaa     2700
```

```
gggcgaggag ctgttcaccg gggtggtgcc catcctggtc gagctggacg gcgacgtaaa   2760
cggccacaag ttcagcgtgt ccggcgaggg cgagggcgat gccacctacg gcaagctgac   2820
cctgaagttc atctgcacca ccggcaagct gcccgtgccc tggcccaccc tcgtgaccac   2880
cctgacctac ggcgtgcagt gcttcagccg ctaccccgac cacatgaagc agcacgactt   2940
cttcaagtcc gccatgcccg aaggctacgt ccaggagcgc accatcttct tcaaggacga   3000
cggcaactac aagacccgcg ccgaggtgaa gttcgagggc gacaccctgg tgaaccgcat   3060
cgagctgaag ggcatcgact tcaaggagga cggcaacatc ctggggcaca agctggagta   3120
caactacaac agccacaacg tctatatcat ggccgacaag cagaagaacg gcatcaaggt   3180
gaacttcaag atccgccaca acatcgagga cggcagcgtg cagctcgccg accactacca   3240
gcagaacacc cccatcggcg acggccccgt gctgctgccc gacaaccact acctgagcac   3300
ccagtccgcc ctgagcaaag accccaacga gaagcgcgat cacatggtcc tgctggagtt   3360
cgtgaccgcc gccgggatca ctctcggcat ggacgagctg tacaagtaaa gcggccgcga   3420
ctctagagtc gacctgcagg aattcgatat caagcttatc gataccgtcg aattggaaga   3480
gctttaaatc ctggcacatc tcatgtatca atgcctcagt atgtttagaa aaacaagggg   3540
ggaactgtgg ggttttttatg aggggttttta taatgatta taagagtaaa aagaaagttg   3600
```

```
gggcgaggag ctgttcaccg gggtggtgcc catcctggtc gagctggacg gcgacgtaaa   2760
cggccacaag ttcagcgtgt ccggcgaggg cgagggcgat gccacctacg gcaagctgac   2820
cctgaagttc atctgcacca ccggcaagct gcccgtgccc tggcccaccc tcgtgaccac   2880
cctgacctac ggcgtgcagt gcttcagccg ctaccccgac cacatgaagc agcacgactt   2940
cttcaagtcc gccatgcccg aaggctacgt ccaggagcgc accatcttct tcaaggacga   3000
cggcaactac aagacccgcg ccgaggtgaa gttcgagggc gacaccctgg tgaaccgcat   3060
cgagctgaag ggcatcgact tcaaggagga cggcaacatc ctggggcaca agctggagta   3120
caactacaac agccacaacg tctatatcat ggccgacaag cagaagaacg gcatcaaggt   3180
gaacttcaag atccgccaca acatcgagga cggcagcgtg cagctcgccg accactacca   3240
gcagaacacc cccatcggcg acggccccgt gctgctgccc gacaaccact acctgagcac   3300
ccagtccgcc ctgagcaaag accccaacga gaagcgcgat cacatggtcc tgctggagtt   3360
cgtgaccgcc gccgggatca ctctcggcat ggacgagctg tacaagtaaa gcggccgcga   3420
ctctagagtc gacctgcagg aattcgatat caagcttatc gataccgtcg aattggaaga   3480
gctttaaatc ctggcacatc tcatgtatca atgcctcagt atgtttagaa aaacaagggg   3540
ggaactgtgg ggtttttatg aggggtttta taatgatta taagagtaaa aagaaagttg   3600
ctgatgctct cataaccttg tataacccaa aggactagct catgttgcta ggcaactaaa   3660
ccgcaataac cgcatttgtg acgcgagttc cccattggtg acgcgttaac ttcctgtttt   3720
tacagtatat aagtgcttgt attctgacaa ttgggcactc agattctgcg gtctgagtcc   3780
cttctctgct gggctgaaaa ggcctttgta ataaatataa ttctctactc agtccctgtc   3840
tctagtttgt ctgttcgaga tcctacagag ctcatgcctt ggcgtaatca tggtcatagc   3900
tgtttcctgt gtgaaattgt tatccgctca caattccaca acatacga gccggaagca   3960
taaagtgtaa agcctggggt gcctaatgag tgagctaact cacattaatt gcgttgcgct   4020
cactgcccgc tttccagtcg ggaaacctgt cgtgccagct gcattaatga atcggccaac   4080
gcgcggggag aggcggtttg cgtattgggc gctcttccgc ttcctcgctc actgactcgc   4140
tgcgctcggt cgttcggctg cggcgagcgg tatcagctca ctcaaaggcg gtaatacggt   4200
tatccacaga atcaggggat aacgcaggaa agaacatgtg agcaaaaggc cagcaaaagg   4260
ccaggaaccg taaaaaggcc gcgttgctgg cgtttttcca taggctccgc cccccctgacg   4320
agcatcacaa aaatcgacgc tcaagtcaga ggtggcgaaa cccgacagga ctataaagat   4380
accaggcgtt tccccctgga agctccctcg tgcgctctcc tgttccgacc ctgccgctta   4440
ccggatacct gtccgccttt ctcccttcgg aagcgtggc gctttctcat agctcacgct   4500
gtaggtatct cagttcggtg taggtcgttc gctccaagct gggctgtgtg cacgaaccc   4560
ccgttcagcc cgaccgctgc gccttatccg gtaactatcg tcttgagtcc aacccggtaa   4620
gacacgactt atcgccactg gcagcagcca ctggtaacag gattagcaga gcgaggtatg   4680
taggcggtgc tacagagttc ttgaagtggt ggcctaacta cggctacact agaaggacag   4740
tatttggtat ctgcgctctg ctgaagccag ttaccttcgg aaaaagagtt ggtagctctt   4800
gatccggcaa acaaaccacc gctggtagcg gtggtttttt tgtttgcaag cagcagatta   4860
cgcgcagaaa aaaggatctc aagaagatc ctttgatctt ttctacgggg tctgacgctc   4920
agtggaacga aaactcacgt taagggattt tggtcatgag attatcaaaa aggatcttca   4980
cctagatcct tttaaattaa aaatgaagtt ttaaatcaat ctaaagtata tatgagtaaa   5040
```

```
cttggtctga cagttaccaa tgcttaatca gtgaggcacc tatctcagcg atctgtctat    5100
ttcgttcatc catagttgcc tgactccccg tcgtgtagat aactacgata cgggagggct    5160
taccatctgg ccccagtgct gcaatgatac cgcgagaccc acgctcaccg gctccagatt    5220
tatcagcaat aaaccagcca gccggaaggg ccgagcgcag aagtggtcct gcaactttat    5280
ccgcctccat ccagtctatt aattgttgcc gggaagctag agtaagtagt tcgccagtta    5340
atagtttgcg caacgttgtt gccattgcta caggcatcgt ggtgtcacgc tcgtcgtttg    5400
gtatggcttc attcagctcc ggttcccaac gatcaaggcg agttacatga tcccccatgt    5460
tgtgcaaaaa agcggttagc tccttcggtc ctccgatcgt tgtcagaagt aagttggccg    5520
cagtgttatc actcatggtt atggcagcac tgcataattc tcttactgtc atgccatccg    5580
taagatgctt ttctgtgact ggtgagtact caaccaagtc attctgagaa tagtgtatgc    5640
ggcgaccgag ttgctcttgc ccggcgtcaa tacgggataa taccgcgcca catagcagaa    5700
ctttaaaagt gctcatcatt ggaaaacgtt cttcggggcg aaaactctca aggatcttac    5760
cgctgttgag atccagttcg atgtaaccca ctcgtgcacc caactgatct tcagcatctt    5820
ttactttcac cagcgtttct gggtgagcaa aaacaggaag gcaaaatgcc gcaaaaaagg    5880
gaataagggc gacacggaaa tgttgaatac tcatactctt ccttttcaa tattattgaa    5940 gcatttatca gggttattgt ctcatgagcg gatacatatt tgaatgtatt tagaaaaata    6000
aacaaatagg ggttccgcgc acatttcccc gaaaagtgcc acctaaattg taagcgttaa    6060
tattttgtta aaattcgcgt taaatttttg ttaaatcagc tcatttttta accaataggc    6120
cgaaatcggc aaaatccctt ataaatcaaa agaatagacc gagatagggt tgagtgttgt    6180
tccagtttgg aacaagagtc cactattaaa gaacgtggac tccaacgtca aagggcgaaa    6240
aaccgtctat cagggcgatg gcccactacg tgaaccatca ccctaatcaa gttttttggg    6300
gtcgaggtgc cgtaaagcac taaatcggaa ccctaaaggg agcccccgat ttagagcttg    6360
acggggaaag ccaacctggc ttatcgaaat taatacgact cactataggg agaccggc      6418

<210> SEQ ID NO 3
<211> LENGTH: 10998
<212> TYPE: DNA
<213> ORGANISM: Equine Infectious Anemia Virus

<400> SEQUENCE: 3
agatcttgaa taataaaatg tgtgtttgtc cgaaatacgc gttttgagat ttctgtcgcc      60
gactaaattc atgtcgcgcg atagtggtgt ttatcgccga tagagatggc gatattggaa     120
aaattgatat ttgaaaatat ggcatattga aaatgtcgcc gatgtgagtt tctgtgtaac     180
tgatatcgcc atttttccaa aagtgatttt tgggcatacg cgatatctgg cgatagcgct     240
tatatcgttt acggggatg gcgatagacg actttggtga cttgggcgat tctgtgtgtc      300
gcaaatatcg cagtttcgat ataggtgaca gacgatatga ggctatatcg ccgatagagg     360
cgacatcaag ctggcacatg gccaatgcat atcgatctat acattgaatc aatattggcc     420
attagccata ttattcattg gttatatagc ataaatcaat attggctatt ggccattgca     480
tacgttgtat ccatatcgta atatgtacat ttatattggc tcatgtccaa cattaccgcc     540
atgttgacat tgattattga ctagttatta atagtaatca attacggggt cattagttca     600
tagcccatat atggagttcc gcgttacata acttacggta aatggcccgc ctggctgacc     660
gcccaacgac ccccgcccat tgacgtcaat aatgacgtat gttcccatag taacgccaat     720
agggactttc cattgacgtc aatgggtgga gtatttacgg taaactgccc acttggcagt     780
```

-continued

| | |
|---|---|
| acatcaagtg tatcatatgc caagtccgcc ccctattgac gtcaatgacg gtaaatggcc | 840 |
| cgcctggcat tatgcccagt acatgacctt acgggacttt cctacttggc agtacatcta | 900 |
| cgtattagtc atcgctatta ccatggtgat gcggttttgg cagtacacca atgggcgtgg | 960 |
| atagcggttt gactcacggg gatttccaag tctccacccc attgacgtca atgggagttt | 1020 |
| gttttggcac caaaatcaac gggactttcc aaaatgtcgt aacaactgcg atcgcccgcc | 1080 |
| ccgttgacgc aaatgggcgg taggcgtgta cggtgggagg tctatataag cagagctcgt | 1140 |
| ttagtgaacc gggcactcag attctgcggt ctgagtccct tctctgctgg gctgaaaagg | 1200 |
| cctttgtaat aaatataatt ctctactcag tccctgtctc tagtttgtct gttcgagatc | 1260 |
| ctacagttgg cgcccgaaca gggacctgag aggggcgcag accctacctg ttgaacctgg | 1320 |
| ctgatcgtag gatccccggg acagcagagg agaacttaca gaagtcttct ggaggtgttc | 1380 |
| ctggccagaa cacaggagga caggtaagat tgggagaccc tttgacattg gagcaaggcg | 1440 |
| ctcaagaagt tagagaaggt gacggtacaa gggtctcaga aattaactac tggtaactgt | 1500 |
| aattgggcgc taagtctagt agacttattt catgatacca actttgtaaa agaaaaggac | 1560 |
| tggcagctga gggatgtcat tccattgctg gaagatgtaa ctcagacgct gtcaggacaa | 1620 |
| gaaagagagg cctttgaaag aacatggtgg gcaatttctg ctgtaaagat gggcctccag | 1680 |
| attaataatg tagtagatgg aaaggcatca ttccagctcc taagagcgaa atatgaaaag | 1740 |
| aagactgcta ataaaaagca gtctgagccc tctgaagaat atctctagaa ctagtggatc | 1800 |
| ccccgggctg caggagtggg gaggcacgat ggccgctttg gtcgaggcgg atccggccat | 1860 |
| tagccatatt attcattggt tatatagcat aaatcaatat tggctattgg ccattgcata | 1920 |
| cgttgtatcc atatcataat atgtacattt atattggctc atgtccaaca ttaccgccat | 1980 |
| gttgacattg attattgact agttattaat agtaatcaat tacgggtca ttagttcata | 2040 |
| gcccatatat ggagttccgc gttacataac ttacggtaaa tggcccgcct ggctgaccgc | 2100 |
| ccaacgaccc ccgcccattg acgtcaataa tgacgtatgt tcccatagta acgccaatag | 2160 |
| ggactttcca ttgacgtcaa tgggtggagt atttacggta aactgcccac ttggcagtac | 2220 |
| atcaagtgta tcatatgcca agtacgcccc ctattgacgt caatgacggt aaatggcccg | 2280 |
| cctggcatta tgcccagtac atgaccttat gggactttcc tacttggcag tacatctacg | 2340 |
| tattagtcat cgctattacc atggtgatgc ggttttggca gtacatcaat gggcgtggat | 2400 |
| agcggtttga ctcacgggga tttccaagtc tccaccccat tgacgtcaat gggagtttgt | 2460 |
| tttggcacca aaatcaacgg gactttccaa aatgtcgtaa caactccgcc ccattgacgc | 2520 |
| aaatgggcgg taggcatgta cggtgggagg tctatataag cagagctcgt ttagtgaacc | 2580 |
| gtcagatcgc ctggagacgc catccacgct gttttgacct ccatagaaga caccgggacc | 2640 |
| gatccagcct ccgcggcccc aagcttcagc tgctcgagga tctgcggatc cggggaattc | 2700 |
| cccagtctca ggatccacca tgggggatcc cgtcgtttta caacgtcgtg actgggaaaa | 2760 |
| ccctggcgtt acccaactta atcgccttgc agcacatccc cctttcgcca gctggcgtaa | 2820 |
| tagcgaagag gcccgcaccg atcgcccttc ccaacagttg cgcagcctga atggcgaatg | 2880 |
| gcgctttgcc tggtttccgg caccagaagc ggtgccggaa agctggctgg agtgcgatct | 2940 |
| tcctgaggcc gatactgtcg tcgtcccctc aaactggcag atgcacggtt acgatgcgcc | 3000 |
| catctacacc aacgtaacct atcccattac ggtcaatccg ccgtttgttc ccacggagaa | 3060 |
| tccgacgggt tgttactcgc tcacatttaa tgttgatgaa agctggctac aggaaggcca | 3120 |

-continued

| | |
|---|---|
| gacgcgaatt attttgatg gcgttaactc ggcgtttcat ctgtggtgca acgggcgctg | 3180 |
| ggtcggttac ggccaggaca gtcgtttgcc gtctgaattt gacctgagcg cattttacg | 3240 |
| cgccggagaa aaccgcctcg cggtgatggt gctgcgttgg agtgacggca gttatctgga | 3300 |
| agatcaggat atgtggcgga tgagcggcat tttccgtgac gtctcgttgc tgcataaacc | 3360 |
| gactacacaa atcagcgatt ccatgttgc cactcgcttt aatgatgatt tcagccgcgc | 3420 |
| tgtactggag gctgaagttc agatgtgcgg cgagttgcgt gactacctac gggtaacagt | 3480 |
| ttctttatgg cagggtgaaa cgcaggtcgc cagcggcacc gcgcctttcg gcggtgaaat | 3540 |
| tatcgatgag cgtggtggtt atgccgatcg cgtcacacta cgtctgaacg tcgaaaaccc | 3600 |
| gaaactgtgg agcgccgaaa tcccgaatct ctatcgtgcg gtggttgaac tgcacaccgc | 3660 |
| cgacggcacg ctgattgaag cagaagcctg cgatgtcggt ttccgcgagg tgcggattga | 3720 |
| aaatggtctg ctgctgctga acggcaagcc gttgctgatt cgaggcgtta accgtcacga | 3780 |
| gcatcatcct ctgcatggtc aggtcatgga tgagcagacg atggtgcagg atatcctgct | 3840 |
| gatgaagcag aacaacttta acgccgtgcg ctgttcgcat tatccgaacc atccgctgtg | 3900 |
| gtacacgctg tgcgaccgct acggcctgta tgtggtggat gaagccaata ttgaaaccca | 3960 |
| cggcatggtg ccaatgaatc gtctgaccga tgatccgcgc tggctaccgg cgatgagcga | 4020 |
| acgcgtaacg cgaatggtgc agcgcgatcg taatcacccg agtgtgatca tctggtcgct | 4080 |
| ggggaatgaa tcaggccacg cgctaatca cgacgcgctg tatcgctgga tcaaatctgt | 4140 |
| cgatccttcc cgcccggtgc agtatgaagg cggcggagcc gacaccacgg ccaccgatat | 4200 |
| tatttgcccg atgtacgcgc gcgtggatga agaccagccc ttcccggctg tgccgaaatg | 4260 |
| gtccatcaaa aaatggcttt cgctacctgg agagacgcgc ccgctgatcc tttgcgaata | 4320 |
| cgcccacgcg atgggtaaca gtcttggcgg tttcgctaaa tactggcagg cgtttcgtca | 4380 |
| gtatccccgt ttacagggcg gcttcgtctg ggactgggtg gatcagtcgc tgattaaata | 4440 |
| tgatgaaaac ggcaacccgt ggtcggctta cggcggtgat tttggcgata cgccgaacga | 4500 |
| tcgccagttc tgtatgaacg gtctggtctt tgccgaccgc acgccgcatc cagcgctgac | 4560 |
| ggaagcaaaa caccagcagc agtttttcca gttccgttta tccgggcaaa ccatcgaagt | 4620 |
| gaccagcgaa tacctgttcc gtcatagcga taacgagctc ctgcactgga tggtggcgct | 4680 |
| ggatggtaag ccgctggcaa gcggtgaagt gcctctggat gtcgctccac aagtaaaca | 4740 |
| gttgattgaa ctgcctgaac taccgcagcc ggagagcgcc gggcaactct ggctcacagt | 4800 |
| acgcgtagtg caaccgaacg cgaccgcatg gtcagaagcc gggcacatca gcgcctggca | 4860 |
| gcagtggcgt ctggcggaaa acctcagtgt gacgctcccc gccgcgtccc acgccatccc | 4920 |
| gcatctgacc accagcgaaa tggattttg catcgagctg ggtaataagc gttggcaatt | 4980 |
| taaccgccag tcaggctttc tttcacagat gtggattggc gataaaaac aactgctgac | 5040 |
| gccgctcgcg gatcagttca cccgtgcacc gctggataac gacattggcg taagtgaagc | 5100 |
| gacccgcatt gaccctaacg cctgggtcga acgctggaag gcggcgggcc attaccaggc | 5160 |
| cgaagcagcg ttgttgcagt gcacggcaga tacacttgct gatgcggtgc tgattacgac | 5220 |
| cgctcacgcg tggcagcatc aggggaaaac cttatttatc agccggaaaa cctaccggat | 5280 |
| tgatggtagt ggtcaaatgg cgattaccgt tgatgttgaa gtggcgagcg atacaccgca | 5340 |
| tccggcgcgg attggcctga actgccagct ggcgcaggta gcagagcggg taaactggct | 5400 |
| cggattaggg ccgcaagaaa actatcccga ccgccttact gccgcctgtt ttgaccgctg | 5460 |
| ggatctgcca ttgtcagaca tgtataccc gtacgtcttc ccgagcgaaa acggtctgcg | 5520 |

```
ctgcgggacg cgcgaattga attatggccc acaccagtgg cgcggcgact tccagttcaa   5580
catcagccgc tacagtcaac agcaactgat ggaaaccagc catcgccatc tgctgcacgc   5640
ggaagaaggc acatggctga atatcgacgg tttccatatg gggattggtg gcgacgactc   5700
ctggagcccg tcagtatcgg cggaattcca gctgagcgcc ggtcgctacc attaccagtt   5760
ggtctggtgt caaaaataat aataaccggg caggggggat ccgcagatcc ggctgtggaa   5820
tgtgtgtcag ttagggtgtg aaagtcccc aggctcccca gcaggcagaa gtatgcaaag    5880
catgcctgca ggaattcgat atcaagctta tcgataccgt cgacctcgag ggggggcccg   5940
gtacccagct tttgttccct ttagtgaggg ttaattgcgc gggaagtatt tatcactaat   6000
caagcacaag taatacatga gaacttttta ctacagcaag cacaatcctc caaaaattt    6060 tgttttaca aatccctgg tgaacatgat tggaagggac ctactagggt gctgtggaag     6120
ggtgatggtg cagtagtagt taatgatgaa ggaaagggaa taattgctgt accattaacc   6180
aggactaagt tactaataaa accaaattga gtattgttgc aggaagcaag acccaactac   6240
cattgtcagc tgtgtttcct gacctcaata tttgttataa ggtttgatat gaatcccagg   6300
gggaatctca accctatta cccaacagtc agaaaaatct aagtgtgagg agaacacaat    6360
gtttcaacct tattgttata ataatgcag taagaacagc atggcagaat cgaaggaagc    6420
aagagaccaa gaatgaacct gaaagaagaa tctaagaag aaaaagaag aaatgactgg     6480 tggaaaatag gtatgtttct gttatgctta gcaggaacta ctggaggaat actttggtgg   6540
tatgaaggac tcccacagca acattatata gggttggtgg cgatagggg aagattaaac    6600 ggatctggcc aatcaaatgc tatagaatgc tgggggttcct tcccggggtg tagaccattt    6660
caaaattact tcagttatga gaccaataga agcatgcata tggataataa tactgctaca   6720
ttattagaag ctttaaccaa tataactgct ctataaataa caaaacagaa ttagaaacat   6780
ggaagttagt aaagacttct ggcataactc ctttacctat ttcttctgaa gctaacactg    6840
gactaattag acataagaga gattttggta aagtgcaat agtggcagct attgtagccg    6900
ctactgctat tgctgctagc gctactatgt cttatgttgc tctaactgag gttaacaaaa   6960
taatggaagt acaaaatcat acttttgagg tagaaaatag tactctaaat ggtatggatt    7020
taatagaacg acaaataaag atattatatg ctatgattct tcaaacacat gcagatgttc    7080
aactgttaaa ggaaagacaa caggtagagg agacatttaa tttaattgga tgtatagaaa   7140
gaacacatgt atttttgtcat actggtcatc cctggaatat gtcatgggga catttaaatg   7200
agtcaacaca atgggatgac tgggtaagca aaatggaaga tttaaatcaa gagatactaa   7260
ctacacttca tggagccagg aacaatttgg cacaatccat gataacattc aatacaccag   7320
atagtatagc tcaatttgga aaagaccttt ggagtcatat tggaaattgg attcctggat   7380
tgggagcttc cattataaaa tatatagtga tgttttttgct tatttatttg ttactaacct   7440
cttcgcctaa gatcctcagg gccctctgga aggtgaccag tggtgcaggg tcctccggca   7500
gtcgttacct gaagaaaaaa ttccatcaca aacatgcatc gcgagaagac acctgggacc   7560
aggcccaaca caacatacac ctagcaggcg tgaccggtgg atcaggggac aaatactaca   7620
agcagaagta ctccaggaac gactggaatg gagaatcaga ggagtacaac aggcggccaa   7680
agagctgggt gaagtcaatc gaggcatttg gagagagcta tatttccgag aagaccaaag   7740
gggagatttc tcagcctggg gcggctatca acgagcacaa gaacggctct gggggggaaca   7800 atcctcacca agggtcctta gacctggaga ttcgaagcga aggaggaaac atttatgact   7860
```

```
gttgcattaa agcccaagaa ggaactctcg ctatcccttg ctgtggattt cccttatggc    7920
tattttgggg actagtaatt atagtaggac gcatagcagg ctatggatta cgtggactcg    7980
ctgttataat aaggatttgt attagaggct taaatttgat atttgaaata atcagaaaaa    8040
tgcttgatta tattggaaga gctttaaatc ctggcacatc tcatgtatca atgcctcagt    8100
atgtttagaa aaacaagggg ggaactgtgg ggttttatg aggggtttta taaatgatta    8160
taagagtaaa aagaaagttg ctgatgctct cataaccttg tataacccaa aggactagct    8220
catgttgcta ggcaactaaa ccgcaataac cgcatttgtg acgcgagttc cccattggtg    8280
acgcgttaac ttcctgtttt tacagtatat aagtgcttgt attctgacaa ttgggcactc    8340
agattctgcg gtctgagtcc cttctctgct gggctgaaaa ggcctttgta ataaatataa    8400
ttctctactc agtccctgtc tctagtttgt ctgttcgaga tcctacagag ctcatgcctt    8460
ggcgtaatca tggtcatagc tgtttcctgt gtgaaattgt tatccgctca caattccaca    8520
caacatacga gccggaagca taaagtgtaa agcctgggt gcctaatgag tgagctaact    8580
cacattaatt gcgttgcgct cactgcccgc tttccagtcg ggaaacctgt cgtgccagct    8640
gcattaatga atcggccaac gcgcggggag aggcggtttg cgtattgggc gctcttccgc    8700
ttcctcgctc actgactcgc tgcgctcggt cgttcggctg cggcgagcgg tatcagctca    8760
ctcaaaggcg gtaatacggt tatccacaga atcaggggat aacgcaggaa agaacatgtg    8820
agcaaaaggc cagcaaaagg ccaggaaccg taaaaaggcc gcgttgctgg cgttttttcca   8880 taggctccgc cccctgacg agcatcacaa aaatcgacgc tcaagtcaga ggtggcgaaa    8940
cccgacagga ctataaagat accaggcgtt tccccctgga agctccctcg tgcgctctcc    9000
tgttccgacc ctgccgctta ccggatacct gtccgccttt ctcccttcgg gaagcgtggc    9060
gctttctcat agctcacgct gtaggtatct cagttcggtg taggtcgttc gctccaagct    9120
gggctgtgtg cacgaacccc ccgttcagcc cgaccgctgc gccttatccg gtaactatcg    9180
tcttgagtcc aacccggtaa gacacgactt atcgccactg gcagcagcca ctggtaacag    9240
gattagcaga gcgaggtatg taggcggtgc tacagagttc ttgaagtggt ggcctaacta    9300
cggctacact agaaggacag tatttggtat ctgcgctctg ctgaagccag ttaccttcgg    9360
aaaaagagtt ggtagctctt gatccggcaa acaaaccacc gctggtagcg gtggtttttt    9420
tgtttgcaag cagcagatta cgcgcagaaa aaaaggatct caagaagatc ctttgatctt    9480
ttctacgggg tctgacgctc agtggaacga aaactcacgt taagggattt tggtcatgag    9540
attatcaaaa aggatcttca cctagatcct ttaaattaa aatgaagtt ttaaatcaat    9600 ctaaagtata tatgagtaaa cttggtctga cagttaccaa tgcttaatca gtgaggcacc    9660
tatctcagcg atctgtctat ttcgttcatc catagttgcc tgactccccg tcgtgtagat    9720
aactacgata cgggagggct taccatctgg ccccagtgct gcaatgatac cgcgagaccc    9780
acgctcaccg gctccagatt tatcagcaat aaaccagcca gccggaaggg ccgagcgcag    9840
aagtggtcct gcaactttat ccgcctccat ccagtctatt aattgttgcc gggaagctag    9900
agtaagtagt tcgccagtta atagtttgcg caacgttgtt gccattgcta caggcatcgt    9960
ggtgtcacgc tcgtcgtttg gtatggcttc attcagctcc ggttcccaac gatcaaggcg   10020
agttacatga tcccccatgt tgtgcaaaaa agcggttagc tccttcggtc ctccgatcgt   10080
tgtcagaagt aagttggccg cagtgttatc actcatggtt atggcagcac tgcataattc   10140
tcttactgtc atgccatccg taagatgctt ttctgtgact ggtgagtact caaccaagtc   10200
attctgagaa tagtgtatgc ggcgaccgag ttgctcttgc ccggcgtcaa tacgggataa   10260
```

-continued taccgcgcca catagcagaa ctttaaaagt gctcatcatt ggaaaacgtt cttcggggcg 10320
aaaactctca aggatcttac cgctgttgag atccagttcg atgtaaccca ctcgtgcacc 10380
caactgatct tcagcatctt ttactttcac cagcgtttct gggtgagcaa aaacaggaag 10440
gcaaaatgcc gcaaaaaagg gaataagggc gacacggaaa tgttgaatac tcatactctt 10500
cctttttcaa tattattgaa gcatttatca gggttattgt ctcatgagcg gatacatatt 10560
tgaatgtatt tagaaaaata aacaaatagg ggttccgcgc acatttcccc gaaaagtgcc 10620
acctaaattg taagcgttaa tattttgtta aaattcgcgt taaatttttg ttaaatcagc 10680
tcatttttta accaataggc cgaaatcggc aaaatccctt ataaatcaaa agaatagacc 10740
gagatagggt tgagtgttgt tccagtttgg aacaagagtc cactattaaa gaacgtggac 10800
tccaacgtca aagggcgaaa aaccgtctat cagggcgatg gcccactacg tgaaccatca 10860
ccctaatcaa gttttttggg gtcgaggtgc cgtaaagcac taaatcggaa ccctaaaggg 10920
agcccccgat ttagagcttg acggggaaag ccaacctggc ttatcgaaat taatacgact 10980
cactataggg agaccggc 10998

<210> SEQ ID NO 4
<211> LENGTH: 10448
<212> TYPE: DNA
<213> ORGANISM: Equine Infectious Anemia Virus

<400> SEQUENCE: 4
gtcaccaagt tcgaccctga cctggacttg gaccacccgg gcttctcgga ccaggtgtac 60
cgccagcgca ggaagctgat tgctgagatc gccttccagt acaggcacgg cgacccgatt 120
ccccgtgtgg agtacaccgc cgaggagatt gccacctgga aggaggtcta caccacgctg 180
aagggcctct acgccacgca cgcctgcggg gagcacctgg aggcctttgc tttgctggag 240
cgcttcagcg gctaccggga agacaatatc ccccagctgg aggacgtctc ccgcttcctg 300
aaggagcgca cgggcttcca gctgcggcct gtggccggcc tgctgtccgc ccgggacttc 360
ctggccagcc tggccttccg cgtgttccag tgcacccagt atatccgcca cgcgtcctcg 420
cccatgcact cccctgagcc ggactgctgc cacgagctgc tggggcacgt gcccatgctg 480
gccgaccgca ccttcgcgca gttctcgcag gacattggcc tggcgtccct gggggcctcg 540
gatgaggaaa ttgagaagct gtccacgctg tcatggttca cggtggagtt cgggctgtgt 600
aagcagaacg gggaggtgaa ggcctatggt gccgggctgc tgtcctccta cggggagctc 660
ctgcactgcc tgtctgagga gcctgagatt cgggccttcg accctgaggc tgcggccgtg 720
cagccctacc aagaccagac gtaccagtca gtctacttcg tgtctgagag cttcagtgac 780
gccaaggaca agctcaggag ctatgcctca cgcatccagc gccccttctc cgtgaagttc 840
gacccgtaca cgctggccat cgacgtgctg gacagccccc aggccgtgcg gcgctccctg 900
gagggtgtcc aggatgagct ggacaccctt gcccatgcgc tgagtgccat tggctggaat 960
tctgcagata tcttaaaaca gctctggggt tgtacccacc ccagaggccc acgtggcggc 1020
tagtactccg gtattgcggt acctttgtac gcctgtttta tactcccttc ccccgtaact 1080
tagaagcaca atgtccaagt tcaataggag ggggtacaaa ccagtaccac cacgaacaag 1140
cacttctgtt cccccggtga ggctgtatag gctgtttcca cggctaaaag cggctgatcc 1200
gttatccgct catgtacttc gagaagccta gtatcacctt ggaatcttcg atgcgttgcg 1260
ctcaacactc aaccccagag tgtagcttag gtcgatgagt ctggacgttc ctcaccggcg 1320

```
acgtggtcc aggctgcgtt ggcggcctac ctgtggccca agccacaggg acgctagttg    1380
tgaacaaggt gtgaagagcc tattgagcta cctgagagtc ctccggcccc tgaatgcggc    1440
taatcctaac cacggagcag gcagtggcaa tccagcgacc agcctgtcgt aacgcgcaag    1500
ttcgtggcgg aaccgactac tttgggtgtc cgtgtttcct tttatttta caatggctgc    1560 ttatggtgac aatcattgat tgttatcata agcaaattg gattggccat ccggtgagaa    1620
tttgattatt aaattactct cttgttggga ttgctccttt gaaatcttgt gcactcacac    1680
ctattggaat tacctcattg ttaaacgcgt ctagctagcg tttaaactta agcttggtac    1740
cgagctcgga tctgccacca tggactacaa ggacgacgat gacgagaagg gccctgtgcg    1800
ggcaccggcg gagaagccgc ggggcgccag gtgcagcaat gggttccccg agcgggatcc    1860
gccgcggccc gggcccagca ggccggcgga gaagcccccg cggcccgagg ccaagagcgc    1920
gcagcccgcg gacggctgga agggcgagcg gccccgcagc gaggaggata acgagctgaa    1980
cctccctaac ctggcagccg cctactcgtc catcctgagc tcgctgggcg agaaccccca    2040
gcggcaaggg ctgctcaaga cgccctggag ggcggcctcg gccatgcagt tcttcaccaa    2100
gggctaccag gagaccatct cagatgtcct aaacgatgct atatttgatg aagatcatga    2160
tgagatggtg attgtgaagg acatagacat gttttccatg tgtgagcatc acttggttcc    2220
atttgttgga aaggtccata ttggttatct tcctaacaag caagtccttg gcctcagcaa    2280
acttgcgagg attgtagaaa tctatagtag aagactacaa gttcaggagc gccttacaaa    2340
acaaattgct gtagcaatca cggaagcctt gcggcctgct ggagtcgggg tagtggttga    2400
agcaacacac atgtgtatgg taatgcgagg tgtacagaaa atgaacagca aaactgtgac    2460
cagcacaatg ttgggtgtgt ccgggaggga tccaaagact cgggaagagt tcctgactct    2520
cattaggagc tgaaagcttc gatcactagt gaattcgcgg ccgctcgagg ggggcccgg    2580 tacccagctt tgttcccctt tagtgagggt taattgcgcg ggaagtattt atcactaatc    2640
aagcacaagt aatacatgag aaactttttac tacagcaagc acaatcctcc aaaaaatttt    2700 gttttttacaa aatccctggt gaacatgatt ggaagggacc tactagggtg ctgtggaagg    2760
gtgatggtgc agtagtagtt aatgatgaag gaaagggaat aattgctgta ccattaacca    2820
ggactaagtt actaataaaa ccaaattgag tattgttgca ggaagcaaga cccaactacc    2880
attgtcagct gtgtttcctg acctcaatat ttgttataag gtttgatatg aatcccaggg    2940
ggaatctcaa cccctattac ccaacagtca gaaaaatcta agtgtgagga gaacacaatg    3000
tttcaacctt attgttataa taatgacagt aagaacagca tggcagaatc gaaggaagca    3060
agagaccaag aatgaacctg aaagaagaat ctaaagaaga aaaagaaga aatgactggt    3120 ggaaaatagg tatgttttctg ttatgcttag caggaactac tggaggaata ctttggtggt    3180
atgaaggact cccacagcaa cattatatag ggttggtggc ataggggga agattaaacg    3240 gatctggcca atcaaatgct atagaatgct ggggttcctt cccggggtgt agaccatttc    3300
aaaattactt cagttatgag accaatagaa gcatgcatat ggataataat actgctacat    3360
tattagaagc tttaaccaat ataactgctc tataaataac aaaacagaat tagaaacatg    3420
gaagttagta aagacttctg gcataactcc tttacctatt tcttctgaag ctaacactgg    3480
actaattaga cataagagag attttggtat aagtgcaata gtggcagcta ttgtagccgc    3540
tactgctatt gctgctagcg ctactatgtc ttatgttgct ctaactgagg ttaacaaaat    3600 aatgaagta caaaatcata cttttgaggt agaaaatagt actctaaatg gtatggattt    3660
aatagaacga caaataaaga tattatatgc tatgattctt caaacacatg cagatgttca    3720
```

```
actgttaaag gaaagacaac aggtagagga gacatttaat ttaattggat gtatagaaag    3780
aacacatgta ttttgtcata ctggtcatcc ctggaatatg tcatggggac atttaaatga    3840
gtcaacacaa tgggatgact gggtaagcaa aatggaagat ttaaatcaag agatactaac    3900
tacacttcat ggagccagga acaatttggc acaatccatg ataacattca atacaccaga    3960
tagtatagct caatttggaa aagacctttg gagtcatatt ggaaattgga ttcctggatt    4020
gggagcttcc attataaaat atatagtgat gttttttgctt atttatttgt tactaacctc    4080
ttcgcctaag atcctcaggg ccctctggaa ggtgaccagt ggtgcagggt cctccggcag    4140
tcgttacctg aagaaaaaat tccatcacaa acatgcatcg cgagaagaca cctgggacca    4200
ggcccaacac aacatacacc tagcaggcgt gaccggtgga tcaggggaca aatactacaa    4260
gcagaagtac tccaggaacg actggaatgg agaatcagag gagtacaaca ggcggccaaa    4320
gagctgggtg aagtcaatcg aggcatttgg agagagctat atttccgaga agaccaaagg    4380
ggagatttct cagcctgggg cggctatcaa cgagcacaag aacggctctg gggggaacaa    4440
tcctcaccaa gggtccttag acctggagat tcgaagcgaa ggaggaaaca tttatgactg    4500
ttgcattaaa gcccaagaag gaactctcgc tatcccttgc tgtggatttc ccttatggct    4560
attttgggga ctagtaatta tagtaggacg catagcaggc tatggattac gtggactcgc    4620
tgttataata aggatttgta ttagaggctt aaatttgata tttgaaataa tcagaaaaat    4680
gcttgattat attggaagag ctttaaatcc tggcacatct catgtatcaa tgcctcagta    4740
tgtttagaaa acaaggggg gaactgtggg gttttttatga ggggttttat aaatgattat    4800
aagagtaaaa agaaagttgc tgatgctctc ataaccttgt ataacccaaa ggactagctc    4860
atgttgctag gcaactaaac cgcaataacc gcatttgtga cgcgagttcc ccattggtga    4920
cgcgttaact tcctgtttttt acagtatata agtgcttgta ttctgacaat tgggcactca    4980
gattctgcgg tctgagtccc ttctctgctg ggctgaaaag gcctttgtaa taatataat    5040 tctctactca gtccctgtct ctagtttgtc tgttcgagat cctacagagc tcatgccttg    5100
gcgtaatcat ggtcatagct gtttcctgtg tgaaattgtt atccgctcac aattccacac    5160
aacatacgag ccggaagcat aaagtgtaaa gcctggggtg cctaatgagt gagctaactc    5220
acattaattg cgttgcgctc actgcccgct ttccagtcgg gaaacctgtc gtgccagctg    5280
cattaatgaa tcggccaacg cgcggggaga ggcggtttgc gtattgggcg ctcttccgct    5340
tcctcgctca ctgactcgct gcgctcggtc gttcggctgc ggcgagcggt atcagctcac    5400
tcaaaggcgg taatacggtt atccacagaa tcaggggata acgcaggaaa gaacatgtga    5460
gcaaaaggcc agcaaaaggc caggaaccgt aaaaaggccg cgttgctggc gtttttccat    5520
aggctccgcc cccctgacga gcatcacaaa aatcgacgct caagtcagag gtggcgaaac    5580
ccgacaggac tataaagata ccaggcgttt cccctggaa gctccctcgt gcgctctcct    5640
gttccgaccc tgccgcttac cggatacctg tccgcctttc tcccttcggg aagcgtggcg    5700
ctttctcata gctcacgctg taggtatctc agttcggtgt aggtcgttcg ctccaagctg    5760
ggctgtgtgc acgaaccccc cgttcagccc gaccgctgcg ccttatccgg taactatcgt    5820
cttgagtcca acccggtaag acacgactta tcgccactgg cagcagccac tggtaacagg    5880
attagcagag cgaggtatgt aggcggtgct acagagttct tgaagtggtg gcctaactac    5940
ggctacacta agaggacagt atttggtatc tgcgctctgc tgaagccagt taccttcgga    6000
aaaagagttg gtagctcttg atccggcaaa caaaccaccg ctggtagcgg tggtttttt    6060
```

```
gtttgcaagc agcagattac gcgcagaaaa aaaggatctc aagaagatcc tttgatcttt     6120
tctacggggt ctgacgctca gtggaacgaa aactcacgtt aagggatttt ggtcatgaga     6180
ttatcaaaaa ggatcttcac ctagatcctt ttaaattaaa aatgaagttt taaatcaatc     6240
taaagtatat atgagtaaac ttggtctgac agttaccaat gcttaatcag tgaggcacct     6300
atctcagcga tctgtctatt tcgttcatcc atagttgcct gactccccgt cgtgtagata     6360
actacgatac gggagggctt accatctggc cccagtgctg caatgatacc gcgagaccca     6420
cgctcaccgg ctccagattt atcagcaata accagccag ccggaagggc cgagcgcaga     6480
agtggtcctg caactttatc cgcctccatc cagtctatta attgttgccg ggaagctaga     6540
gtaagtagtt cgccagttaa tagtttgcgc aacgttgttg ccattgctac aggcatcgtg     6600
gtgtcacgct cgtcgtttgg tatggcttca ttcagctccg gttcccaacg atcaaggcga     6660
gttacatgat cccccatgtt gtgcaaaaaa gcggttagct ccttcggtcc tccgatcgtt     6720
gtcagaagta agttggccgc agtgttatca ctcatggtta tggcagcact gcataattct     6780
cttactgtca tgccatccgt aagatgcttt tctgtgactg gtgagtactc aaccaagtca     6840
ttctgagaat agtgtatgcg gcgaccgagt tgctcttgcc cggcgtcaat acgggataat     6900
accgcgccac atagcagaac tttaaaagtg ctcatcattg gaaaacgttc ttcggggcga     6960
aaactctcaa ggatcttacc gctgttgaga tccagttcga tgtaacccac tcgtgcaccc     7020
aactgatctt cagcatcttt tactttcacc agcgtttctg ggtgagcaaa aacaggaagg     7080
caaaatgccg caaaaaaggg aataagggcg cacggaaat gttgaatact catactcttc     7140 cttttttcaat attattgaag catttatcag ggttattgtc tcatgagcgg atacatattt     7200
gaatgtattt agaaaaataa acaaataggg gttccgcgca catttccccg aaaagtgcca     7260
cctaaattgt aagcgttaat attttgttaa aattcgcgtt aaattttgt taaatcagct     7320 cattttttaa ccaataggcc gaaatcggca aaatccctta taaatcaaaa gaatagaccg     7380
agatagggtt gagtgttgtt ccagtttgga acaagagtcc actattaaag aacgtggact     7440
ccaacgtcaa agggcgaaaa accgtctatc agggcgatgg cccactacgt gaaccatcac     7500
cctaatcaag ttttttgggg tcgaggtgcc gtaaagcact aaatcggaac cctaaaggga     7560
gcccccgatt tagagcttga cggggaaagc caacctggct tatcgaaatt aatacgactc     7620
actataggga gaccggcaga tcttgaataa taaaatgtgt gtttgtccga aatacgcgtt     7680
ttgagatttc tgtcgccgac taaattcatg tcgcgcgata gtggtgttta tcgccgatag     7740
agatggcgat attggaaaaa ttgatatttg aaaatatggc atattgaaaa tgtcgccgat     7800
gtgagtttct gtgtaactga tatcgccatt tttccaaaag tgatttttgg gcatacgcga     7860
tatctggcga tagcgcttat atcgtttacg ggggatggcg atagacgact tggtgacttt     7920
gggcgattct gtgtgtcgca aatatcgcag tttcgatata ggtgacagac gatatgaggc     7980
tatatcgccg atagaggcga catcaagctg gcacatggcc aatgcatatc gatctataca     8040
ttgaatcaat attggccatt agccatatta ttcattggtt atatagcata aatcaatatt     8100
ggctattggc cattgcatac gttgtatcca tatcgtaata tgtacattta tattggctca     8160
tgtccaacat taccgccatg ttgacattga ttattgacta gttattaata gtaatcaatt     8220
acggggtcat tagttcatag cccatatatg gagttccgcg ttacataact tacggtaaat     8280
ggcccgcctg gctgaccgcc caacgacccc gcccattga cgtcaataat gacgtatgtt     8340
cccatagtaa cgccaatagg gactttccat tgacgtcaat gggtggagta tttacggtaa     8400
actgcccact tggcagtaca tcaagtgtat catatgccaa gtccgccccc tattgacgtc     8460
```

-continued

```
aatgacggta aatggcccgc ctggcattat gcccagtaca tgaccttacg ggactttcct      8520
acttggcagt acatctacgt attagtcatc gctattacca tggtgatgcg gttttggcag      8580
tacaccaatg ggcgtggata gcggtttgac tcacggggat ttccaagtct ccaccccatt      8640
gacgtcaatg ggagtttgtt ttggcaccaa atcaacggg actttccaaa atgtcgtaac       8700
aactgcgatc gcccgccccg ttgacgcaaa tgggcggtag gcgtgtacgg tgggaggtct      8760
atataagcag agctcgttta gtgaaccggg cactcagatt ctgcggtctg agtcccttct      8820
ctgctgggct gaaaaggcct ttgtaataaa tataattctc tactcagtcc ctgtctctag      8880
tttgtctgtt cgagatccta cagttggcgc ccgaacaggg acctgagagg ggcgcagacc      8940
ctacctgttg aacctggctg atcgtaggat ccccgggaca gcaggagaga acttacagaa      9000
gtcttctgga ggtgttcctg gccagaacac aggaggacag gtaagattgg gagacccttt      9060
gacattggag caaggcgctc aagaagttag agaaggtgac ggtacaaggg tctcagaaat      9120
taactactgg taactgtaat tgggcgctaa gtctagtaga cttatttcat gataccaact      9180
ttgtaaaaga aaaggactgg cagctgaggg atgtcattcc attgctggaa gatgtaactc      9240
agacgctgtc aggacaagaa agagaggcct ttgaaagaac atggtgggca atttctgctg      9300
taaagatggg cctccagatt aataatgtag tagatggaaa ggcatcattc cagctcctaa      9360
gagcgaaata tgaaagaag actgctaata aaaagcagtc tgagccctct aagaatatc       9420 tctagaacta gtggatctcc cgatccccta tggtcgactc tcagtacaat ctgctctgat      9480
gccgcatagt taagccagta tctgctccct gcttgtgtgt tggaggtcgc tgagtagtgc      9540
gcgagcaaaa tttaagctac aacaaggcaa ggcttgaccg acaattgcat gaagaatctg      9600
cttagggtta ggcgttttgc gctgcttcgc gatgtacggg ccagatatac gcgttgacat      9660
tgattattga ctagttatta atagtaatca attacggggt cattagttca tagcccatat      9720
atggagttcc gcgttacata acttacggta atggcccgc ctggctgacc gcccaacgac       9780
ccccgcccat tgacgtcaat aatgacgtat gttcccatag taacgccaat agggactttc      9840
cattgacgtc aatgggtgga ctatttacg taaactgccc acttggcagt acatcaagtg       9900
tatcatatgc caagtacgcc ccctattgac gtcaatgacg gtaaatggcc cgcctggcat      9960
tatgcccagt acatgacctt atgggacttt cctacttggc agtacatcta cgtattagtc     10020
atcgctatta ccatggtgat gcggttttgg cagtacatca atgggcgtgg atagcggttt     10080
gactcacggg gatttccaag tctccacccc attgacgtca atgggagttt gttttggcac     10140
caaaatcaac gggactttcc aaaatgtcgt aacaactccg ccccattgac gcaaatgggc     10200
ggtaggcgtg tacggtggga ggtctatata agcagagctc tctggctaac tagagaaccc     10260
actgcttact ggcttatcga aattaatacg actcactata gggagaccca agctggctag    10320
cgtttaaact taagcttggt accgagctcg gatccgccac catggaacaa aaactcatct     10380
cagaagagga tctgaaggtc ccctggttcc caagaaaagt gtcagagctg acaagtgtc      10440 atcacctg                                                               10448
```

<210> SEQ ID NO 5
<211> LENGTH: 11058
<212> TYPE: DNA
<213> ORGANISM: Equine Infectious Anemia Virus

<400> SEQUENCE: 5

```
tacgactcac tatagggaga cccaagctgg ctagcgttta aacttaagct tggtaccgag        60
```

| | |
|---|---|
| ctcggatctg ccaccatgta ccctacgac gtgcccgact acgccaacgc aagtgaattc | 120 |
| cgaaggagag ggaaggagat ggtggattac gtggccaact acatggaagg cattgaggga | 180 |
| cgccaggtct accctgacgt ggagcccggg tacctgcggc cgctgatccc tgccgctgcc | 240 |
| cctcaggagc cagacacgtt tgaggacatc atcaacgacg ttgagaagat aatcatgcct | 300 |
| ggggtgacgc actggcacag cccctacttc tcgcctact tccccactgc cagctcgtac | 360 |
| ccggccatgc ttgcggacat gctgtgcggg gccattggct gcatcggctt ctcctgggcg | 420 |
| gcaagcccag catgcacaga gctggagact gtgatgatgg actggctcgg aagatgctg | 480 |
| gaactaccaa aggcattttt gaatgagaaa gctggagaag ggaggagt gatccaggga | 540 |
| agtgccagtg aagccaccct ggtggccctg ctggccgctc ggaccaaagt gatccatcgg | 600 |
| ctgcaggcag cgtccccaga gctcacacag ccgctatca tggagaagct ggtggcttac | 660 |
| tcatccgatc aggcacactc ctcagtggaa agagctgggt taattggtgg agtgaaatta | 720 |
| aaagccatcc cctcagatgg caacttcgcc atgcgtgcgc tgccctgca ggaagccctg | 780 |
| gagagagaca aagcggctgg cctgattcct ttctttatgg ttgccaccct ggggaccaca | 840 |
| acatgctgct cctttgacaa tctcttagaa gtcggtccta tctgcaacaa ggaagacata | 900 |
| tggctgcacg ttgatgcagc ctacgcaggc agtgcattca tctgccctga gttccggcac | 960 |
| cttctgaatg gagtggagtt tgcagattca ttcaactta atccccacaa atggctattg | 1020 |
| gtgaattttg actgttctgc catgtgggtg aaaagagaa cagacttaac gggagccttt | 1080 |
| agactggacc ccacttacct gaagcacagc catcaggatt cagggcttat cactgactac | 1140 |
| cggcattggc agataccact gggcagaaga tttcgctctt tgaaaatgtg gtttgtattt | 1200 |
| aggatgtatg gagtcaaagg actgcaggct tatatccgca agcatgtcca gctgtcccat | 1260 |
| gagtttgagt cactggtgcg ccaggatccc cgctttgaaa tctgtgtgga agtcattctg | 1320 |
| gggcttgtct gctttcggct aaagggttcc aacaaagtga atgaagctct tctgcaaaga | 1380 |
| ataaacagtg ccaaaaaaat ccacttggtt ccatgtcacc tcagggacaa gtttgtcctg | 1440 |
| cgctttgcca tctgttctcg cacggtggaa tctgcccatg tgcagcgggc ctgggaacac | 1500 |
| atcaaagagc tggcggccga cgtgctgcga gcagagaggg agtagaagct tcgatcacta | 1560 |
| gtgaattctg cagatgggct gcaggaattc tgatcacgcc cctctccctc ccccccccct | 1620 |
| aacgttactg gccgaagccg cttggaataa ggccggtgtg cgtttgtcta tatgttattt | 1680 |
| tccaccatat tgccgtcttt tggcaatgtg agggcccgga aacctggccc tgtcttcttg | 1740 |
| acgagcattc ctagggtct ttcccctctc gccaaaggaa tgcaaggtct gttgaatgtc | 1800 |
| gtgaaggaag cagttcctct ggaagcttct tgaagacaaa caacgtctgt agcgaccctt | 1860 |
| tgcaggcagc ggaaccccc acctggcgac aggtgcctct gcggccaaaa gccacgtgta | 1920 |
| taagatacac ctgcaaaggc ggcacaaccc cagtgccacg ttgtgagttg atagttgtg | 1980 |
| gaaagagtca aatggctctc ctcaagcgta ttcaacaagg gctgaagga tgcccagaag | 2040 |
| gtacccatt gtatgggatc tgatctgggg cctcggtgca catgctttac atgtgtttag | 2100 |
| tcgaggttaa aaaacgtcta ggccccccga accacgggga cgtggttttc ctttgaaaaa | 2160 |
| cacgatgata agcttgccac aaccatggaa caaaaactca tctcagaaga ggatctgaag | 2220 |
| gtccctggt tccaagaaa agtgtcagag ctggacaagt gtcatcacct ggtcaccaag | 2280 |
| ttcgaccctg acctggactt ggaccacccg ggcttctcgg accaggtgta ccgccagcgc | 2340 |
| aggaagctga ttgctgagat cgccttccag tacaggcacg cgacccgat tcccgtgtg | 2400 |
| gagtacaccg ccgaggagat tgccacctgg aaggaggtct acaccacgct gaagggcctc | 2460 |

```
tacgccacgc acgcctgcgg ggagcacctg gaggcctttg ctttgctgga gcgcttcagc    2520
ggctaccggg aagacaatat cccccagctg gaggacgtct cccgcttcct gaaggagcgc    2580
acgggcttcc agctgcggcc tgtggccggc ctgctgtccg cccgggactt cctggccagc    2640
ctggccttcc gcgtgttcca gtgcacccag tatatccgcc acgcgtcctc gcccatgcac    2700
tcccctgagc cggactgctg ccacgagctg ctggggcacg tgcccatgct ggccgaccgc    2760
accttcgcgc agttctcgca ggacattggc ctggcgtccc tggggcctc ggatgaggaa    2820 attgagaagc tgtccacgct gtcatggttc acggtggagt tcgggctgtg taagcagaac    2880
ggggaggtga aggcctatgg tgccgggctg ctgtcctcct acggggagct cctgcactgc    2940
ctgtctgagg agcctgagat tcgggccttc gaccctgagg ctgcggccgt gcagccctac    3000
caagaccaga cgtaccagtc agtctacttc gtgtctgaga gcttcagtga cgccaaggac    3060
aagctcagga gctatgcctc acgcatccag cgccccttct ccgtgaagtt cgacccgtac    3120
acgctggcca tcgacgtgct ggacagcccc caggccgtgc ggcgctccct ggagggtgtc    3180
caggatgagc tggacaccct tgcccatgcg ctgagtgcca ttggctagga attctgcaga    3240
tatcttaaaa cagctctggg gttgtaccca ccccagaggc ccacgtggcg gctagtactc    3300
cggtattgcg gtacctttgt acgcctgttt tatactccct tcccccgtaa cttagaagca    3360
caatgtccaa gttcaatagg aggggtaca aaccagtacc accacgaaca agcacttctg    3420
ttcccccggt gaggctgtat aggctgtttc cacggctaaa agcggctgat ccgttatccg    3480
ctcatgtact tcgagaagcc tagtatcacc ttggaatctt cgatgcgttg cgctcaacac    3540
tcaaccccag agtgtagctt aggtcgatga gtctggacgt tcctcaccgg cgacggtggt    3600
ccaggctgcg ttggcggcct acctgtggcc caaagccaca ggacgctagt tgtgaacaag    3660
gtgtgaagag cctattgagc tacctgagag tcctccggcc cctgaatgcg gctaatccta    3720
accacggagc aggcagtggc aatccagcga ccagcctgtc gtaacgcgca agttcgtggc    3780
ggaaccgact actttgggtg tccgtgtttc cttttatttt tacaatggct gcttatggtg    3840
acaatcattg attgttatca taaagcaaat tggattggcc atccggtgag aatttgatta    3900
ttaaattact ctcttgttgg gattgctcct ttgaaatctt gtgcactcac acctattgga    3960
attacctcat tgttaaacgc gtctagctag cgtttaaact taagcttggt accgagctcg    4020
gatctgccac catggactac aaggacgacg atgacgagaa gggccctgtg cgggcaccgg    4080
cggagaagcc gcgggcgcc aggtgcagca atgggttccc cgagcgggat ccgccgcggc    4140
ccgggcccag caggccggcg gagaagcccc gcggcccga ggccaagagc gcgcagcccg    4200
cggacggctg gaagggcgag cggccccgca gcgaggagga taacgagctg aacctcccta    4260
acctggcagc cgcctactcg tccatcctga gctcgctggg cgagaacccc cagcggcaag    4320
ggctgctcaa gacgccctgg agggcggcct cggccatgca gttcttcacc aagggctacc    4380
aggagaccat ctcagatgtc ctaaacgatg ctatatttga tgaagatcat gatgagatgg    4440
tgattgtgaa ggacatagac atgttttcca tgtgtgagca tcacttggtt ccatttgttg    4500
gaaaggtcca tattggttat cttcctaaca agcaagtcct tggcctcagc aaacttgcga    4560
ggattgtaga aatctatagt agaagactac aagttcagga gcgccttaca aaacaaattg    4620
ctgtagcaat cacggaagcc ttgcggcctg ctggagtcgg ggtagtggtt gaagcaacac    4680
acatgtgtat ggtaatgcga ggtgtacaga aaatgaacag caaaactgtg accagcacaa    4740
tgttgggtgt gttccgggag gatccaaaga ctcgggaaga gttcctgact ctcattagga    4800
```

```
gctgaaagct tcgatcacta gtgaattcgc ggccgctcga ggggggggccc ggtacccagc    4860 ttttgttccc tttagtgagg gttaattgcg cgggaagtat ttatcactaa tcaagcacaa    4920
gtaatacatg agaaactttt actacagcaa gcacaatcct ccaaaaaatt ttgtttttac    4980
aaaatccctg gtgaacatga ttggaaggga cctactaggg tgctgtggaa gggtgatggt    5040
gcagtagtag ttaatgatga aggaaaggga ataattgctg taccattaac caggactaag    5100
ttactaataa aaccaaattg agtattgttg caggaagcaa gacccaacta ccattgtcag    5160
ctgtgtttcc tgacctcaat atttgttata aggtttgata tgaatcccag ggggaatctc    5220 aaccectatt acccaacagt cagaaaaatc taagtgtgag gagaacacaa tgtttcaacc    5280
ttattgttat aataatgaca gtaagaacag catggcagaa tcgaaggaag caagagacca    5340
agaatgaacc tgaaagaaga atctaaagaa gaaaaaagaa gaaatgactg gtggaaaata    5400
ggtatgtttc tgttatgctt agcaggaact actggaggaa tactttggtg gtatgaagga    5460
ctcccacagc aacattatat agggttggtg gcgataggggg gaagattaaa cggatctggc    5520
caatcaaatg ctatagaatg ctggggttcc ttcccggggt gtagaccatt tcaaaattac    5580
ttcagttatg agaccaatag aagcatgcat atggataata atactgctac attattagaa    5640
gctttaacca atataactgc tctataaata acaaaacaga attagaaaca tggaagttag    5700
taaagacttc tggcataact cctttaccta tttcttctga agctaacact ggactaatta    5760
gacataagag agattttggt ataagtgcaa tagtggcagc tattgtagcc gctactgcta    5820
ttgctgctag cgctactatg tcttatgttg ctctaactga ggttaacaaa ataatggaag    5880
tacaaaatca tacttttgag gtagaaaata gtactctaaa tggtatggat ttaatagaac    5940
gacaaataaa gatattatat gctatgattc ttcaaacaca tgcagatgtt caactgttaa    6000
aggaaagaca acaggtagag gagacattta atttaattgg atgtatagaa agaacacatg    6060
tattttgtca tactggtcat ccctggaata tgtcatgggg acatttaaat gagtcaacac    6120
aatgggatga ctgggtaagc aaaatggaag atttaaatca agagatacta actacacttc    6180
atggagccag gaacaatttg gcacaatcca tgataacatt caatacacca gatagtatag    6240
ctcaatttgg aaaagacctt tggagtcata ttggaaattg gattcctgga ttgggagctt    6300
ccattataaa atatatagtg atgttttttgc ttatttattt gttactaacc tcttcgccta    6360
agatcctcag ggccctctgg aaggtgacca gtggtgcagg gtcctccggc agtcgttacc    6420
tgaagaaaaa attccatcac aaacatgcat cgcgagaaga cacctgggac caggcccaac    6480
acaacataca cctagcaggc gtgaccggtg gatcaggggga caaatactac aagcagaagt    6540
actccaggaa cgactggaat ggagaatcag aggagtacaa caggcggcca aagagctggg    6600
tgaagtcaat cgaggcattt ggagagagct atatttccga gaagaccaaa ggggagattt    6660
ctcagcctgg ggcggctatc aacgagcaca gaacggctc tgggggaaac aatcctcacc    6720
aagggtcctt agacctggag attcgaagcg aaggaggaaa catttatgac tgttgcatta    6780 agcccaaga aggaactctc gctatccctt gctgtggatt tcccttatgg ctattttggg    6840
gactagtaat tatagtagga cgcatagcag gctatgatt acgtggactc gctgttataa    6900
taaggatttg tattagaggc ttaaatttga tatttgaaat aatcagaaaa atgcttgatt    6960
atattggaag agctttaaat cctggcacat ctcatgtatc aatgcctcag tatgtttaga    7020
aaacaagggg gggaactgtg gggtttttat gaggggtttt ataaatgatt ataagagtaa    7080
aaagaaagtt gctgatgctc tcataaacctt gtataaccca aaggactagc tcatgttgct    7140
aggcaactaa accgcaataa ccgcatttgt gacgcgagtt ccccattggt gacgcgttaa    7200
```

```
cttcctgttt ttacagtata taagtgcttg tattctgaca attgggcact cagattctgc   7260
ggtctgagtc ccttctctgc tgggctgaaa aggcctttgt aataaatata attctctact   7320
cagtccctgt ctctagtttg tctgttcgag atcctacaga gctcatgcct ggcgtaatc    7380 atggtcatag ctgtttcctg tgtgaaattg ttatccgctc acaattccac acaacatacg   7440
agccggaagc ataaagtgta aagcctgggg tgcctaatga gtgagctaac tcacattaat   7500
tgcgttgcgc tcactgcccg ctttccagtc gggaaacctg tcgtgccagc tgcattaatg   7560
aatcggccaa cgcgcgggga gaggcggttt gcgtattggg cgctcttccg cttcctcgct   7620
cactgactcg ctgcgctcgg tcgttcggct gcggcgagcg gtatcagctc actcaaaggc   7680
ggtaatacgg ttatccacag aatcagggga taacgcagga agaacatgt gagcaaaagg    7740 ccagcaaaag gccaggaacc gtaaaaaggc cgcgttgctg gcgtttttcc ataggctccg   7800 ccccctgac gagcatcaca aaatcgacg ctcaagtcag aggtggcgaa acccgacagg     7860
actataaaga taccaggcgt ttccccctgg aagctccctc gtgcgctctc ctgttccgac   7920
cctgccgctt accggatacc tgtccgcctt tctcccttcg ggaagcgtgg cgctttctca   7980
tagctcacgc tgtaggtatc tcagttcggt gtaggtcgtt cgctccaagc tgggctgtgt   8040
gcacgaaccc cccgttcagc ccgaccgctg cgccttatcc ggtaactatc gtcttgagtc   8100
caacccggta agacacgact tatcgccact ggcagcagcc actggtaaca ggattagcag   8160
agcgaggtat gtaggcggtg ctacagagtt cttgaagtgg tggcctaact acggctacac   8220
tagaaggaca gtatttggta tctgcgctct gctgaagcca gttaccttcg gaaaaagagt   8280
tggtagctct tgatccggca aacaaaccac cgctggtagc ggtggttttt tgtttgcaa    8340 gcagcagatt acgcgcagaa aaaaaggatc tcaagaagat cctttgatct tttctacggg   8400
gtctgacgct cagtggaacg aaaactcacg ttaagggatt ttggtcatga gattatcaaa   8460
aaggatcttc acctagatcc ttttaaatta aaaatgaagt tttaaatcaa tctaaagtat   8520
atatgagtaa acttggtctg acagttacca atgcttaatc agtgaggcac ctatctcagc   8580
gatctgtcta tttcgttcat ccatagttgc ctgactcccc gtcgtgtaga taactacgat   8640
acgggagggc ttaccatctg gccccagtgc tgcaatgata ccgcgagacc cacgctcacc   8700
ggctccagat ttatcagcaa taaaccagcc agccggaagg gccgagcgca gaagtggtcc   8760
tgcaacttta tccgcctcca tccagtctat taattgttgc cgggaagcta gagtaagtag   8820
ttcgccagtt aatagtttgc gcaacgttgt tgccattgct acaggcatcg tggtgtcacg   8880
ctcgtcgttt ggtatggctt cattcagctc cggttcccaa cgatcaaggc gagttacatg   8940
atcccccatg ttgtgcaaaa aagcggttag ctccttcggt cctccgatcg ttgtcagaag   9000
taagttggcc gcagtgttat cactcatggt tatggcagca ctgcataatt ctcttactgt   9060
catgccatcc gtaagatgct tttctgtgac tggtgagtac tcaaccaagt cattctgaga   9120
atagtgtatg cggcgaccga gttgctcttg cccggcgtca atacgggata taccgcgcc    9180 acatagcaga actttaaaag tgctcatcat tggaaaacgt tcttcggggc gaaaactctc   9240
aaggatctta ccgctgttga gatccagttc gatgtaaccc actcgtgcac ccaactgatc   9300
ttcagcatct tttactttca ccagcgtttc tgggtgagca aaaacaggaa ggcaaaatgc   9360
cgcaaaaaag ggaataaggg cgacacggaa atgttgaata ctcatactct tcctttttca   9420
atattattga agcatttatc agggttattg tctcatgagc ggatacatat ttgaatgtat   9480
ttagaaaaat aaacaaatag gggttccgcg cacatttccc cgaaaagtgc cacctaaatt   9540
```

```
gtaagcgtta atattttgtt aaaattcgcg ttaaattttt gttaaatcag ctcatttttt      9600
aaccaatagg ccgaaatcgg caaaatccct tataaatcaa agaatagac  cgagataggg      9660 ttgagtgttg ttccagtttg gaacaagagt ccactattaa agaacgtgga ctccaacgtc      9720
aaagggcgaa aaaccgtcta tcagggcgat ggcccactac gtgaaccatc accctaatca      9780
agttttttgg ggtcgaggtg ccgtaaagca ctaaatcgga accctaaagg gagccccga      9840 tttagagctt gacggggaaa gccaacctgg cttatcgaaa ttaatacgac tcactatagg      9900
gagaccggca gatcttgaat aataaaatgt gtgtttgtcc gaaatacgcg ttttgagatt      9960
tctgtcgccg actaaattca gtcgcgcga  tagtggtgtt tatcgccgat agagatggcg    10020
atattggaaa aattgatatt tgaaaatatg gcatattgaa aatgtcgccg atgtgagttt    10080
ctgtgtaact gatatcgcca tttttccaaa agtgattttt gggcatacgc gatatctggc    10140
gatagcgctt atatcgttta cggggggatgg cgatagacga ctttggtgac ttgggcgatt    10200
ctgtgtgtcg caaatatcgc agtttcgata taggtgacag acgatatgag gctatatcgc    10260
cgatagaggc gacatcaagc tggcacatgg ccaatgcata tcgatctata cattgaatca    10320
atattggcca ttagccatat tattcattgg ttatatagca taaatcaata ttggctattg    10380
gccattgcat acgttgtatc catatcgtaa tatgtacatt tatattggct catgtccaac    10440
attaccgcca tgttgacatt gattattgac tagtattaa  tagtaatcaa ttacggggtc    10500
attagttcat agcccatata tggagttccg cgttacataa cttacggtaa atggcccgcc    10560
tggctgaccg cccaacgacc cccgcccatt gacgtcaata atgacgtatg ttcccatagt    10620
aacgccaata gggactttcc attgacgtca atgggtggag tatttacggt aaactgccca    10680
cttggcagta catcaagtgt atcatatgcc aagtccgccc cctattgacg tcaatgacgg    10740
taaatggccc gcctggcatt atgcccagta catgaccta  cgggactttc ctacttggca    10800
gtacatctac gtattagtca tcgctattac catggtgatg cggtttttggc agtacaccaa    10860 tgggcgtgga tagcggttg  actcacgggg atttccaagt ctccacccca ttgacgtcaa    10920 tgggagttg  ttttggcacc aaaatcaacg ggactttcca aaatgtcgta acaactgcga    10980
tcgcccgccc cgttgacgca aatgggcggt aggcgtgtac ggtgggaggt ctatataagc    11040
agagctcgtt tagtgaac                                                   11058
```

<210> SEQ ID NO 6
<211> LENGTH: 50
<212> TYPE: DNA
<213> ORGANISM: Equine Infectious Anemia Virus

<400> SEQUENCE: 6

```
cggatcagat cttgatcact gcaggctctc attacttgta acaaagggag                 50
```

<210> SEQ ID NO 7
<211> LENGTH: 37
<212> TYPE: DNA
<213> ORGANISM: Equine Infectious Anemia Virus

<400> SEQUENCE: 7

```
agctcggatc cctgcagcat gttccaggag gattttg                               37
```

<210> SEQ ID NO 8
<211> LENGTH: 65
<212> TYPE: DNA
<213> ORGANISM: Homo Sapiens

<400> SEQUENCE: 8

```
gcggatccgc caccatggaa aaactcatct cagaagagga tctgcccacc cccgacgcca    60
ccacg                                                                65

<210> SEQ ID NO 9
<211> LENGTH: 25
<212> TYPE: DNA
<213> ORGANISM: Homo Sapiens

<400> SEQUENCE: 9
gaaccgcggg gactgccctc ttacc                                          25

<210> SEQ ID NO 10
<211> LENGTH: 26
<212> TYPE: DNA
<213> ORGANISM: Homo Sapiens

<400> SEQUENCE: 10
ggtaaagagg gcagtccccg cggttc                                         26

<210> SEQ ID NO 11
<211> LENGTH: 35
<212> TYPE: DNA
<213> ORGANISM: Homo Sapiens

<400> SEQUENCE: 11
cgaagcttct agccaatggc actcagcgca tgggc                               35

<210> SEQ ID NO 12
<211> LENGTH: 65
<212> TYPE: DNA
<213> ORGANISM: Homo Sapiens

<400> SEQUENCE: 12
cgagatctgc caccatgtac ccctacgacg tgcccgacta cgccaacgca agtgaattcc    60
gaagg                                                                65

<210> SEQ ID NO 13
<211> LENGTH: 27
<212> TYPE: DNA
<213> ORGANISM: Homo Sapiens

<400> SEQUENCE: 13
cgaagcttct actccctctc tgctcgc                                        27

<210> SEQ ID NO 14
<211> LENGTH: 58
<212> TYPE: DNA
<213> ORGANISM: Homo Sapiens

<400> SEQUENCE: 14
cgagatctgc caccatggac tacaaggacg acgatgacga aagggccct gtgcggcg       58

<210> SEQ ID NO 15
<211> LENGTH: 32
<212> TYPE: DNA
<213> ORGANISM: Homo Sapiens

<400> SEQUENCE: 15
cgaagctttc agctcctaat gagagtcagg aa                                  32

<210> SEQ ID NO 16
```

```
<211> LENGTH: 77
<212> TYPE: DNA
<213> ORGANISM: Homo Sapiens

<400> SEQUENCE: 16
cgaagcttgg atccgccacc atggaacaaa aactcatctc agaagaggat ctgaaggtcc      60
cctggttccc aagaaaa                                                     77

<210> SEQ ID NO 17
<211> LENGTH: 35
<212> TYPE: DNA
<213> ORGANISM: Homo Sapiens

<400> SEQUENCE: 17
cggaattcct agccaatggc actcagcgca tgggc                                 35

<210> SEQ ID NO 18
<211> LENGTH: 250
<212> TYPE: PRT
<213> ORGANISM: Homo Sapiens

<400> SEQUENCE: 18
```

Met Glu Lys Gly Pro Val Arg Ala Pro Ala Glu Lys Pro Arg Gly Ala
1               5                   10                  15

Arg Cys Ser Asn Gly Phe Pro Glu Arg Asp Pro Pro Arg Pro Gly Pro
            20                  25                  30

Ser Arg Pro Ala Glu Lys Pro Pro Arg Pro Glu Ala Lys Ser Ala Gln
        35                  40                  45

Pro Ala Asp Gly Trp Lys Gly Glu Arg Pro Arg Ser Glu Glu Asp Asn
    50                  55                  60

Glu Leu Asn Leu Pro Asn Leu Ala Ala Ala Tyr Ser Ser Ile Leu Ser
65                  70                  75                  80

Ser Leu Gly Glu Asn Pro Gln Arg Gln Gly Leu Leu Lys Thr Pro Trp
                85                  90                  95

Arg Ala Ala Ser Ala Met Gln Phe Phe Thr Lys Gly Tyr Gln Glu Thr
            100                 105                 110

Ile Ser Asp Val Leu Asn Asp Ala Ile Phe Asp Glu Asp His Asp Glu
        115                 120                 125

Met Val Ile Val Lys Asp Ile Asp Met Phe Ser Met Cys Glu His His
    130                 135                 140

Leu Val Pro Phe Val Gly Lys Val His Ile Gly Tyr Leu Pro Asn Lys
145                 150                 155                 160

Gln Val Leu Gly Leu Ser Lys Leu Ala Arg Ile Val Glu Ile Tyr Ser
                165                 170                 175

Arg Arg Leu Gln Val Gln Glu Arg Leu Thr Lys Gln Ile Ala Val Ala
            180                 185                 190

Ile Thr Glu Ala Leu Arg Pro Ala Gly Val Gly Val Val Val Glu Ala
        195                 200                 205

Thr His Met Cys Met Val Met Arg Gly Val Gln Lys Met Asn Ser Lys
    210                 215                 220

Thr Val Thr Ser Thr Met Leu Gly Val Phe Arg Glu Asp Pro Lys Thr
225                 230                 235                 240

Arg Glu Glu Phe Leu Thr Leu Ile Arg Ser
                245                 250

```
<210> SEQ ID NO 19
<211> LENGTH: 753
```

<210> SEQ ID NO 19
<211> LENGTH: 753
<212> TYPE: DNA
<213> ORGANISM: Homo Sapiens

<400> SEQUENCE: 19

```
atggagaagg gccctgtgcg cgccccggcc gagaagccgc gcggcgcccg ctgcagcaat      60
gggttccccg agcgcgaccc gccgcgcccc gggcccagca ggccggccga aagcccccg     120
cgccccgagg ccaagagcgc gcagcccgcg gacggctgga agggcgagcg ccccccgcagc   180
gaggaggaca acgagctgaa cctccctaac ctggccgccg cctactcctc catcctgagc    240
tcgctgggcg agaaccccca gcggcagggg ctgctcaaga cccccctggag ggcggcctcg   300
gccatgcagt tcttccaccaa ggctaccag gagaccatct cagacgtcct gaacgacgct    360
atcttcgacg aagatcacga tgagatggtg atcgtgaagg acatagacat gttctccatg    420
tgcgagcacc acctggtgcc atttgtggga aaggtccata tcggctacct gcctaacaag    480
caggtcctgg gctcagcaa gctggcgagg attgtggaaa tctatagtag aagactacag    540
gttcaggagc gccttaccaa acaaattgct gtggcaatca cggaagcctt gcggcctgct    600
ggagtcgggg tcgtggtgga agcaacacac atgtgtatgg tgatgcgagg tgtacagaaa    660
atgaacagca aaaccgtgac cagcacaatg ctgggtgtgt ccgggagga tccaaagact     720
cgggaagagt tcctgactct catcaggagc tga                                  753
```

<210> SEQ ID NO 20
<211> LENGTH: 250
<212> TYPE: PRT
<213> ORGANISM: Homo Sapiens

<400> SEQUENCE: 20

```
Met Glu Lys Gly Pro Val Arg Ala Pro Ala Glu Lys Pro Arg Gly Ala
1               5                   10                  15

Arg Cys Ser Asn Gly Phe Pro Glu Arg Asp Pro Pro Arg Pro Gly Pro
            20                  25                  30

Ser Arg Pro Ala Glu Lys Pro Pro Arg Pro Glu Ala Lys Ser Ala Gln
        35                  40                  45

Pro Ala Asp Gly Trp Lys Gly Glu Arg Pro Arg Ser Glu Glu Asp Asn
    50                  55                  60

Glu Leu Asn Leu Pro Asn Leu Ala Ala Ala Tyr Ser Ser Ile Leu Ser
65                  70                  75                  80

Ser Leu Gly Glu Asn Pro Gln Arg Gln Gly Leu Leu Lys Thr Pro Trp
                85                  90                  95

Arg Ala Ala Ser Ala Met Gln Phe Phe Thr Lys Gly Tyr Gln Glu Thr
            100                 105                 110

Ile Ser Asp Val Leu Asn Asp Ala Ile Phe Asp Glu Asp His Asp Glu
        115                 120                 125

Met Val Ile Val Lys Asp Ile Asp Met Phe Ser Met Cys Glu His His
    130                 135                 140

Leu Val Pro Phe Val Gly Lys Val His Ile Gly Tyr Leu Pro Asn Lys
145                 150                 155                 160

Gln Val Leu Gly Leu Ser Lys Leu Ala Arg Ile Val Glu Ile Tyr Ser
                165                 170                 175

Arg Arg Leu Gln Val Gln Glu Arg Leu Thr Lys Gln Ile Ala Val Ala
            180                 185                 190

Ile Thr Glu Ala Leu Arg Pro Ala Gly Val Gly Val Val Glu Ala
        195                 200                 205

Thr His Met Cys Met Val Met Arg Gly Val Gln Lys Met Asn Ser Lys
```

```
                210                 215                 220
Thr Val Thr Ser Thr Met Leu Gly Val Phe Arg Glu Asp Pro Lys Thr
225                 230                 235                 240

Arg Glu Glu Phe Leu Thr Leu Ile Arg Ser
                245                 250
```

<210> SEQ ID NO 21
<211> LENGTH: 753
<212> TYPE: DNA
<213> ORGANISM: Homo Sapiens

<400> SEQUENCE: 21

```
atggagaagg gccctgtgcg ggcaccggcg gagaagccgc ggggcgccag gtgcagcaat    60
gggttccccg agcgggatcc gccgcggccc gggcccagca ggccggcgga gaagcccccg   120
cggcccgagg ccaagagcgc gcagcccgcg gacggctgga agggcgagcg gccccgcagc   180
gaggaggata cgagctgaa cctccctaac ctggcagccg cctactcgtc catcctgagc   240
tcgctgggcg agaaccccca gcggcaaggg ctgctcaaga cgccctggag ggcggcctcg   300
gccatgcagt tcttcaccaa gggctaccag gagaccatct cagatgtcct aaacgatgct   360
atatttgatg aagatcatga tgagatggtg attgtgaagg acatagacat gttttccatg   420
tgtgagcatc acttggttcc atttgttgga aaggtccata ttggttatct tcctaacaag   480
caagtccttg gcctcagcaa acttgcgagg attgtagaaa tctatagtag aagactacaa   540
gttcaggagc gccttacaaa acaaattgct gtagcaatca cggaagcctt gcggcctgct   600
ggagtcgggg tagtggttga agcaacacac atgtgtatgg taatgcgagg tgtacagaaa   660
atgaacagca aaactgtgac cagcacaatg ttgggtgtgt ccggggagga tccaaagact   720
cgggaagagt tcctgactct cattaggagc tga                                753
```

<210> SEQ ID NO 22
<211> LENGTH: 338
<212> TYPE: PRT
<213> ORGANISM: Homo Sapiens

<400> SEQUENCE: 22

```
Met Val Lys Val Pro Trp Phe Pro Arg Lys Val Ser Glu Leu Asp Lys
1               5                   10                  15

Cys His His Leu Val Thr Lys Phe Asp Pro Asp Leu Asp Leu Asp His
                20                  25                  30

Pro Gly Phe Ser Asp Gln Val Tyr Arg Gln Arg Lys Leu Ile Ala
            35                  40                  45

Glu Ile Ala Phe Gln Tyr Arg His Gly Asp Pro Ile Pro Arg Val Glu
    50                  55                  60

Tyr Thr Ala Glu Glu Ile Ala Thr Trp Lys Glu Val Tyr Thr Thr Leu
65                  70                  75                  80

Lys Gly Leu Tyr Ala Thr His Ala Cys Gly Glu His Leu Glu Ala Phe
                85                  90                  95

Ala Leu Leu Glu Arg Phe Ser Gly Tyr Arg Glu Asp Asn Ile Pro Gln
            100                 105                 110

Leu Glu Asp Val Ser Arg Phe Leu Lys Glu Arg Thr Gly Phe Gln Leu
        115                 120                 125

Arg Pro Val Ala Gly Leu Leu Ser Ala Arg Asp Phe Leu Ala Ser Leu
    130                 135                 140

Ala Phe Arg Val Phe Gln Cys Thr Gln Tyr Ile Arg His Ala Ser Ser
145                 150                 155                 160
```

```
Pro Met His Ser Pro Glu Pro Asp Cys Cys His Glu Leu Leu Gly His
            165                 170                 175
Val Pro Met Leu Ala Asp Arg Thr Phe Ala Gln Phe Ser Gln Asp Ile
            180                 185                 190
Gly Leu Ala Ser Leu Gly Ala Ser Asp Glu Glu Ile Glu Lys Leu Ser
            195                 200                 205
Thr Leu Tyr Trp Phe Thr Val Glu Phe Gly Leu Cys Lys Gln Asn Gly
    210                 215                 220
Glu Val Lys Ala Tyr Gly Ala Gly Leu Leu Ser Ser Tyr Gly Glu Leu
225                 230                 235                 240
Leu His Cys Leu Ser Glu Glu Pro Glu Ile Arg Ala Phe Asp Pro Glu
            245                 250                 255
Ala Ala Ala Val Gln Pro Tyr Gln Asp Gln Thr Tyr Gln Ser Val Tyr
            260                 265                 270
Phe Val Ser Glu Ser Phe Ser Asp Ala Lys Asp Lys Leu Arg Ser Tyr
    275                 280                 285
Ala Ser Arg Ile Gln Arg Pro Phe Ser Val Lys Phe Asp Pro Tyr Thr
290                 295                 300
Leu Ala Ile Asp Val Leu Asp Ser Pro Gln Ala Val Arg Arg Ser Leu
305                 310                 315                 320
Glu Gly Val Gln Asp Glu Leu Asp Thr Leu Ala His Ala Leu Ser Ala
            325                 330                 335
Ile Gly

<210> SEQ ID NO 23
<211> LENGTH: 1014
<212> TYPE: DNA
<213> ORGANISM: Homo Sapiens

<400> SEQUENCE: 23
atggtgaagg taccctggtt cccaagaaaa gtgtcagagc tggacaagtg tcatcacctg      60
gtcaccaagt tcgaccccga cctggacttg gaccacccag gcttctcgga ccaggtgtac     120
cgccagcgca ggaagctgat cgctgagatc gccttccagt acaggcacgg cgacccgatc     180
ccccgtgtgg agtacaccgc cgaggagatc gccacctgga aggaggtcta caccaccctg     240
aagggcctct acgccaccca cgcctgcggg gagcacctgg aggcctttgc tttgctggag     300
cgcttcagcg gctaccggga agacaacatc ccccagctgg aggacgtctc ccgcttcctg     360
aaggagcgca caggcttcca gctgcggccc gtggccggcc tgctgtccgc ccgggacttc     420
ctggccagcc tggccttccg cgtgttccag tgcacccagt atatccgcca cgcgtcctcg     480
cccatgcact cccctgagcc ggactgctgc acgagctgc tggggcacgt gcccatgctg     540
gccgaccgca ccttcgcgca gttcagccag acatcggcc tggcgtccct ggggccagc      600
gatgaggaaa tcgagaagct gtccactctg tactggttca cggtggagtt cgggctgtgt     660
aagcagaacg gggaggtgaa ggcctatggt gccgggctgc tgtcctccta cggggagctc     720
ctgcactgcc tgtctgagga gcctgagatc cgggccttcg accctgaggc tgcggccgtg     780
cagccctacc aagaccagac gtaccagtca gtctacttcg tgtctgagag cttcagcgac     840
gccaaggaca agctcaggag ctatgccagc cgcatccagc gccccttctc cgtgaagttc     900
gacccgtaca ccctggccat cgacgtgctg gacagccccc aggccgtgcg gcgctccctg     960
gagggtgtcc aggatgagct ggacaccctt gcccatgcgc tgagcgccat cggc         1014
```

<210> SEQ ID NO 24
<211> LENGTH: 338
<212> TYPE: PRT
<213> ORGANISM: Homo Sapiens

<400> SEQUENCE: 24

```
Met Val Lys Val Pro Trp Phe Pro Arg Lys Val Ser Glu Leu Asp Lys
  1               5                  10                  15

Cys His His Leu Val Thr Lys Phe Asp Pro Asp Leu Asp Leu Asp His
             20                  25                  30

Pro Gly Phe Ser Asp Gln Val Tyr Arg Gln Arg Lys Leu Ile Ala
         35                  40                  45

Glu Ile Ala Phe Gln Tyr Arg His Gly Asp Pro Ile Pro Arg Val Glu
 50                  55                  60

Tyr Thr Ala Glu Ile Ala Thr Trp Lys Glu Val Tyr Thr Thr Leu
 65                  70                  75                  80

Lys Gly Leu Tyr Ala Thr His Ala Cys Gly Glu His Leu Glu Ala Phe
                 85                  90                  95

Ala Leu Leu Glu Arg Phe Ser Gly Tyr Arg Glu Asp Asn Ile Pro Gln
            100                 105                 110

Leu Glu Asp Val Ser Arg Phe Leu Lys Glu Arg Thr Gly Phe Gln Leu
            115                 120                 125

Arg Pro Val Ala Gly Leu Leu Ser Ala Arg Asp Phe Leu Ala Ser Leu
        130                 135                 140

Ala Phe Arg Val Phe Gln Cys Thr Gln Tyr Ile Arg His Ala Ser Ser
145                 150                 155                 160

Pro Met His Ser Pro Glu Pro Asp Cys Cys His Glu Leu Leu Gly His
                165                 170                 175

Val Pro Met Leu Ala Asp Arg Thr Phe Ala Gln Phe Ser Gln Asp Ile
            180                 185                 190

Gly Leu Ala Ser Leu Gly Ala Ser Asp Glu Glu Ile Glu Lys Leu Ser
        195                 200                 205

Thr Leu Ser Trp Phe Thr Val Glu Phe Gly Leu Cys Lys Gln Asn Gly
    210                 215                 220

Glu Val Lys Ala Tyr Gly Ala Gly Leu Leu Ser Ser Tyr Gly Glu Leu
225                 230                 235                 240

Leu His Cys Leu Ser Glu Glu Pro Glu Ile Arg Ala Phe Asp Pro Glu
                245                 250                 255

Ala Ala Ala Val Gln Pro Tyr Gln Asp Gln Thr Tyr Gln Ser Val Tyr
            260                 265                 270

Phe Val Ser Glu Ser Phe Ser Asp Ala Lys Asp Lys Leu Arg Ser Tyr
        275                 280                 285

Ala Ser Arg Ile Gln Arg Pro Phe Ser Val Lys Phe Asp Pro Tyr Thr
    290                 295                 300

Leu Ala Ile Asp Val Leu Asp Ser Pro Gln Ala Val Arg Arg Ser Leu
305                 310                 315                 320

Glu Gly Val Gln Asp Glu Leu Asp Thr Leu Ala His Ala Leu Ser Ala
                325                 330                 335

Ile Gly
```

<210> SEQ ID NO 25
<211> LENGTH: 1017
<212> TYPE: DNA
<213> ORGANISM: Homo Sapiens

<400> SEQUENCE: 25

```
atggtgaagg taccctggtt cccaagaaaa gtgtcagagc tggacaagtg tcatcacctg      60
gtcaccaagt tcgaccccga cctggacttg gaccaccccg gcttctcgga ccaggtgtac     120
cgccagcgca ggaagctgat cgctgagatc gccttccagt acaggcacgg cgacccgatc     180
ccccgtgtgg agtacaccgc cgaggagatc gccacctgga aggaggtcta caccaccctg     240
aagggcctct acgccaccca cgcctgcggg gagcacctgg aggcctttgc tttgctggag     300
cgcttcagcg gctaccggga agacaacatc ccccagctgg aggacgtctc ccgcttcctg     360
aaggagcgca caggcttcca gctgcggccc gtggccggcc tgctgtccgc ccgggacttc     420
ctggccagcc tggccttccg cgtgttccag tgcacccagt atatccgcca cgcgtcctcg     480
cccatgcact cccctgagcc ggactgctgc acgagctgc tggggcacgt gcccatgctg     540
gccgaccgca ccttcgcgca gttcagccag gacatcggcc tggcgtccct ggggccagc      600
gatgaggaaa tcgagaagct gtccactctg tcatggttca cggtggagtt cgggctgtgt     660
aagcagaacg gggaggtgaa ggcctatggt gccgggctgc tgtcctccta cggggagctc     720
ctgcactgcc tgtctgagga gcctgagatc cgggccttcg accctgaggc tgcggccgtg     780
cagccctacc aagaccagac gtaccagtca gtctacttcg tgtctgagag cttcagcgac     840
gccaaggaca agctcaggag ctatgccagc cgcatccagc gccccttctc cgtgaagttc     900
gacccgtaca ccctggccat cgacgtgctg acagccccc aggccgtgcg cgctccctg      960
gagggtgtcc aggatgagct ggacacccttt gcccatgcgc tgagcgccat cggctga    1017
```

<210> SEQ ID NO 26
<211> LENGTH: 338
<212> TYPE: PRT
<213> ORGANISM: Homo Sapiens

<400> SEQUENCE: 26

```
Met Val Lys Val Pro Trp Phe Pro Arg Lys Val Ser Glu Leu Asp Lys
  1               5                  10                  15

Cys His His Leu Val Thr Lys Phe Asp Pro Asp Leu Asp Leu Asp His
             20                  25                  30

Pro Gly Phe Ser Asp Gln Val Tyr Arg Gln Arg Lys Leu Ile Ala
         35                  40                  45

Glu Ile Ala Phe Gln Tyr Arg His Gly Asp Pro Ile Pro Arg Val Glu
 50                  55                  60

Tyr Thr Ala Glu Glu Ile Ala Thr Trp Lys Glu Val Tyr Thr Thr Leu
 65                  70                  75                  80

Lys Gly Leu Tyr Ala Thr His Ala Cys Gly Glu His Leu Glu Ala Phe
                 85                  90                  95

Ala Leu Leu Glu Arg Phe Ser Gly Tyr Arg Glu Asp Asn Ile Pro Gln
            100                 105                 110

Leu Glu Asp Val Ser Arg Phe Leu Lys Glu Arg Thr Gly Phe Gln Leu
        115                 120                 125

Arg Pro Val Ala Gly Leu Leu Ser Ala Arg Asp Phe Leu Ala Ser Leu
130                 135                 140

Ala Phe Arg Val Phe Gln Cys Thr Gln Tyr Ile Arg His Ala Ser Ser
145                 150                 155                 160

Pro Met His Ser Pro Glu Pro Asp Cys Cys His Glu Leu Leu Gly His
                165                 170                 175

Val Pro Met Leu Ala Asp Arg Thr Phe Ala Gln Phe Ser Gln Asp Ile
            180                 185                 190
```

```
Gly Leu Ala Ser Leu Gly Ala Ser Asp Glu Glu Ile Glu Lys Leu Ser
            195                 200                 205

Thr Leu Tyr Trp Phe Thr Val Glu Phe Gly Leu Cys Lys Gln Asn Gly
        210                 215                 220

Glu Val Lys Ala Tyr Gly Ala Gly Leu Leu Ser Ser Tyr Gly Glu Leu
225                 230                 235                 240

Leu His Cys Leu Ser Glu Glu Pro Glu Ile Arg Ala Phe Asp Pro Glu
                245                 250                 255

Ala Ala Ala Val Gln Pro Tyr Gln Asp Gln Thr Tyr Gln Ser Val Tyr
            260                 265                 270

Phe Val Ser Glu Ser Phe Ser Asp Ala Lys Asp Lys Leu Arg Ser Tyr
        275                 280                 285

Ala Ser Arg Ile Gln Arg Pro Phe Ser Val Lys Phe Asp Pro Tyr Thr
290                 295                 300

Leu Ala Ile Asp Val Leu Asp Ser Pro Gln Ala Val Arg Arg Ser Leu
305                 310                 315                 320

Glu Gly Val Gln Asp Glu Leu Asp Thr Leu Ala His Ala Leu Ser Ala
            325                 330                 335

Ile Gly

<210> SEQ ID NO 27
<211> LENGTH: 1017
<212> TYPE: DNA
<213> ORGANISM: Homo Sapiens

<400> SEQUENCE: 27
atggtgaagg taccctggtt cccaagaaaa gtgtcagagc tggacaagtg tcatcacctg      60
gtcaccaagt tcgaccctga cctggacttg gaccaccgg gcttctcgga ccaggtgtac     120
cgccagcgca ggaagctgat tgctgagatc gccttccagt acaggcacgg cgacccgatt     180
ccccgtgtgg agtacaccgc cgaggagatt gccacctgga aggaggtcta caccacgctg     240
aagggcctct acgccacgca cgcctgcggg gagcacctgg aggcctttgc tttgctggag     300
cgcttcagcg gctaccggga agacaatatc ccccagctgg aggacgtctc ccgcttcctg     360
aaggagcgca cgggcttcca gctgcggcct gtggccggcc tgctgtccgc ccgggacttc     420
ctggccagcc tggccttccg cgtgttccag tgcacccagt atatccgcca cgcgtcctcg     480
cccatgcact cccctgagcc ggactgctgc acgagctgc tggggcacgt gccatgctg     540 gccgaccgca ccttcgcgca gttctcgcag gacattggcc tggcgtccct ggggcctcg     600 gatgaggaaa ttgagaagct gtccacgctg tactggttca cggtggagtt cgggctgtgt     660
aagcagaacg gggaggtgaa ggcctatggt gccgggctgc tgtcctccta cggggagctc     720
ctgcactgcc tgtctgagga gcctgagatt cgggccttcg accctgaggc tgcggccgtg     780
cagccctacc aagaccagac gtaccagtca gtctacttcg tgtctgagag cttcagtgac     840
gccaaggaca agctcaggag ctatgcctca cgcatccagc gccccttctc cgtgaagttc     900
gacccgtaca cgctggccat cgacgtgctg gacagccccc aggccgtgcg cgcgtccctg     960
gagggtgtcc aggatgagct ggacacccctt gcccatgcgc tgagtgccat tggctag    1017

<210> SEQ ID NO 28
<211> LENGTH: 501
<212> TYPE: PRT
<213> ORGANISM: Homo Sapiens

<400> SEQUENCE: 28
```

```
Met Pro Thr Pro Asp Ala Thr Thr Pro Gln Ala Lys Gly Phe Arg Arg
1               5                   10                  15

Ala Val Ser Glu Leu Asp Ala Lys Gln Ala Glu Ala Ile Met Val Arg
            20                  25                  30

Gly Gln Ser Pro Arg Phe Ile Gly Arg Arg Gln Ser Leu Ile Glu Asp
        35                  40                  45

Ala Arg Lys Glu Arg Glu Ala Val Ala Ala Ala Ala Ala Ala Ala Val
    50                  55                  60

Pro Ser Glu Pro Gly Asp Pro Leu Glu Ala Val Ala Phe Glu Lys
65                  70                  75                  80

Glu Gly Lys Ala Val Leu Asn Leu Leu Phe Ser Pro Arg Ala Thr Lys
                85                  90                  95

Pro Ser Ala Leu Ser Arg Ala Val Lys Val Phe Glu Thr Phe Glu Ala
                100                 105                 110

Lys Ile His His Leu Glu Thr Arg Pro Ala Gln Arg Pro Arg Ala Gly
            115                 120                 125

Gly Pro His Leu Glu Tyr Phe Val Arg Leu Glu Val Arg Arg Gly Asp
        130                 135                 140

Leu Ala Ala Leu Leu Ser Gly Val Arg Gln Val Ser Glu Asp Val Arg
145                 150                 155                 160

Ser Pro Ala Gly Pro Lys Val Pro Trp Phe Pro Arg Lys Val Ser Glu
                165                 170                 175

Leu Asp Lys Cys His His Leu Val Thr Lys Phe Asp Pro Asp Leu Asp
            180                 185                 190

Leu Asp His Pro Gly Phe Ser Asp Gln Val Tyr Arg Gln Arg Arg Lys
        195                 200                 205

Leu Ile Ala Glu Ile Ala Phe Gln Tyr Arg His Gly Asp Pro Ile Pro
    210                 215                 220

Arg Val Glu Tyr Thr Ala Glu Ile Ala Thr Trp Lys Glu Val Tyr
225                 230                 235                 240

Thr Thr Leu Lys Gly Leu Tyr Ala Thr His Ala Cys Gly Glu His Leu
                245                 250                 255

Glu Ala Phe Ala Leu Leu Glu Arg Phe Ser Gly Tyr Arg Glu Asp Asn
            260                 265                 270

Ile Pro Gln Leu Glu Asp Val Ser Arg Phe Leu Lys Glu Arg Thr Gly
        275                 280                 285

Phe Gln Leu Arg Pro Val Ala Gly Leu Leu Ser Ala Arg Asp Phe Leu
    290                 295                 300

Ala Ser Leu Ala Phe Arg Val Phe Gln Cys Thr Gln Tyr Ile Arg His
305                 310                 315                 320

Ala Ser Ser Pro Met His Ser Pro Glu Pro Asp Cys Cys His Glu Leu
                325                 330                 335

Leu Gly His Val Pro Met Leu Ala Asp Arg Thr Phe Ala Gln Phe Ser
            340                 345                 350

Gln Asp Ile Gly Leu Ala Ser Leu Gly Ala Ser Asp Glu Glu Ile Glu
        355                 360                 365

Lys Leu Ser Thr Leu Tyr Trp Phe Thr Val Glu Phe Gly Leu Cys Lys
    370                 375                 380

Gln Asn Gly Glu Val Lys Ala Tyr Gly Ala Gly Leu Leu Ser Ser Tyr
385                 390                 395                 400

Gly Glu Leu Leu His Cys Leu Ser Glu Glu Pro Glu Ile Arg Ala Phe
                405                 410                 415
```

```
Asp Pro Glu Ala Ala Val Gln Pro Tyr Gln Asp Gln Thr Tyr Gln
            420                 425                 430

Ser Val Tyr Phe Val Ser Glu Ser Phe Ser Asp Ala Lys Asp Lys Leu
            435                 440                 445

Arg Ser Tyr Ala Ser Arg Ile Gln Arg Pro Phe Ser Val Lys Phe Asp
        450                 455                 460

Pro Tyr Thr Leu Ala Ile Asp Val Leu Asp Ser Pro Gln Ala Val Arg
465                 470                 475                 480

Arg Ser Leu Glu Gly Val Gln Asp Glu Leu Asp Thr Leu Ala His Ala
                485                 490                 495

Leu Ser Ala Ile Gly
            500

<210> SEQ ID NO 29
<211> LENGTH: 1506
<212> TYPE: DNA
<213> ORGANISM: Homo Sapiens

<400> SEQUENCE: 29
atgcccaccc ccgacgccac cacgccacag gccaagggct tccgcagggc cgtgtctgag      60
ctggacgcca agcaggcaga ggccatcatg gtaagagggc agtccccgcg gttcattggg     120
cgcaggcaga gcctcatcga ggacgcccgc aaggagcggg aggcggcggt ggcagcagcg     180
gccgctgcag tccccctcgga gcccggggac ccctggagg ctgtggcctt tgaggagaag     240 gagggggaagg ccgtgctaaa cctgctcttc tccccgaggg ccaccaagcc ctcggcgctg     300
tcccgagctg tgaaggtgtt tgagacgttt gaagccaaaa tccaccatct agagacccgg     360
cccgcccaga ggccgcgagc tgggggcccc cacctggagt acttcgtgcg cctcgaggtg     420
cgccgagggg acctggccgc cctgctcagt ggtgtgcgcc aggtgtcaga ggacgtgcgc     480
agccccgcgg ggcccaaggt ccctggttc caagaaaag tgtcagagct ggacaagtgt     540
catcacctgg tcaccaagtt cgaccctgac ctggacttgg accaccgggg cttctcggac     600
caggtgtacc gccagcgcag gaagctgatt gctgagatcg ccttccagta caggcacggc     660
gacccgattc ccgtgtgga gtacaccgcc gaggagattg ccacctggaa ggaggtctac     720
accacgctga agggcctcta cgccacgcac gcctgcgggg agcacctgga ggcctttgct     780
ttgctggagc gcttcagcgg ctaccgggaa gacaatatcc cccagctgga ggacgtctcc     840
cgcttcctga aggagcgcac gggcttccag ctgcggcctg tggccggcct gctgtccgcc     900
cgggacttcc tggccagcct ggccttccgc gtgttccagt gcacccagta tatccgccac     960
gcgtcctcgc ccatgcactc ccctgagccg gactgctgcc acgagctgct ggggcacgtg    1020
cccatgctgg ccgaccgcac cttcgcgcag ttctcgcagg acattggcct ggcgtccctg    1080
ggggcctcgg atgaggaaat tgagaagctg tccacgctgt actggttcac ggtggagttc    1140
gggctgtgta gcagaacgg ggaggtgaag gcctatggtg ccgggctgct gtcctcctac    1200
ggggagctcc tgcactgcct gtctgaggag cctgagattc gggccttcga ccctgaggct    1260
gcggccgtgc agccctacca agaccagacg taccagtcag tctacttcgt gtctgagagc    1320
ttcagtgacg ccaaggacaa gctcaggagc tatgcctcac gcatccagcg ccccttctcc    1380
gtgaagttcg acccgtacac gctggccatc gacgtgctgg acagccccca ggccgtgcgg    1440
cgctccctgg agggtgtcca ggatgagctg gacacccttg cccatgcgct gagtgccatt    1500
ggctag                                                                1506
```

```
<210> SEQ ID NO 30
<211> LENGTH: 480
<212> TYPE: PRT
<213> ORGANISM: Homo Sapiens

<400> SEQUENCE: 30

Met Asp Ala Ser Glu Phe Arg Arg Gly Lys Glu Met Val Asp Tyr
1               5                   10                  15

Val Ala Asn Tyr Met Glu Gly Ile Glu Gly Arg Gln Val Tyr Pro Asp
                20                  25                  30

Val Glu Pro Gly Tyr Leu Arg Pro Leu Ile Pro Ala Ala Ala Pro Gln
                35                  40                  45

Glu Pro Asp Thr Phe Glu Asp Ile Ile Asn Asp Val Glu Lys Ile Ile
            50                  55                  60

Met Pro Gly Val Thr His Trp His Ser Pro Tyr Phe Phe Ala Tyr Phe
65                  70                  75                  80

Pro Thr Ala Ser Ser Tyr Pro Ala Met Leu Ala Asp Met Leu Cys Gly
                85                  90                  95

Ala Ile Gly Cys Ile Gly Phe Ser Trp Ala Ala Ser Pro Ala Cys Thr
                100                 105                 110

Glu Leu Glu Thr Val Met Met Asp Trp Leu Gly Lys Met Leu Glu Leu
            115                 120                 125

Pro Lys Ala Phe Leu Asn Glu Lys Ala Gly Glu Gly Gly Val Ile
130                 135                 140

Gln Gly Ser Ala Ser Glu Ala Thr Leu Val Ala Leu Leu Ala Ala Arg
145                 150                 155                 160

Thr Lys Val Ile His Arg Leu Gln Ala Ala Ser Pro Glu Leu Thr Gln
                165                 170                 175

Ala Ala Ile Met Glu Lys Leu Val Ala Tyr Ser Ser Asp Gln Ala His
                180                 185                 190

Ser Ser Val Glu Arg Ala Gly Leu Ile Gly Gly Val Lys Leu Lys Ala
                195                 200                 205

Ile Pro Ser Asp Gly Asn Phe Ala Met Arg Ala Ser Ala Leu Gln Glu
210                 215                 220

Ala Leu Glu Arg Asp Lys Ala Ala Gly Leu Ile Pro Phe Phe Met Val
225                 230                 235                 240

Ala Thr Leu Gly Thr Thr Thr Cys Cys Ser Phe Asp Asn Leu Leu Glu
                245                 250                 255

Val Gly Pro Ile Cys Asn Lys Glu Asp Ile Trp Leu His Val Asp Ala
                260                 265                 270

Ala Tyr Ala Gly Ser Ala Phe Ile Cys Pro Glu Phe Arg His Leu Leu
                275                 280                 285

Asn Gly Val Glu Phe Ala Asp Ser Phe Asn Phe Asn Pro His Lys Trp
            290                 295                 300

Leu Leu Val Asn Phe Asp Cys Ser Ala Met Trp Val Lys Lys Arg Thr
305                 310                 315                 320

Asp Leu Thr Gly Ala Phe Arg Leu Asp Pro Thr Tyr Leu Lys His Ser
                325                 330                 335

His Gln Asp Ser Gly Leu Ile Thr Asp Tyr Arg His Trp Gln Ile Pro
                340                 345                 350

Leu Gly Arg Arg Phe Arg Ser Leu Lys Met Trp Phe Val Phe Arg Met
                355                 360                 365

Tyr Gly Val Lys Gly Leu Gln Ala Tyr Ile Arg Lys His Val Gln Leu
370                 375                 380
```

-continued

```
Ser His Glu Phe Glu Ser Leu Val Arg Gln Asp Pro Arg Phe Glu Ile
385                 390                 395                 400

Cys Val Glu Val Ile Leu Gly Leu Val Cys Phe Arg Leu Lys Gly Ser
            405                 410                 415

Asn Lys Val Asn Glu Ala Leu Leu Gln Arg Ile Asn Ser Ala Lys Lys
        420                 425                 430

Ile His Leu Val Pro Cys His Leu Arg Asp Lys Phe Val Leu Arg Phe
    435                 440                 445

Ala Ile Cys Ser Arg Thr Val Glu Ser Ala His Val Gln Arg Ala Trp
450                 455                 460

Glu His Ile Lys Glu Leu Ala Ala Asp Val Leu Arg Ala Glu Arg Glu
465                 470                 475                 480
```

<210> SEQ ID NO 31
<211> LENGTH: 1443
<212> TYPE: DNA
<213> ORGANISM: Homo Sapiens

<400> SEQUENCE: 31

```
atggacgcca gtgagttccg aaggcgcggc aaggagatgg tggactacgt ggccaactac      60
atggaaggca tcgagggccg ccaagtctac cccgacgtgg agcccggcta cctgcgcccg     120
ctgatccccg ccgctgcccc tcaggagccc gacaccttcg aggacatcat caacgacgtg     180
gagaagatca tcatgcctgg cgtgacgcac tggcacagcc cctacttctt cgcctacttc     240
cccaccgcca gctcgtaccc ggccatgctg gcggacatgc tgtgcggggc cattggctgc     300
atcggcttct cctgggcggc gagcccagcg tgcaccgagc tggagaccgt gatgatggac     360
tggctcggga gatgctggag gctcccaaag gcgttcttga acgagaaggc tggcgagggg     420
ggcggcgtga tccagggcag cgccagcgag gccaccctgg tggccctgct ggccgctcgg     480
accaaagtga tccaccggct gcaggcagcg tccccagagc tcacccaggc cgctatcatg     540
gagaagctgg tggcttactc ctccgatcag gcacactcct ccgtggaacg cgctgggctc     600
attggtggag tgaagctcaa ggccatcccc agcgatggca acttcgccat gcgtgcgagc     660
gccctgcagg aagccctgga gagagacaag gcggctggcc tgattccttt cttcatggtg     720
gccaccctgg ggaccacaac atgctgctcc ttcgacaacc tcctcgaagt cggtcctatc     780
tgcaacaagg aagacatctg gctgcacgtt gatgcagcct acgcaggcag cgcattcatc     840
tgccctgagt tccggcacct tctgaacgga gtggagttcg cagatagctt caacttcaat     900
ccccacaagt ggctattggt gaatttcgac tgcagcgcca tgtgggtgaa gagcgcacc     960
gacctcacgg gagccttccg cctggacccc acttacctga agcacagcca ccaggattca    1020
gggcttatca ctgactaccg gcactggcag atcccactgg ccgcagatt ccgcagcttg    1080
aagatgtggt tcgtattcag gatgtatgga gtcaagggac tgcaggctta tatccgcaag    1140
catgtccagc tgtcccatga gtttgagtca ctggtgcgcc aggatccccg ctttgaaatc    1200
tgtgtggaag tcattctggg gcttgtctgc tttcggctaa agggttccaa caaagtgaat    1260
gaagctcttc tgcaaaggat caacagtgcc aaaaaaatcc acttggttcc atgtcacctc    1320
agggacaagt ttgtcctgcg ctttgccatc tgttctcgca ccgtggaatc tgcccatgtg    1380
cagcgggcct ggaacacat caaagagctg gcggccgacg tgctgcgagc agagagggag    1440
tag                                                                 1443
```

<210> SEQ ID NO 32
<211> LENGTH: 480

```
<212> TYPE: PRT
<213> ORGANISM: Homo Sapiens

<400> SEQUENCE: 32

Met Asn Ala Ser Glu Phe Arg Arg Gly Lys Glu Met Val Asp Tyr
1               5                   10                  15

Val Ala Asn Tyr Met Glu Gly Ile Glu Gly Arg Gln Val Tyr Pro Asp
            20                  25                  30

Val Glu Pro Gly Tyr Leu Arg Pro Leu Ile Pro Ala Ala Pro Gln
        35                  40                  45

Glu Pro Asp Thr Phe Glu Asp Ile Ile Asn Asp Val Glu Lys Ile Ile
    50                  55                  60

Met Pro Gly Val Thr His Trp His Ser Pro Tyr Phe Ala Tyr Phe
65              70                  75                  80

Pro Thr Ala Ser Ser Tyr Pro Ala Met Leu Ala Asp Met Leu Cys Gly
            85                  90                  95

Ala Ile Gly Cys Ile Gly Phe Ser Trp Ala Ala Ser Pro Ala Cys Thr
            100                 105                 110

Glu Leu Glu Thr Val Met Met Asp Trp Leu Gly Lys Met Leu Glu Leu
        115                 120                 125

Pro Lys Ala Phe Leu Asn Glu Lys Ala Gly Glu Gly Gly Val Ile
130                 135                 140

Gln Gly Ser Ala Ser Glu Ala Thr Leu Val Ala Leu Leu Ala Ala Arg
145                 150                 155                 160

Thr Lys Val Ile His Arg Leu Gln Ala Ala Ser Pro Glu Leu Thr Gln
                165                 170                 175

Ala Ala Ile Met Glu Lys Leu Val Ala Tyr Ser Ser Asp Gln Ala His
            180                 185                 190

Ser Ser Val Glu Arg Ala Gly Leu Ile Gly Val Lys Leu Lys Ala
        195                 200                 205

Ile Pro Ser Asp Gly Asn Phe Ala Met Arg Ala Ser Ala Leu Gln Glu
    210                 215                 220

Ala Leu Glu Arg Asp Lys Ala Ala Gly Leu Ile Pro Phe Phe Met Val
225                 230                 235                 240

Ala Thr Leu Gly Thr Thr Thr Cys Cys Ser Phe Asp Asn Leu Leu Glu
                245                 250                 255

Val Gly Pro Ile Cys Asn Lys Glu Asp Ile Trp Leu His Val Asp Ala
            260                 265                 270

Ala Tyr Ala Gly Ser Ala Phe Ile Cys Pro Glu Phe Arg His Leu Leu
        275                 280                 285

Asn Gly Val Glu Phe Ala Asp Ser Phe Asn Phe Asn Pro His Lys Trp
    290                 295                 300

Leu Leu Val Asn Phe Asp Cys Ser Ala Met Trp Val Lys Lys Arg Thr
305                 310                 315                 320

Asp Leu Thr Gly Ala Phe Arg Leu Asp Pro Thr Tyr Leu Lys His Ser
                325                 330                 335

His Gln Asp Ser Gly Leu Ile Thr Asp Tyr Arg His Trp Gln Ile Pro
            340                 345                 350

Leu Gly Arg Arg Phe Arg Ser Leu Lys Met Trp Phe Val Phe Arg Met
        355                 360                 365

Tyr Gly Val Lys Gly Leu Gln Ala Tyr Ile Arg Lys His Val Gln Leu
    370                 375                 380

Ser His Glu Phe Glu Ser Leu Val Arg Gln Asp Pro Arg Phe Glu Ile
385                 390                 395                 400
```

```
Cys Val Glu Val Ile Leu Gly Leu Val Cys Phe Arg Leu Lys Gly Ser
                405                 410                 415

Asn Lys Val Asn Glu Ala Leu Leu Gln Arg Ile Asn Ser Ala Lys Lys
            420                 425                 430

Ile His Leu Val Pro Cys His Leu Arg Asp Lys Phe Val Leu Arg Phe
        435                 440                 445

Ala Ile Cys Ser Arg Thr Val Glu Ser Ala His Val Gln Arg Ala Trp
    450                 455                 460

Glu His Ile Lys Glu Leu Ala Ala Asp Val Leu Arg Ala Glu Arg Glu
465                 470                 475                 480

<210> SEQ ID NO 33
<211> LENGTH: 1443
<212> TYPE: DNA
<213> ORGANISM: Homo Sapiens

<400> SEQUENCE: 33
atgaacgcaa gtgaattccg aaggagaggg aaggagatgg tggattacgt ggccaactac      60
atggaaggca ttgagggacg ccaggtctac cctgacgtgg agcccgggta cctgcggccg     120
ctgatccctg ccgctgcccc tcaggagcca gacacgtttg aggacatcat caacgacgtt     180
gagaagataa tcatgcctgg ggtgacgcac tggcacagcc cctacttctt cgcctacttc     240
cccactgcca gctcgtaccc ggccatgctt gcggacatgc tgtgcggggc cattggctgc     300
atcggcttct cctgggcggc aagcccagca tgcacagagc tggagactgt gatgatggac     360
tggctcggga agatgctgga actaccaaag gcattttga atgagaaagc tggagaaggg     420
ggaggagtga tccagggaag tgccagtgaa gccaccctgg tggccctgct ggccgctcgg     480
accaaagtga tccatcggct gcaggcagcg tccccagagc tcacacaggc cgctatcatg     540
gagaagctgg tggcttactc atccgatcag gcacactcct cagtgaaaag gctgggtta      600 attggtggag tgaaattaaa agccatcccc tcagatggca acttcgccat gcgtgcgtct     660
gccctgcagg aagccctgga gagagacaaa gcggctggcc tgattccttt ctttatggtt     720 gccacctgg ggaccacaac atgctgctcc tttgacaatc tcttagaagt cggtcctatc      780
tgcaacaagg aagacatatg gctgcacgtt gatgcagcct acgcaggcag tgcattcatc     840
tgccctgagt ccggcaccct tctgaatgga gtggagtttg cagattcatt caactttaat     900
ccccacaaat ggctattggt gaattttgac tgttctgcca tgtgggtgaa aaagagaaca     960
gacttaacgg gagcctttag actggacccc acttacctga agcacagcca tcaggattca    1020
gggcttatca ctgactaccg gcattggcag ataccactgg gcagaagatt tcgctctttg    1080
aaaatgtggt ttgtatttag gatgtatgga gtcaaaggac tgcaggctta tatccgcaag    1140
catgtccagc tgtcccatga gtttgagtca ctggtgcgcc aggatccccg ctttgaaatc    1200
tgtgtggaag tcattctggg gcttgtctgc tttcggctaa agggttccaa caaagtgaat    1260
gaagctcttc tgcaaagaat aaacagtgcc aaaaaaatcc acttggttcc atgtcacctc    1320
agggacaagt ttgtcctgcg ctttgccatc tgttctcgca cggtggaatc tgcccatgtg    1380
cagcgggcct gggaacacat caaagagctg gcggccgacg tgctgcgagc agagagggag    1440
tag                                                                  1443

<210> SEQ ID NO 34
<211> LENGTH: 11622
<212> TYPE: DNA
<213> ORGANISM: Equine Infectious Anemia Virus
```

```
<400> SEQUENCE: 34
tttgagattt ctgtcgccga ctaaattcat gtcgcgcgat agtggtgttt atcgccgata        60
gagatggcga tattggaaaa attgatattt gaaaatatgg catattgaaa atgtcgccga       120
tgtgagtttc tgtgtaactg atatcgccat ttttccaaaa gtgattttg  ggcatacgcg       180 atatctggcg atagcgctta tatcgtttac ggggatggc  gatagacgac tttggtgact       240
tgggcgattc tgtgtgtcgc aaatatcgca gtttcgatat aggtgacaga cgatatgagg       300
ctatatcgcc gatagaggcg acatcaagct ggcacatggc caatgcatat cgatctatac       360
attgaatcaa tattggccat tagccatatt attcattggt tatatagcat aaatcaatat       420
tggctattgg ccattgcata cgttgtatcc atatcgtaat atgtacattt atattggctc       480
atgtccaaca ttaccgccat gttgacattg attattgact agttattaat agtaatcaat       540 tacgggtca  ttagttcata gcccatatat ggagttccgc gttacataac ttacggtaaa       600
tggcccgcct ggctgaccgc ccaacgaccc ccgcccattg acgtcaataa tgacgtatgt       660
tcccatagta acgccaatag ggactttcca ttgacgtcaa tgggtggagt atttacggta       720
aactgcccac ttggcagtac atcaagtgta tcatatgcca gtccgcccc  ctattgacgt       780 caatgacggt aaatggcccg cctggcatta tgcccagtac atgaccttac ggactttcc       840 tacttggcag tacatctacg tattagtcat cgctattacc atggtgatgc ggttttggca       900
gtacaccaat gggcgtggat agcggtttga ctcacgggga tttccaagtc tccaccccat       960
tgacgtcaat gggagtttgt tttggcacca aaatcaacgg gactttccaa aatgtcgtaa      1020
caactgcgat cgcccgcccc gttgacgcaa atgggcggta ggcgtgtacg gtgggaggtc      1080
tatataagca gagctcgttt agtgaaccgg gcactcagat tctgcggtct gagtcccttc      1140
tctgctgggc tgaaaaggcc tttgtaataa atataattct ctactcagtc cctgtctcta      1200
gtttgtctgt tcgagatcct acagttggcg cccgaacagg gacctgagag gggcgcagac      1260
cctacctgtt gaacctggct gatcgtagga tccccgggac agcagaggag aacttacaga      1320
agtcttctgg aggtgttcct ggccagaaca caggaggaca ggtaagattg ggagacccctt     1380 tgacattgga gcaaggcgct caagaagtta gagaaggtga cggtacaagg gtctcagaaa      1440
ttaactactg gtaactgtaa ttgggcgcta agtctagtag acttatttca ttgataccaa      1500
ctttgtaaaa gaaaaggact ggcagctgag ggattgtcat tccattgctg gaagattgta      1560
actcagacgc tgtcaggaca agaaagagag gcctttgaaa gaacattggt gggcaatttc      1620
tgctgtaaag attgggcctc cagattaata attgtagtag attggaaagg catcattcca      1680
gctcctaaga gcgaaatatt gaaaagaaga ctgctaataa aaagcagtct gagccctctg      1740
aagaatatct ctagaactag tggatccccc gggccaaaac ctagcgccac catgattgaa      1800
caagatggat tgcacgcagg ttctccggcc gcttgggtgg agaggctatt cggctatgac      1860
tgggcacaac agacaatcgg ctgctctgat gccgccgtgt tccggctgtc agcgcagggg      1920
cgcccggttc tttttgtcaa gaccgacctg tccggtgccc tgaatgaact gcaggacgag      1980
gcagcgcggc tatcgtggct ggccacgacg ggcgttcctt gcgcagctgt gctcgacgtt      2040
gtcactgaag cgggaaggga ctggctgcta ttgggcgaag tgccggggca ggatctcctg      2100
tcatctcacc ttgctcctgc cgagaaagta tccatcatgg ctgatgcaat gcggcggctg      2160
catacgcttg atccggctac ctgcccattc gaccaccaag cgaaacatcg catcgagcga      2220
gcacgtactc ggatggaagc cggtcttgtc gatcaggatg atctggacga agagcatcag      2280
```

```
gggctcgcgc cagccgaact gttcgccagg ctcaaggcgc gcatgcccga cggcgaggat    2340
ctcgtcgtga cccatggcga tgcctgcttg ccgaatatca tggtggaaaa tggccgcttt    2400
tctggattca tcgactgtgg ccggctgggt gtggcggacc gctatcagga catagcgttg    2460
gctacccgtg atattgctga agagcttggc ggcgaatggg ctgaccgctt cctcgtgctt    2520
tacggtatcg ccgctcccga ttcgcagcgc atcgccttct atcgccttct tgacgagttc    2580
ttctgagcgg ccgcgaattc aaaagctaga gtcgactcta gggagtgggg aggcacgatg    2640
gccgctttgg tcgaggcgga tccggccatt agccatatta ttcattggtt atatagcata    2700
aatcaatatt ggctattggc cattgcatac gttgtatcca tatcataata tgtacattta    2760
tattggctca tgtccaacat taccgccatg ttgacattga ttattgacta gttattaata    2820
gtaatcaatt acgggtcat tagttcatag cccatatatg gagttccgcg ttacataact    2880
tacggtaaat ggcccgcctg gctgaccgcc caacgacccc cgcccattga cgtcaataat    2940
gacgtatgtt cccatagtaa cgccaatagg gactttccat tgacgtcaat gggtggagta    3000
tttacggtaa actgcccact tggcagtaca tcaagtgtat catatgccaa gtacgccccc    3060
tattgacgtc aatgacggta aatggcccgc ctggcattat gcccagtaca tgaccttatg    3120
ggactttcct acttggcagt acatctacgt attagtcatc gctattacca tggtgatgcg    3180 gttttgcag tacatcaatg gcgtggata gcggtttgac tcacgggat ttccaagtct    3240 ccacccatt gacgtcaatg ggagtttgtt ttggcaccaa aatcaacggg actttccaaa    3300
atgtcgtaac aactccgccc cattgacgca aatgggcggt aggcatgtac ggtgggaggt    3360
ctatataagc agagctcgtt tagtgaaccg tcagatcgcc tggagacgcc atccacgctg    3420
ttttgacctc catagaagac accgggaccg atccagcctc cgcggcccca agctagtcga    3480
ctttaagctt ctcgagaatt cgtgcaccat ggtgaaggta ccctggttcc caagaaaagt    3540
gtcagagctg gacaagtgtc atcacctggt caccaagttc gaccccgacc tggacttgga    3600 ccacccggc ttctcggacc aggtgtaccg ccagcgcagg aagctgatcg ctgagatcgc    3660
cttccagtac aggcacggcg acccgatccc ccgtgtggag tacaccgccg aggagatcgc    3720
cacctggaag gaggtctaca ccaccctgaa gggcctctac gccacccacg cctgcgggga    3780
gcacctggag gcctttgctt tgctggagcg cttcagcggc taccgggaag acaacatccc    3840
ccagctggag gacgtctccc gcttcctgaa ggagcgcaca ggcttccagc tgcggcccgt    3900
ggccggcctg ctgtccgccc gggacttcct ggccagcctg gccttccgcg tgttccagtg    3960
cacccagtat atccgccacg cgtcctcgcc catgcactcc cctgagccgg actgctgcca    4020
cgagctgctg gggcacgtgc ccatgctggc cgaccgcacc ttcgcgcagt tcagccagga    4080
catcggcctg gcgtccctgg gggccagcga tgaggaaatc gagaagctgt ccactctgta    4140
ctggttcacg gtggagttcg ggctgtgtaa gcagaacggg gaggtgaagg cctatggtgc    4200
cgggctgctg tcctcctacg gggagctcct gcactgcctg tctgaggagc ctgagatccg    4260
ggccttcgac cctgaggctg cggccgtgca gccctaccaa gaccagacgt accagtcagt    4320
ctacttcgtg tctgagagct tcagcgacgc caaggacaag ctcaggagct atgccagccg    4380
catccagcgc ccttctccg tgaagttcga cccgtacacc ctggccatcg acgtgctgga    4440 cagccccag gccgtgcggc gctccctgga gggtgtccag gatgagctgg acacccttgc    4500
ccatgcgctg agcgccatcg gctgagcagt ggcggccgca ctagaggaat tcgcccctct    4560
ccctcccccc ccctaacgt tactggccga agccgcttgg aataaggccg gtgtgtgttt    4620
gtctatatgt gattttccac catattgccg tcttttggca atgtgagggc ccggaaacct    4680
```

-continued

```
ggccctgtct tcttgacgag cattcctagg ggtctttccc ctctcgccaa aggaatgcaa    4740
ggtctgttga atgtcgtgaa ggaagcagtt cctctggaag cttcttgaag acaaacaacg    4800
tctgtagcga cccttttgcag gcagcggaac cccccacctg cgacaggtg cctctgcggc    4860 caaaagccac gtgtataaga tacacctgca aggcggcac aaccccagtg ccacgttgtg    4920
agttggatag ttgtggaaag agtcaaatgg ctctcctcaa cgtagtcaa caaggggctg    4980 aaggatgccc agaaggtacc ccattgtatg ggaatctgat ctggggcctc ggtgcacatg    5040
ctttacatgt gtttagtcga ggttaaaaaa gctctaggcc ccccgaacca cggggacgtg    5100
gttttccttt gaaaaacacg atgataccat ggacgccagt gagttccgaa ggcgcggcaa    5160
ggagatggtg gactacgtgg ccaactacat ggaaggcatc gagggccgcc aagtctaccc    5220
cgacgtggag cccggctacc tgcgcccgct gatccccgcc gctgcccctc aggagcccga    5280
caccttcgag gacatcatca cgacgtgga aagatcatc atgcctggcg tgacgcactg    5340
gcacagcccc tacttcttcg cctacttccc caccgccagc tcgtacccgg ccatgctggc    5400
ggacatgctg tgcggggcca ttggctgcat cggcttctcc tgggcggcga gcccagcgtg    5460
caccgagctg gagaccgtga tgatggactg gctcgggaag atgctggagc tcccaaaggc    5520
gttcttgaac gagaaggctg gcgagggggg cggcgtgatc cagggcagcg ccagcgaggc    5580 cacccctggtg gccctgctgg ccgctcggac caaagtgatc caccggctgc aggcagcgtc    5640
cccagagctc acccaggccg ctatcatgga gaagctggtg gcttactcct ccgatcaggc    5700
acactcctcc gtgaacgcg ctgggctcat tggtggagtg aagctcaagg ccatccccag    5760
cgatggcaac ttcgccatgc gtgcgagcgc cctgcaggaa gccctggaga gagacaaggc    5820
ggctggcctg attcctttct tcatggtggc caccctgggg accacaacat gctgctcctt    5880
cgacaacctc ctcgaagtcg gtcctatctg caacaaggaa gacatctggc tgcacgttga    5940
tgcagcctac gcaggcagcg cattcatctg ccctgagttc cggcaccttc tgaacggagt    6000
ggagttcgca gatagcttca acttcaatcc cacaagtgg ctattggtga atttcgactg    6060
cagcgccatg tgggtgaaga gcgcaccga cctcacggga gccttccgcc tggaccccac    6120
ttacctgaag cacagccacc aggattcagg gcttatcact gactaccggc actggcagat    6180
cccactgggc cgcagattcc gcagcttgaa gatgtggttc gtattcagga tgtatggagt    6240
caagggactg caggcttata tccgcaagca tgtccagctg tcccatgagt ttgagtcact    6300
ggtgcgccag gatccccgct ttgaaatctg tgtggaagtc attctggggc ttgtctgctt    6360
tcggctaaag ggttccaaca aagtgaatga agctcttctg caaaggatca acagtgccaa    6420
aaaaatccac ttggttccat gtcacctcag ggacaagttt gtcctgcgct ttgccatctg    6480
ttctcgcacc gtggaatctg cccatgtgca gcgggcctgg aacacatca aagagctggc    6540 ggccgacgtg ctgcgagcag agagggagta gctcgaaaac ccgctgatca gcctcgactg    6600
tgccttctag ttgccagcca tctgttgttt gccccctccc cgtgccttcc ttgagaattc    6660
ctcgacgtag atatcttaaa acagctctgg ggttgtaccc accccagagg cccacgtggc    6720
ggctagtact ccggtattgc ggtacctttg tacgcctgtt ttatactccc ttcccccgta    6780
acttagaagc acaatgtcca agttcaatag gagggggtac aaaccagtac caccacgaac    6840
aagcacttct gttccccgg tgaggctgta taggctgttt ccacggctaa aagcggctga    6900
tccgttatcc gctcatgtac ttcgagaagc ctagtatcac cttggaatct tcgatgcgtt    6960
gcgctcaaca ctcaaccca gagtgtagct taggtcgatg agtctggacg ttcctcaccg    7020
```

-continued

```
gcgacggtgg tccaggctgc gttggcggcc tacctgtggc ccaaagccac aggacgctag    7080
ttgtgaacaa ggtgtgaaga gcctattgag ctacctgaga gtcctccggc ccctgaatgc    7140
ggctaatcct aaccacggag caggcagtgg caatccagcg accagcctgt cgtaacgcgc    7200
aagttcgtgg cggaaccgac tactttgggt gtccgtgttt cctttatttt ttacaatggc    7260
tgcttatggt gacaatcatt gattgttatc ataaagcaaa ttggattggc catccggtga    7320
gaatttgatt attaaattac tctcttgttg ggattgctcc tttgaaatct tgtgcactca    7380
cacctattgg aattacctca ttgttaaacg cgtctagcta gcgccaccat ggagaagggc    7440
cctgtgcgcg ccccggccga aagccgcgc ggcgcccgct gcagcaatgg gttccccgag    7500
cgcgacccgc cgcgccccgg gcccagcagg ccggccgaga agccccgcg ccccgaggcc    7560 aagagcgcg agcccgcgga cggctggaag gcgagcgcc cccgcagcga ggaggacaac    7620
gagctgaacc tccctaacct ggccgccgcc tactcctcca tcctgagctc gctgggcgag    7680 aaccccagc ggcaggggct gctcaagacc ccctggaggg cggcctcggc catgcagttc    7740
ttcaccaagg gctaccagga gaccatctca gacgtcctga cgacgctat cttcgacgaa    7800 gatcacgatg agatggtgat cgtgaaggac atagacatgt tctccatgtg cgagcaccac    7860
ctggtgccat tgtgggaaa ggtccatatc ggctacctgc taacaagca ggtcctgggc    7920 ctcagcaagc tggcgaggat tgtggaaatc tatagtagaa gactacaggt tcaggagcgc    7980
cttaccaaac aaattgctgt ggcaatcacg gaagccttgc ggcctgctgg agtcggggtc    8040
gtggtggaag caacacacat gtgtatggtg atgcgaggtg tacagaaaat gaacagcaaa    8100
accgtgacca gcacaatgct gggtgtgttc cgggaggatc caaagactcg ggaagagttc    8160
ctgactctca tcaggagctg aagaattcct cgacagctta tcgataatca acctctggat    8220
tacaaaattt gtgaaagatt gactggtatt cttaactatg ttgctccttt tacgctatgt    8280
ggatacgctg ctttaatgcc tttgtatcat gctattgctt cccgtatggc tttcattttc    8340
tcctccttgt ataaatcctg gttgctgtct ctttatgagg agttgtggcc cgttgtcagg    8400
caacgtggcg tggtgtgcac tgtgtttgct gacgcaaccc ccactggttg gggcattgcc    8460
accacctgtc agctcctttc cgggactttc gctttccccc tccctattgc cacggcggaa    8520
ctcatcgccg cctgccttgc ccgctgctgg acagggctc ggctgttggg cactgacaat    8580
tccgtggtgt tgtcggggaa atcatcgtcc tttccttggc tgctcgcctg tgttgccacc    8640
tggattctgc gcgggacgtc cttctgctac gtcccttcgg ccctcaatcc agcggacctt    8700
ccttcccgcg gcctgctgcc ggctctgcgg cctcttccgc gtcttcgcct tcgccctcag    8760
acgagtcgga tctcccttg ggccgcctcc ccgcatcgat accgtcgaat tggaagagct    8820
ttaaatcctg gcacatctca tgtatcaatg cctcagtatg tttagaaaaa caaggggga    8880 actgtggggt ttttatgagg ggttttatac aattgggcac tcagattctg cggtctgagt    8940
cccttctctg ctgggctgaa aaggcctttg taataaatat aattctctac tcagtccctg    9000
tctctagttt gtctgttcga gatcctacag agctcatgcc ttggcgtaat catggtcata    9060
gctgtttcct gtgtgaaatt gttatccgct cacaattcca cacaacatac gagccgggag    9120
cataaagtgt aaagcctggg gtgcctaatg agtgagctaa ctcacattaa ttgcgttgcg    9180
ctcactgccc gctttccagt cgggaaacct gtcgtgccag ctgcattaat gaatcggcca    9240
acgcgcgggg agaggcggtt tgcgtattgg gcgctcttcc gcttcctcgc tcactgactc    9300
gctgcgctcg tcgttcggc tgcggcgagc ggtatcagct cactcaaagg cggtaatacg    9360
gttatccaca gaatcagggg ataacgcagg aaagaacatg tgagcaaaag gccagcaaaa    9420
```

```
ggccaggaac cgtaaaaagg ccgcgttgct ggcgtttttc cataggctcc gccccctga    9480 cgagcatcac aaaaatcgac gctcaagtca gaggtggcga aacccgacag gactataaag   9540
ataccaggcg tttccccctg gaagctccct cgtgcgctct cctgttccga ccctgccgct   9600
taccggatac ctgtccgcct ttctcccttc gggaagcgtg gcgctttctc atagctcacg   9660
ctgtaggtat ctcagttcgg tgtaggtcgt tcgctccaag ctgggctgtg tgcacgaacc   9720
ccccgttcag cccgaccgct gcgccttatc cggtaactat cgtcttgagt ccaacccggt   9780
aagacacgac ttatcgccac tggcagcagc cactggtaac aggattagca gagcgaggta   9840
tgtaggcggt gctacagagt tcttgaagtg gtggcctaac tacggctaca ctagaaggac   9900
agtatttggt atctgcgctc tgctgaagcc agttaccttc ggaaaaagag ttggtagctc   9960
ttgatccggc aaacaaacca ccgctggtag cggtggtttt tttgtttgca agcagcagat  10020
tacgcgcaga aaaaaggat ctcaagaaga tcctttgatc ttttctacgg ggtctgacgc   10080
tcagtggaac gaaaactcac gttaagggat tttggtcatg agattatcaa aaaggatctt  10140
cacctagatc cttttaaatt aaaaatgaag ttttaaatca atctaaagta tatatgagta  10200
aacttggtct gacagttacc aatgcttaat cagtgaggca cctatctcag cgatctgtct  10260
atttcgttca tccatagttg cctgactccc cgtcgtgtag ataactacga tacgggaggg  10320
cttaccatct ggccccagtg ctgcaatgat accgcgagac ccacgctcac cggctccaga  10380
tttatcagca ataaaccagc cagccggaag ggccgagcgc agaagtggtc ctgcaacttt  10440
atccgcctcc atccagtcta ttaattgttg ccgggaagct agagtaagta gttcgccagt  10500
taatagtttg cgcaacgttg ttgccattgc tacaggcatc gtggtgtcac gctcgtcgtt  10560
tggtatggct tcattcagct ccggttccca acgatcaagg cgagttacat gatcccccat  10620
gttgtgcaaa aaagcggtta gctccttcgg tcctccgatc gttgtcagaa gtaagttggc  10680
cgcagtgtta tcactcatgg ttatggcagc actgcataat tctcttactg tcatgccatc  10740
cgtaagatgc ttttctgtga ctggtgagta ctcaaccaag tcattctgag aatagtgtat  10800
gcggcgaccg agttgctctt gcccggcgtc aatacgggat aataccgcgc cacatagcag  10860
aactttaaaa gtgctcatca ttggaaaacg ttcttcgggg cgaaaactct caaggatctt  10920
accgctgttg agatccagtt cgatgtaacc cactcgtgca cccaactgat cttcagcatc  10980
ttttactttc accagcgttt ctgggtgagc aaaaacagga aggcaaaatg ccgcaaaaaa  11040
gggaataagg gcgacacgga aatgttgaat actcatactc ttcctttttc aatattattg  11100
aagcatttat cagggttatt gtctcatgag cggatacata tttgaatgta tttagaaaaa  11160
taaacaaata ggggttccgc gcacatttcc ccgaaaagtg ccacctaaat tgtaagcgtt  11220
aatattttgt taaaattcgc gttaaatttt tgttaaatca gctcattttt taaccaatag  11280
gccgaaatcg gcaaaatccc ttataaatca aagaataga ccgagatagg gttgagtgtt  11340
gttccagttt ggaacaagag tccactatta agaacgtgg actccaacgt caagggcga    11400 aaaccgtct atcagggcga tggcccacta cgtgaaccat caccctaatc aagttttttg   11460
gggtcgaggt gccgtaaagc actaaatcgg aaccctaaag ggagcccccg atttagagct  11520
tgacggggaa agccaacctg gcttatcgaa attaatacga ctcactatag ggagaccggc  11580
agatcttgaa taataaaatg tgtgtttgtc cgaaatacgc gt                     11622
```

VECTOR SYSTEM

REFERENCE TO RELATED APPLICATIONS

This application is a Continuation-in-Part of PCT/GB01/04433, filed on Oct. 5, 2001, designating the U.S., published on Apr. 11, 2002 as WO 02/29065, and claiming priority from GB 0024550.6, filed on Oct. 6, 2000. All of the above-mentioned applications, as well as all documents cited herein, and documents referenced or cited in documents cited herein, are incorporated by reference.

The present invention relates to a vector system. In particular, the present invention relates to a lentiviral vector system for the treatment of Parkinson's disease.

BACKGROUND

Parkinson's Disease

Parkinson's disease (PD) is a neurodegenerative disorder characterized by the loss of the nigrostriatal pathway. Although the cause of Parkinson's disease is not known, it is associated with the progressive death of dopaminergic (tyrosine hydroxylase (TH) positive) mesencephalic neurons, inducing motor impairment. The characteristic symptoms of Parkinson's disease appear when up to 70% of TH-positive nigrostriatal neurons have degenerated.

There is currently no satisfactory cure for Parkinson's disease. Symptomatic treatment of the disease-associated motor impairments involves oral administration of dihydroxyphenylalanine (L-DOPA). L-DOPA is transported across the blood-brain barrier and converted to dopamine, partly by residual dopaminergic neurons, leading to a substantial improvement of motor function. However, after a few years, the degeneration of dopaminergic neurons progresses, the effects of L-DOPA are reduced and side-effects reappear. Better therapy for Parkinson's disease is therefore necessary.

An alternative strategy for therapy is neural grafting, which is based on the idea that dopamine supplied from cells implanted into the striatum can substitute for lost nigrostriatal cells. Clinical trials have shown that mesencephalic TH positive neurons obtained from human embryo cadavers (aborted foetuses) can survive and function in the brains of patients with Parkinson's disease. However, functional recovery has only been partial, and the efficacy and reproducibility of the procedure is limited. Also, there are ethical, practical and safety issues associated with using tissue derived from aborted human foetuses. Moreover, the large amounts of tissue required to produce a therapeutic effect is likely to prove to be prohibitive. Some attempts have been made to use TH positive neurons from other species (in order to circumvent some of the ethical and practical problems). However, xenotransplantation requires immunosuppressive treatment and is also controversial due to, for example, the possible risk of cross-species transfer of infectious agents. Another disadvantage is that, in current grafting protocols, no more than 5–20% of the expected numbers of grafted TH positive neurons survive. In order to develop a practicable and effective transplantation protocol, an alternative source of TH positive neurons is required.

A further alternative strategy for therapy is gene therapy. It has been suggested that gene therapy could be used in Parkinson's disease in two ways: to replace dopamine in the affected striatum by introducing the enzymes responsible for L-DOPA or dopamine synthesis (for example, tyrosine hydroxylase); and to introduce potential neuroprotective molecules that may either prevent the TH-positive neurons from dying or stimulate regeneration and functional recovery in the damaged nigrostriatal system (Dunnet S. B. and Björklund A (1999) Nature 399 A32–A39).

In vivo, dopamine is synthesised from tyrosine by two enzymes, tyrosine hydroxylase (TH) and aromatic amino acid DOPA-decarboxylase (AADC). Parkinson's disease has been shown to be responsive to treatments that facilitate dopaminergic transmission in caudate-putamen. In experimental animals, genetically modified cells that express tyrosine hydroxylase, and thereby synthesise L-DOPA, induce behavioural recovery in rodent models of PD (Wolff et al. (1989) PNAS (USA) 86:9011–14; Freed et al (1990) Arch. Neurol. 47:505–12; Jiao et al. (1993) Nature 262: 4505).

Functional activity of tyrosine hydroxylase depends on the availability of its cofactor tetrahydrobiopterin ($BH_4$). The level of cofactor may be insufficient in the denervated striatum, and so it is thought that GTP cyclohydrolase I, the enzyme that catalyses the rate limiting step on the pathway of $BH_4$-synthesis, may also need to be transduced to obtain sufficient levels of L-DOPA production in vivo (Bencsics et al (1996) J. Neurosci 16:4449–4456; Leff et al (1998) Exp. Neurol. 151:249–264).

Although in vivo and ex vivo gene therapy strategies for the treatment of Parkinson's disease have already been proposed (Dunnet and Bjorklund (1999) as above; Raymon et al (1997) Exp. Neurol. 144:82–91; Kang (1998) Mov. Dis. 13: 59–72) significant progress in this technology has been hampered by the limited efficiency of gene transfer and expression in the target cells. One problem in this regard is that the target cells are usually non-dividing cells (i.e. neurones) which are notoriously recalcitrant to transduction.

Expression of More than One Protein

WO 98/18934 relates to a a polynucleotide sequence for use in gene therapy, which polynucleotide sequence comprises two or more therapeutic genes operably linked to a promoter, and encodes a fusion protein product of the therapeutic genes. This provides a way of expressing two therapeutic genes from a single "chimeric gene". In a preferred embodiment, the polynucleotide sequence is capable of encoding a fusion protein comprising tyrosine hydroxylase and DOPA decarboxylase in either TH-DD or DD-TH order, linked by a flexible linker.

As discussed in WO/18924, amongst gene transfer systems, retroviral vectors hold substantial promise for gene therapy. These systems can transfer genes efficiently and new vectors are emerging that are particularly useful for gene delivery to brain cells (Naldini et al., 1996 Science 272, 263). However, it is dear from the literature that retroviral vectors achieve the highest titres and most potent gene expression properties if they are kept genetically simple (PCT/GB96/01230; Bowtell et al., 1988 J. Virol. 62, 2464; Correll et al., 1994 Blood 84, 1812; Emerman and Temin 1984 Cell 39, 459; Ghattas et al., 1991 Mol. Cell. Biol. 11, 5848; Hantzopoulos et al., 1989 PNAS 86, 3519; Hatzoglou et al., 1991 J. Biol. Chem 266, 8416; Hatzoglou et al., 1988 J. Biol. Chem 263, 17798; Li et al., 1992 Hum. Gen. Ther. 3, 381; McLachlin et al., 1993 Virol. 195, 1; Overell et al., 1988 Mol. Cell Biol. 8, 1803; Scharfman et al., 1991 PNAS 88, 4626; Vile et al., 1994 Gene Ther 1, 307; Xu et al., 1989 Virol. 171, 331; Yee et al., 1987 PNAS 84, 5197). This means using a single transcription unit within the vector genome and orchestrating appropriate gene expression from sequences either within the 5' LTR or from an internal promoter using a self-inactivating LTR, or using the split-intron technology described in the WO99/15683.

According to WO 98/18934, if there is a need to express two proteins from a single retroviral vector it is preferable to express them as a fusion protein (encoded by a single nucleotide sequence) than to use an internal ribosome entry site (IRES) to initiate translation of the second coding sequence in a poly-cistronic message. This is because, according to WO 98/18934 the efficiency of an IRES is often low and tissue dependent making the strategy undesirable when one is seeking to maximise the efficiency of metabolic conversion of, for example, tyrosine through to dopamine.

When located between open reading frames in an RNA, an IRES allows translation of the downstream open reading frame by promoting entry of the ribosome at the IRES element followed by downstream initiation of translation. The use of IRES elements in retroviral vectors has been investigated (see, for example, WO 93/0314) but expression of the cDNA situated downstream of the IRES has often been found to be inefficient. This may be due to competition for ribosomes and other cellular factors. The efficiency of translation initiation would therefore be expected to decrease with increasing numbers of IRES elements.

Expression of Large Heterologous Genes

Although the concept of using viral vectors to deliver a heterologous gene to a recipient cell is well known (Verma and Somia (1997) Nature 389:239–242), it is widely accepted that there are limits on the size of the heterologous gene which can be successfully transduced (see, for example page 446, Chapter 9 of Coffin et al "Retroviruses" 1997 Cold Spring Harbour Laboratory Press). If incorporation of the heterologous gene and associated regulatory elements dramatically increases the size of the viral genome, then there is a significant risk that it will no longer be able to be successfully packaged, or at least that packaging efficiency will be significantly reduced.

Despite the apparent prejudice in the art, the present inventors have shown that lentiviral vectors expressing a bicistronic cassette (encoding TH and GTP-CH1) and even a tricistronic cassette (encoding TH, AADC and GTP-CH1) can yield expression of the appropriate enzymes in heterologous cells in culture and in vivo. Incorporation of the tricistronic cassette into the lentiviral vector causes an increase in the size of the RNA genome of approximately 10%–30% (over the wild-type RNA genome) but surprisingly, gene transfer efficiency is not markedly affected. Integration efficiencies are comparable and efficient gene transfer to neurons is demonstrated. Moreover, the inventors have shown that such vectors may be used to increase the levels of certain catecholamines in denervated tissue and therefore correct rodent and primate models of Parkinson's disease.

SUMMARY OF THE INVENTION

The first aspect of the invention relates to viral vector genomes. In a first embodiment of the first aspect of the invention there is provided a retroviral vector genome comprising two or more NOIs (nucleotide sequences of interest) operably linked by one or more Internal Ribosome Entry Site(s). Preferably the genome comprises three or more NOIs operably linked by two or more Internal Ribosome Entry Site(s). Preferably each NOI is useful in the treatment of a neurodegenerative disorder. Preferably the genome is a lentiviral vector genome.

In a second embodiment of the first aspect of the invention there is provided a lentiviral vector genome comprising two or more NOIs suitable for treating a neurodegenerative disorder. Preferably the genome comprises three or more NOIs suitable for treating a neurodegenerative disorder. Preferably the NOIs are operably linked by one or more Internal Ribosome Entry Sites(s).

Preferably the NOIs of these first and second embodiments of the invention are capable of encoding a protein selected from the following group: Tyrosine Hydroxylase, GTP-cyclohydrolase I, Aromatic Amino Acid Dopa Decarboxylase and Vesicular Monoamine Transporter 2 (VMAT2). More preferably the NOIs are capable of encoding Tyrosine Hydroxylase, GTP-cyclohydrolase I and optionally Aromatic Amino Acid Dopa Decarboxylase or Aromatic Amino Acid Dopa Decarboxylase and Vesicular Monoamine Transporter 2. The NOIs of the embodiments may also encode proteins such as growth factors and antibodies.

In a third embodiment of the first aspect of the invention there is provided a lentiviral vector genome capable of encoding tyrosine hydroxylase and GTP-cyclohydrolase I. Preferably the genome is also capable of encoding Aromatic Amino Acid Dopa Decarboxylase or Aromatic Amino Acid Dopa Decarboxylase and Vesicular Monoamine Transporter 2. Preferably the enzymes are encoded by NOIs, which are operably linked by one or more Internal Ribosome Entry sites.

The second aspect of the invention relates to vector systems.

In a first embodiment of the second aspect of the invention there is provided a vector system comprising a genome according to the first aspect of the invention.

In a second embodiment of the second aspect of the invention there is provided a lentiviral vector system which is capable of delivering an RNA genome to a recipient cell, wherein the genome is longer than the wild type genome of the lentivirus. Preferably the lentiviral vector system is an EIAV vector system.

According to further aspects of the invention, there is provided:

a method for producing a lentiviral particle which comprises introducing such a viral genome into a producer cell;

a viral particle produced by such a system or method;

a pharmaceutical composition comprising such a genome, system or particle;

the use of such a genome, system or particle in the manufacture of a pharmaceutical composition to treat and/or prevent a disease;

a cell which has been transduced with such a system;

a method of treating and/or preventing a disease by using such a genome, system, viral particle or cell;

According to a yet further aspect there is provided a bicistronic cassette comprising a nucleotide sequence capable of encoding tyrosine hydroxylase and a nucleotide sequence capable of encoding GTP-cyclohydrolase I operably linked by one or more IRES(s). There is also provided a bicistronic cassette encoding Aromatic Amino Acid Dopa Decarboxylase and Vesicular Monoamine Transporter 2.

According to a yet further aspect there is provided a tricistronic cassette comprising a nucleotide sequence capable of encoding tyrosine hydroxylase, a nucleotide sequence capable of encoding GTP-cyclohydrolase I and a nucleotide sequence capable of encoding Aromatic Amino Acid Dopa Decarboxylase operably linked by two or more IRES(s).

DETAILED DESCRIPTION OF THE INVENTION

The first aspect of the invention relates to retroviral and lentiviral vector genomes.

Retroviruses

The concept of using viral vectors for gene therapy is well known (Verma and Somia (1997) Nature 389:239–242).

There are many retroviruses. For the present application, the term "retrovirus" includes: murine leukemia virus (MLV), human immunodeficiency virus (HIV), equine infectious anaemia virus (EIAV), mouse mammary tumour virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV) and all other retroviridiae including lentiviruses.

A detailed list of retroviruses may be found in Coffin et al ("Retroviruses" 1997 Cold Spring Harbour Laboratory Press Eds: J M Coffin, S M Hughes, H E Varmus pp 758–763).

Lentiviruses also belong to the retrovirus family, but they can infect both dividing and non-dividing cells (Lewis et al (1992) EMBO J. 3053–3058).

The lentivirus group can be split into "primate" and "non-primate". Examples of primate lentiviruses include the human immunodeficiency virus (HIV), the causative agent of human acquired immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anaemia virus (EIAV) and the more recently described feline immunodeficiency virus (FIV) and bovine immunodeficiency virus (BIV).

Details on the genomic structure of some lentiviruses may be found in the art. By way of example, details on HIV and EIAV may be found from the NCBI Genbank database (i.e. Genome Accession Nos. AF033819 and AF033820 respectively). Details of HIV variants may also be found at http://hiv-web.lanl.gov. Details of EIAV variants may be found through http://www.ncbi.nlm.nih.gov.

During the process of infection, a retrovirus initially attaches to a specific cell surface receptor. On entry into the susceptible host cell, the retroviral RNA genome is then copied to DNA by the virally encoded reverse transcriptase which is carried inside the parent virus. This DNA is transported to the host cell nucleus where it subsequently integrates into the host genome. At this stage, it is typically referred to as the provirus. The provirus is stable in the host chromosome during cell division and is transcribed like other cellular genes. The provirus encodes the proteins and other factors required to make more virus, which can leave the cell by a process sometimes called "budding".

Each retroviral genome comprises genes called gag, pol and env which code for virion proteins and enzymes. These genes are flanked at both ends by regions called long terminal repeats (LTRs). The LTRs are responsible for proviral integration, and transcription. They also serve as enhancer-promoter sequences. In other words, the LTRs can control the expression of the viral genes. Encapsidation of the retroviral RNAs occurs by virtue of a psi sequence located at the 5' end of the viral genome.

The LTRs themselves are identical sequences that can be divided into three elements, which are called U3, R and U5. U3 is derived from the sequence unique to the 3' end of the RNA. R is derived from a sequence repeated at both ends of the RNA and U5 is derived from the sequence unique to the 5'end of the RNA. The sizes of the three elements can vary considerably among different retroviruses.

For the viral genome, the site of transcription initiation is at the boundary between U3 and R in the left hand side LTR and the site of poly (A) addition (termination) is at the boundary between R and U5 in the right hand side LTR. U3 contains most of the transcriptional control elements of the provirus, which include the promoter and multiple enhancer sequences responsive to cellular and in some cases, viral transcriptional activator proteins. Some retroviruses have any one or more of the following genes that code for proteins that are involved in the regulation of gene expression: tat, rev, tax and rex.

With regard to the structural genes gag, pol and env themselves, gag encodes the internal structural protein of the virus. Gag protein is proteolytically processed into the mature proteins MA (matrix), CA (capsid) and NC (nucleocapsid). The pol gene encodes the reverse transcriptase (RT), which contains DNA polymerase, associated RNase H and integrase (IN), which mediate replication of the genome. The env gene encodes the surface (SU) glycoprotein and the transmembrane (TM) protein of the virion, which form a complex that interacts specifically with cellular receptor proteins. This interaction leads ultimately to infection by fusion of the viral membrane with the cell membrane.

Retroviruses may also contain "additional" genes which code for proteins other than gag, pol and env. Examples of additional genes include in HIV, one or more of vif, vpr, vpx, vpu, tat, rev and nef. EIAV has, for example, the additional genes S2 and dUTPase.

Proteins encoded by additional genes serve various functions, some of which may be duplicative of a function provided by a cellular protein. In EIAV, for example, tat acts as a transcriptional activator of the viral LTR. It binds to a stable, stem-loop RNA secondary structure referred to as TAR. Rev regulates and co-ordinates the expression of viral genes through rev-response elements (RRE). The mechanisms of action of these two proteins are thought to be broadly similar to the analogous mechanisms in the primate viruses. The function of S2 is unknown. In addition, an EIAV protein, Ttm, has been identified that is encoded by the first exon of tat spliced to the env coding sequence at the start of the transmembrane protein.

Delivery Systems

Retroviral vector systems have been proposed as a delivery system for inter alia the transfer of a NOI to one or more sites of interest The transfer can occur in vitro, ex vivo, in vivo, or combinations thereof. Retroviral vector systems have even been exploited to study various aspects of the retrovirus life cycle, including receptor usage, reverse transcription and RNA packaging (reviewed by Miller, 1992 Curr Top Microbiol Immunol 158:1–24).

A recombinant retroviral vector particle is capable of transducing a recipient cell with an NOI. Once within the cell the RNA genome from the vector particle is reverse transcribed into DNA and integrated into the DNA of the recipient cell.

As used herein, the term "vector genome" refers to both to the RNA construct present in the retroviral vector particle and the integrated DNA construct. The term also embraces a separate or isolated DNA construct capable of encoding such an RNA genome. A retroviral or lentiviral genome should comprise at least one component part derivable from a retrovirus or a lentivirus. The term "derivable" is used in its normal sense as meaning a nucleotide sequence or a part thereof which need not necessarily be obtained from a virus such as a lentivirus but instead could be derived therefrom. By way of example, the sequence may be prepared synthetically or by use of recombinant DNA techniques. Preferably the genome comprises a psi region (or an analogous component which is capable of causing encapsidation).

The viral vector genome is preferably "replication defective" by which we mean that the genome does not comprise sufficient genetic information alone to enable independent replication to produce infectious viral particles within the recipient cell. In a preferred embodiment, the genome lacks a functional env, gag or pol gene.

The viral vector genome may comprise some or all of the long terminal repeats (LTRs). Preferably the genome comprises at least part of the LTRs or an analogous sequence which is capable of mediating proviral integration, and transcription. The sequence may also comprise or act as an enhancer-promoter sequence.

The viral vector genome of the first aspect of the invention may be provided as a kit of parts. For example, the kit may comprise (i) a plasmid or plasmids containing the NOIs and IRES sequence(s); and (ii) a retroviral genome construct with suitable restriction enzyme recognition sites for cloning the NOIs and IRES(s) into the viral genome.

It is known that the separate expression of the components required to produce a retroviral vector particle on separate DNA sequences cointroduced into the same cell will yield retroviral particles carrying defective retroviral genomes that carry therapeutic genes (e.g. Reviewed by Miller 1992). This cell is referred to as the producer cell (see below).

There are two common procedures for generating producer cells. In one, the sequences encoding retroviral Gag, Pol and Env proteins are introduced into the cell and stably integrated into the cell genome; a stable cell line is produced which is referred to as the packaging cell line. The packaging cell line produces the proteins required for packaging retroviral RNA but it cannot bring about encapsidation due to the lack of a psi region. However, when a vector genome according to the first aspect of the invention (having a psi region) is introduced into the packaging cell line, the helper proteins can package the psi-positive recombinant vector RNA to produce the recombinant virus stock. This can be used to transduce the NOI into recipient cells. The recombinant virus whose genome lacks all genes required to make viral proteins can infect only once and cannot propagate. Hence, the NOI is introduced into the host cell genome without the generation of potentially harmful retrovirus. A summary of the available packaging lines is presented in "Retroviruses" (1997 Cold Spring Harbour Laboratory Press Eds: J M Coffin, S M Hughes, H E Varmus pp 449).

The present invention also provides a packaging cell line comprising a viral vector genome of the first aspect of the invention. For example, the packaging cell line may be transduced with a viral vector system comprising the genome or transfected with a plasmid carrying a DNA construct capable of encoding the RNA genome. The present invention also provides a retroviral (or lentiviral) vector particle produced by such a cell.

The second approach is to introduce the three different DNA sequences that are required to produce a retroviral vector particle i.e. the env coding sequences, the gag-pol coding sequence and the defective retroviral genome containing one or more NOIs into the cell at the same time by transient transfection and the procedure is referred to as transient triple transfection (Landau & Littman 1992; Pear et al 1993). The triple transfection procedure has been optimised (Soneoka et al 1995; Finer et al 1994). WO 94/29438 describes the production of producer cells in vitro using this multiple DNA transient transfection method.

The components of the viral system which are required to complement the vector genome may be present on one or more "producer plasmids" for transfecting into cells.

The present invention also provides a vector system, comprising
(i) a viral genome according to the first aspect of the invention;
(ii) a nucleotide sequence coding for lentiviral gag and pol proteins;
(iii) nucleotide sequences encoding other essential viral packaging components not encoded by the nucleotide sequence of ii). In a preferred embodiment, the nucleotide sequence of (iii) is capable of encoding an env protein. The present invention also provides a cell transfected with such a vector system and a retroviral vector particle produced by such a cell. Preferably the gag-pol sequence is codon optimised for use in the particular producer cell (see below).

The env protein encoded by the nucleotide sequence of iii) may be a homologous retroviral or lentiviral env protein. Alternatively, it may be a heterologous env, or an env from a non-retro or lentivirus (see below under "pseudotyping").

The term "viral vector system" is used generally to mean a kit of parts which can be used when combined with other necessary components for viral particle production to produce viral particles in host cells. For example, the retroviral vector genome may lack one or more of the genes needed for viral replication. This may be combined in a kit with a further complementary nucleotide sequence or sequences, for example on one or more producer plasmids. By cotransfection of the genome together with the producer plasmid(s), the necessary components should be provided for the production of infectious is viral particles.

Alternatively, the complementary nucleotide sequence(s) may be stably present within a packaging cell line that is included in the kit.

The present invention also relates to a lentiviral vector system which is capable of delivering an RNA genome to a recipient cell, wherein the genome is longer than the wild type genome of the lentivirus. The vector system may, for example, be an EIAV vector system.

Preferably the RNA genome of the vector system has up to 5%, more preferably up to 10% or even up to 30% more bases than the wild-type genome. Preferably the RNA genome is about 10% longer than the wild-type genome. For example, wild type EIAV comprises an RNA genome of approximately 8 kb. An EIAV vector system of the present invention may have an RNA genome of up to (preferably about) 8.8 kb.

Preferably the retroviral vector system of the present invention is a self-inactivating (SIN) vector system.

By way of example, self-inactivating retroviral vector systems have been constructed by deleting the transcriptional enhancers or the enhancers and promoter in the U3 region of the 3' LTR. After a round of vector reverse transcription and integration, these changes are copied into both the 5' and the 3' LTRs producing a transcriptionally inactive provirus. However, any promoter(s) internal to the LTRs in such vectors will still be transcriptionally active. This strategy has been employed to eliminate effects of the enhancers and promoters in the viral LTRs on transcription from internally placed genes. Such effects include increased transcription or suppression of transcription. This strategy can also be used to eliminate downstream transcription from the 3' LTR into genomic DNA. This is of particular concern in human gene therapy where it may be important to prevent the adventitious activation of an endogenous oncogene. Yu et al., (1986) PNAS 83: 3194–98; Marty et al., (1990) Biochimie 72: 885–7; Naviaux et al., (1996) J. Virol. 70: 5701–5; Iwakuma et al., (1999) Virol. 261: 120–32; Deglon et al., (2000) Human Gene Therapy 11: 179–90.

Preferably a recombinase assisted mechanism is used which facilitates the production of high titre regulated lentiviral vectors from the producer cells of the present invention.

As used herein, the term "recombinase assisted system" includes but is not limited to a system using the Cre recombinase/loxP recognition sites of bacteriophage P1 or the site-specific FLP recombinase of *S. cerevisiae* which catalyses recombination events between 34 bp FLP recognition targets (FRTs).

The site-specific FLP recombinase of *S. cerevisiae* which catalyses recombination events between 34 bp FLP recognition targets (FRTs) has been configured into DNA constructs in order to generate high level producer cell lines using recombinase-assisted recombination events (Karreman et al (1996) NAR 24:1616–1624). A similar system has been developed using the Cre recombinase/loxP recognition sites of bacteriophage P1 (Vanin et al (1997) J. Virol 71:7820–7826). This was configured into a lentiviral genome such that high titre lentiviral producer cell lines were generated.

By using producer/packaging cell lines, it is possible to propagate and isolate quantities of retroviral vector particles (e.g. to prepare suitable titres of the retroviral vector particles) for subsequent transduction of, for example, a site of interest (such as adult brain tissue). Producer cell lines are usually better for large scale production or vector particles.

Transient transfection has numerous advantages over the packaging cell method. In this regard, transient transfection avoids the longer time required to generate stable vector-producing cell lines and is used if the vector genome or retroviral packaging components are toxic to cells. If the vector genome encodes toxic genes or genes that interfere with the replication of the host cell, such as inhibitors of the cell cycle or genes that induce apoptosis, it may be difficult to generate stable vector-producing cell lines, but transient transfection can be used to produce the vector before the cells die. Also, cell lines have been developed using transient infection that produce vector titre levels that are comparable to the levels obtained from stable vector-producing cell lines (Pear et al 1993, PNAS 90:8392–8396).

Producer cells/packaging cells can be of any suitable cell type. Producer cells are generally mammalian cells but can be, for example, insect cells.

As used herein, the term "producer cell" or "vector producing cell" refers to a cell which contains all the elements necessary for production of retroviral vector particles.

Preferably, the producer cell is obtainable from a stable producer cell line.

Preferably, the producer cell is obtainable from a derived stable producer cell line.

Preferably, the producer cell is obtainable from a derived producer cell line.

As used herein, the term "derived producer cell line" is a transduced producer cell line which has been screened and selected for high expression of a marker gene. Such cell lines support high level expression from the retroviral genome. The term "derived producer cell line" is used interchangeably with the term "derived stable producer cell line" and the term "stable producer cell line.

Preferably the derived producer cell line includes but is not limited to a retroviral and/or a lentiviral producer cell.

Preferably the derived producer cell line is an HIV or EIAV producer cell line, more preferably an EIAV producer cell line.

Preferably the envelope protein sequences, and nucleocapsid sequences are all stably integrated in the producer and/or packaging cell. However, one or more of these sequences could also exist in episomal form and gene expression could occur from the episome.

As used herein, the term "packaging cell" refers to a cell which contains those elements necessary for production of infectious recombinant virus which are lacking in the RNA genome. Typically, such packaging cells contain one or more producer plasmids which are capable of expressing viral structural proteins (such as codon optimised gag-pol and env) but they do not contain a packaging signal.

The term "packaging signal" which is referred to interchangeably as "packaging sequence" or "psi" is used in reference to the non-coding, cis-acting sequence required for encapsidation of retroviral RNA strands during viral particle formation. In HIV-1, this sequence has been mapped to loci extending from upstream of the major splice donor site (SD) to at least the gag start codon.

Packaging cell lines suitable for use with the above-described vector constructs may be readily prepared (see also WO 92/05266), and utilised to create producer cell lines for the production of retroviral vector particles. As already mentioned, a summary of the available packaging lines is presented in "Retroviruses" (as above).

Also as discussed above, simple packaging cell lines, comprising a provirus in which the packaging signal has been deleted, have been found to lead to the rapid production of undesirable replication competent viruses through recombination. In order to improve safety, second generation cell lines have been produced wherein the 3'LTR of the provirus is deleted. In such cells, two recombinations would be necessary to produce a wild type virus. A further improvement involves the introduction of the gag-pol genes and the env gene on separate constructs so-called third generation packaging cell lines. These constructs are introduced sequentially to prevent recombination during transfection.

Preferably, the packaging cell lines are second generation packaging cell lines.

Preferably, the packaging cell lines are third generation packaging cell lines.

In these split-construct, third generation cell lines, a further reduction in recombination may be achieved by changing the codons. This technique, based on the redundancy of the genetic code, aims to reduce homology between the separate constructs, for example between the regions of overlap in the gag-pol and env open reading frames.

The packaging cell lines are useful for providing the gene products necessary to encapsidate and provide a membrane protein for a high titre vector particle production. The packaging cell may be a cell cultured in vitro such as a tissue culture cell line. Suitable cell lines include but are not limited to mammalian cells such as murine fibroblast derived cell lines or human cell lines. Preferably the packaging cell line is a primate or human cell line, such as for example: HEK293, 293-T, TE671, HT1080.

Alternatively, the packaging cell may be a cell derived from the individual to be treated such as a monocyte, macrophage, blood cell or fibroblast. The cell may be isolated from an individual and the packaging and vector components administered ex vivo followed by re-administration of the autologous packaging cells.

It is highly desirable to use high-titre virus preparations in both experimental and practical applications. Techniques for increasing viral titre include using a psi plus packaging signal as discussed above and concentration of viral stocks.

As used herein, the term "high titre" means an effective amount of a retroviral vector or particle which is capable of transducing a target site such as a cell.

As used herein, the term "effective amount" means an amount of a regulated retroviral or lentiviral vector or vector particle which is sufficient to induce expression of the NOIs at a target site.

A high-titre viral preparation for a producer/packaging cell is usually of the order of $10^5$ to $10^7$ retrovirus particles per ml. For transduction in tissues such as the brain, it is necessary to use very small volumes, so the viral preparation is concentrated by ultracentrifugation. The resulting preparation should have at least $10^8$ t.u./ml, preferably from $10^8$ to $10^9$ t.u./ml, more preferably at least $10^9$ t.u./ml. (The titer is expressed in transducing units per ml (t.u./ml) as titred on a standard D17 cell line—see Example 9). Other methods of concentration such as ultrafiltration or binding to and elution from a matrix may be used.

The expression products encoded by the NOIs may be proteins which are secreted from the cell. Alternatively the NOI expression products are not secreted and are active within the cell. For some applications, it is preferred for the NOI expression product to demonstrate a bystander effect or a distant bystander effect; that is the production of the expression product in one cell leading to the modulation of additional, related cells, either neighbouring or distant (e.g. metastatic), which possess a common phenotype. Zennou et al., (2000) Cell 101: 173; Folleuzi et al., (2000) Nat. Genetics 25: 217; Zennou et al., (2001) Nat. Biotechnol. 19: 446.

The presence of a sequence termed the central polypurine tract (cPPT) may improve the efficiency of gene delivery to non-dividing cells. This cis-acting element is located, for example, in the EIAV polymerase coding region element. Preferably the genome of the present invention comprises a cPPT sequence.

Preferably the viral genome comprises a post-translational regulatory element. For example, the genome may comprise an element such as the woodchuck hepatitis virus posttranscriptional regulatory element (WPRE). Zufferey et al., (1999) J. Virol. 73: 2886; Barry et al., (2001) Human Gene Therapy 12: 1103.

In addition, or in the alternative, the viral genome may comprise a translational enhancer.

The NOIs may be operatively linked to one or more promoter/enhancer elements. Transcription of one or more NOIs may be under the control of viral LTRs or alternatively promoter-enhancer elements. Preferably the promoter is a strong viral promoter such as CMV, or is a cellular constitutive promoter such as PGK, beta-actin or EF1alpha. The promoter may be regulated or tissue-specific Such promoters may be selected from genes such as neurofilaments, nestin, parkin, dopamine receptors, tyrosine hydroxylase. Such promoters may also contain neurorestrictive suppressor sequences such as that found in the mu-opoid receptor gene. In a preferred embodiment, the promoter may be glial-specific or neuron-specific. The control of expression can also be achieved by using such systems as the tetracycline system that switches gene expression on or off in response to outside agents (in this case tetracycline or its analogues).

Pseudotyping

In the design of retroviral vector systems it is desirable to engineer particles with different target cell specificities to the native virus, to enable the delivery of genetic material to an expanded or altered range of cell types. One manner in which to achieve this is by engineering the virus envelope protein to alter its specificity. Another approach is to introduce a heterologous envelope protein into the vector particle to replace or add to the native envelope protein of the virus.

The term pseudotyping means incorporating in at least a part of, or substituting a part of, or replacing all of, an env gene of a viral genome with a heterologous env gene, for example an env gene from another virus. Pseudotyping is not a new phenomenon and examples may be found in WO 99/61639, WO-A-98105759, WO-A-98/05754, WO-A-97/17457, WO-A-96/09400, WO-A-91/00047 and Mebatsion et al 1997 Cell 90, 841–847.

In a preferred embodiment of the present invention the vector system is pseudotyped with a gene encoding at least part of the rabies G protein. In a further preferred embodiment of the present invention the vector system is pseudotyped with a gene encoding at least part of the VSV-G protein.

It has been demonstrated that a lentivirus minimal system can be constructed from HIV, SIV, FIV, and EIAV viruses. Such a system requires none of the additional genes vif, vpr, vpx, vpu, tat, rev and nef for either vector production or for transduction of dividing and non-dividing cells. It has also been demonstrated that an EIAV minimal vector system can be constructed which does not require S2 for either vector production or for transduction of dividing and non-dividing cells. The deletion of additional genes is highly advantageous. Firstly, it permits vectors to be produced without the genes associated with disease in lentiviral (e.g. HIV) infections. In particular, tat is associated with disease. Secondly, the deletion of additional genes permits the vector to package more heterologous DNA. Thirdly, genes whose function is unknown, such as S2, may be omitted, thus reducing the risk of causing undesired effects. Examples of minimal lentiviral vectors are disclosed in WO-A-99/32646 and in WO-A-98/17815.

Thus, preferably, the delivery system used in the invention is devoid of at least tat and S2 (if it is an EIAV vector system), and possibly also vif, vpr, vpx, vpu and net More preferably, the systems of the present invention are also devoid of rev. Rev was previously thought to be essential in some retroviral genomes for efficient virus production. For example, in the case of HIV, it was thought that rev and RRE sequence should be included. However, it has been found that the requirement for rev and RRE can be reduced or eliminated by codon optimisation (see below) or by replacement with other functional equivalent systems such as the MPMV system. As expression of the codon optimised gag-pol is REV independent, RRE can be removed from the gag-pol expression cassette, thus removing any potential for recombination with any RRE contained on the vector genome.

In a preferred embodiment the viral genome of the first aspect of the invention lacks the Rev response element (RRE).

In a preferred embodiment, the system used in the present invention is based on a so-called "minimal" system in which some or all of the additional genes have be removed.

Codon Optimisation

Codon optimisation has previously been described in WO99/41397. Different cells differ it their usage of particular codons. This codon bias corresponds to a bias in the relative abundance of particular tRNAs in the cell type. By altering the codons in the sequence so that they are tailored to match with the relative abundance of corresponding tRNAs, it is possible to increase expression. By the same token, it is possible to decrease expression by deliberately choosing codons for which the corresponding tRNAs are known to be rare in the particular cell type. Thus, an additional degree of translational control is available.

Many viruses, including HIV and other lentiviruses, use a large number of rare codons and by changing these to correspond to commonly used mammalian codons, increased expression of the packaging components in mammalian producer cells can be achieved. Codon usage tables are known in the art for mammalian cells, as well as for a variety of other organisms.

Codon optimisation has a number of other advantages. By virtue of alterations in their sequences, the nucleotide sequences encoding the packaging components of the viral particles required for assembly of viral particles in the producer cells/packaging cells have RNA instability sequences (INS) eliminated from them. At the same time, the amino acid sequence coding sequence for the packaging components is retained so that the viral components encoded by the sequences remain the same, or at least sufficiently similar that the function of the packaging components is not compromised. Codon optimisation also overcomes the Rev/RRE requirement for export, rendering optimised sequences Rev independent. Codon optimisation also reduces homologous recombination between different constructs within the vector system (for example between the regions of overlap in the gag-pol and env open reading frames). The overall effect of codon optimisation is therefore a notable increase in viral titre and improved safety.

In one embodiment only codons relating to INS are codon optimised. However, in a much more preferred and practical embodiment, the sequences are codon optimised in their entirety, with the exception of the sequence encompassing the frameshift site.

The gag-pol gene comprises two overlapping reading frames encoding gag and pol proteins respectively. The expression of both proteins depends on a frameshift during translation. This frameshift occurs as a result of ribosome "slippage" during translation. This slippage is thought to be caused at least in part by ribosome-stalling RNA secondary structures. Such secondary structures exist downstream of the frameshift site in the gag-pol gene. For HIV, the region of overlap extends from nucleotide 1222 downstream of the beginning of gag (wherein nucleotide 1 is the A of the gag ATG) to the end of gag (nt 1503). Consequently, a 281 bp fragment spanning the frameshift site and the overlapping region of the two reading frames is preferably not codon optimised. Retaining this fragment will enable more efficient expression of the gag-pol proteins.

For EIAV the beginning of the overlap has been taken to be nt 1262 (where nucleotide 1 is the A of the gag ATG). The end of the overlap is at 1461 bp. In order to ensure that the frameshift site and the gag-pol overlap are preserved, the wild type sequence has been retained from nt 1156 to 1465.

Derivations from optimal codon usage may be made, for example, in order to accommodate convenient restriction sites, and conservative amino acid changes may be introduced into the gag-pol proteins.

In a highly preferred embodiment, codon optimisation was based on highly expressed mammalian genes. The third and sometimes the second and third base may be changed.

Due to the degenerate nature of the Genetic Code, it will be appreciated that numerous gag-pol sequences can be achieved by a skilled worker. Also there are many retroviral variants described which can be used as a starting point for generating a codon optimised gag-pol sequence. Lentiviral genomes can be quite variable. For example there are many quasi-species of HIV-1 which are still functional. This is also the case for EIAV. These variants may be used to enhance particular parts of the transduction process. Examples of HIV-1 variants may be found at http://hiv-web.lanl.gov. Details of EIAV clones may be found at the NCBI database: http://www.ncbi.nlm.nih.gov.

The strategy for codon optimised gag-pol sequences can be used in relation to any retrovirus. This would apply to all lentiviruses, including EIAV, FIV, BIV, CAEV, VMR, SIV, HIV-1 and HIV-2. In addition this method could be used to increase expression of genes from HTLV-1, HTLV-2, HFV, HSRV and human endogenous retroviruses (HERV), MLV and other retroviruses.

Codon optimisation can render gag-pol expression Rev independent. In order to enable the use of anti-rev or RRE factors in the retroviral vector, however, it would be necessary to render the viral vector generation system totally Rev/RRE independent. Thus, the genome also needs to be modified. This is achieved by optimising vector genome components. Advantageously, these modifications also lead to the production of a safer system absent of all additional proteins both in the producer and in the transduced cell.

As described above, the packaging components for a retroviral vector include expression products of gag, pol and env genes. In addition, efficient packaging depends on a short sequence of 4 stem loops followed by a partial sequence from gag and env (the packaging signal). Thus, inclusion of a deleted gag sequence in the retroviral vector genome (in addition to the full gag sequence on the packaging construct) will optimise vector titre. To date efficient packaging has been reported to require from 255 to 360 nucleotides of gag in vectors that still retain env sequences, or about 40 nucleotides of gag in a particular combination of splice donor mutation, gag and env deletions. It has surprisingly been found that a deletion of all but the N-termnial 360 or so nucleotides in gag leads to an increase in vector titre. Thus, preferably, the retroviral vector genome includes a gag sequence which comprises one or more deletions, more preferably the gag sequence comprises about 360 nucleotides derivable from the N-terminus.

NOIs

In the present invention, the term NOI (nucleotide sequence of interest) includes any suitable nucleotide sequence, which need not necessarily be a complete naturally occurring DNA or RNA sequence. Thus, the NOI can be, for example, a synthetic RNA/DNA sequence, a codon optimised RNA/DNA sequence, a recombinant RNA/DNA sequence (i.e. prepared by use of recombinant DNA techniques), a cDNA sequence or a partial genomic DNA sequence, including combinations thereof. The sequence need not be a coding region. If it is a coding region, it need not be an entire coding region. In addition, the RNA/DNA sequence can be in a sense orientation or in an anti-sense orientation. Preferably, it is in a sense orientation. Preferably, the sequence is, comprises, or is transcribed from cDNA.

The NOI(s), also referred to as "heterologous sequence(s)", "heterologous gene(s)" or "transgene(s)", may be any one or more of, for example, a selection gene(s), marker gene(s) and therapeutic gene(s).

The NOI may be a candidate gene which is of potential significance in a disease process. Thus the vector system of the present invention may, for example, be used for target validation purposes.

The NOI may have a therapeutic or diagnostic application. Suitable NOIs include, but are not limited to: sequences encoding enzymes, cytokines, chemokines, hormones, antibodies, anti-oxidant molecules, engineered immunoglobulin-like molecules, a single chain antibody, fusion proteins, immune co-stimulatory molecules, immunomodulatory molecules, anti-sense RNA, a transdominant negative mutant of a target protein, a toxin, a conditional toxin, an antigen, a tumour suppresser protein and growth factors, membrane proteins, vasoactive proteins and peptides, anti-viral proteins and ribozymes, and derivatives thereof (such as with an associated reporter group). The NOIs may also encode pro-drug activating enzymes.

Preferably the NOI is useful in the treatment of a neurodegenerative disorder.

More preferably the NOI is useful in the treatment of Parkinson's disease.

The NOI may encode an enzyme involved in dopamine synthesis or storage. For example, the enzyme may be one of the following: Tyrosine Hydroxylase, GTP-cyclohydrolase I and/or Aromatic Amino Acid Dopa Decarboxylase. The sequences of all three genes are available: Accession Nos. X05290, U19523 and M76180 respecively.

Alternatively the NOI may encode the vesicular monoamine transporter 2 (VMAT2, Accession number L23205.1). In a preferred embodiment the viral genome comprises an NOI encoding Aromatic Amino Acid Dopa Decarboxylase and an NOI encoding VMAT 2. Such a genome may be used in the treatment of Parkinson's disease, in particular in conjunction with peripheral administration of L-DOPA.

Alternatively the NOI may encode a growth factor capable of blocking or inhibiting degeneration in the nigrostriatal system. An example of such a growth factor is a neurotrophic factor. For example the NOI may encode glial cell-line derived neurotrophic factor (GDNF), brain-derived neurotrophic factor (BDNF), nerve growth factor (NGF), persephin growth factor, artemin growth factor, or neurturin growth factor, cilliary neurotrophic factor (CNTF), neurotrophin-3 (NT-3), neurotrophin-4 (NT-4), pantropic neurotrophin, and other related or unrelated neurotrophic factors. WO99/14235; WO00/18799; U.S. Pat. No. 6,090,778; U.S. Pat. No. 5,834,914; WO97/08196; U.S. Pat. No. 6,090, 778; U.S. Pat. No. WO92/05254; U.S. Pat. No. 6,037,320; WO95/33829; Baumgartner, B J and Shine, H D, J. Neurosci. 17: 6504–11 (1997). In a preferred embodiment, a lentiviral vector comprises one or more of these NOIs encoding neurotrophic factors.

Alternatively the NOI may encode a neuroprotective factor. In particular, the NOI(s) may encode molecules which prevent TH-positive neurons from dying or which stimulate regeneration and functional recovery in the damaged nigrostriatal system.

The NOI may encode all or part of the protein of interest ("POI"), or a mutant, homologue or variant thereof. For example, the NOI may encode a fragment of the POI which is capable of functioning in vivo in an analogous manner to the wild-type protein.

In a highly preferred embodiment, one of the NOIs comprises a truncated form of the TH gene, lacking the regulatory domain. Such an NOI avoids feed-back inhibition by dopamine which may limit expression of the full-length enzyme.

The term "mutant" includes POIs which include one or more amino acid variations from the wild-type sequence. For example, a mutant may comprise one or more amino acid additions, deletions or substitutions. A mutant may arise naturally, or may be created artificially (for example by site-directed mutagenesis).

Here, the term "homologue" means an entity having a certain homology with the NOI, or which encodes a protein having a degree of homology with the POI. Here, the term "homology" can be equated with "identity".

In the present context, an homologous sequence is taken to include an amino acid sequence which may be at least 75, 85 or 90% identical, preferably at least 95 or 98% identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

In the present context, an homologous sequence is taken to include a nucleotide sequence which may be at least 75, 85 or 90% identical, preferably at least 95 or 98% identical to the subject sequence. Typically, the homologues will comprise the same sequences that code for the active sites etc. as the subject sequence. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate % homology between two or more sequences.

% homology may be calculated over contiguous sequences, i.e. one sequence is aligned with the other Sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software than can perform sequence comparisons include, but are not limited to, the BLAST package (see Ausubel et al., 1999 ibid—Chapter 18), FASTA (Atschul et al., 1990, J. Mol. Biol., 403–410) and the GENEWORKS suite of comparison tools. Both BLAST and FASTA are available for offline and online searching (see Ausubel et al., 1999 ibid, pages 7–58 to 7–60). However, for some applications, it is preferred to use the GCG Bestfit program. A new tool, called BLAST 2 Sequences is also available for comparing protein and nucleotide sequence (see FEMS Microbiol Lett 1999 174(2): 247–50; FEMS Microbiol Lett 1999 177(1): 187–8 and tatiana@ncbi.nlm.nih.gov).

Although the final % homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

The sequences may also have deletions, insertions or substitutions of amino add residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino adds with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| | | |
|---|---|---|
| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

The present invention also encompasses homologous substitution (substitution and replacement are both used herein to mean the interchange of an existing amino acid residue, with an alternative residue) may occur i.e. like-for-like substitution such as basic for basic, acidic for acidic, polar for polar etc. Non-homologous substitution may also occur i.e. from one class of residue to another.

Preferably the NOI encodes a single POI or a mutant, homologue or variant thereof. In a highly preferred embodiment, the NOI does not encode a fusion protein. As used herein, the term "fusion protein" is used in its conventional sense to mean an entity which comprises two or more protein activities, joined together by a peptide bond to form a single chimeric protein. A fusion protein is encoded by a single polynucleotide driven by a single promoter.

Internal Ribosome Entry Site (IRES)

The viral genome of the first aspect of the invention comprises two or more NOIs. In order for both of the NOIs to be expressed, there may be two or more transcription units within the vector genome, one for each NOI. However, it is clear from the literature that retroviral vectors achieve the highest titres and most potent gene expression properties if they are kept genetically simple (PCT/GB96/01230; Bowtell et al., 1988 J. Virol. 62, 2464; Correll et al., 1994 Blood 84, 1812; Emerman and Temin 1984 Cell 39, 459; Ghattas et al., 1991 Mol. Cell. Biol. 11, 5848; Hantzopoulos et al., 1989 PNAS 86, 3519; Hatzoglou et al., 1991 J. Biol. Chem 266, 8416; Hatzoglou et al., 1988 J. Biol. Chem 263, 17798; Li et al., 1992 Hum. Gen. Ther. 3, 381; McLachlin et al., 1993 Virol. 195, 1; Overell et al., 1988 Mol. Cell Biol. 8, 1803; Scharfman et al., 1991 PNAS 88, 4626; Vile et al., 1994 Gene Ther 1, 307; Xu et al., 1989 Virol. 171, 331; Yee et al., 1987 PNAS 84, 5197) and so it is preferable to use an internal ribosome entry site (IRES) to initiate translation of the second (and subsequent) coding sequence(s) in a polycistronic message (Adam et al 1991 J. Virol. 65, 4985).

Insertion of IRES elements into retroviral vectors is compatible with the retroviral replication cycle and allows expression of multiple coding regions from a single promoter (Adam et al (as above); Koo et al (1992) Virology 186:669–675; Chen et al 1993 J. Virol 67:2142–2148). IRES elements were first found in the non-translated 5' ends of picornaviruses where they promote cap-independent translation of viral proteins (Jang et al (1990) Enzyme 44: 292–309). When located between open reading frames in an RNA, IRES elements allow efficient translation of the downstream open reading frame by promoting entry of the ribosome at the IRES element followed by downstream initiation of translation.

A review on IRES is presented by Mountford and Smith (TIG May 1995 vol 11, No 5:179–184). A number of different IRES sequences are known including those from encephalomyocarditis virus (EMCV) (Ghattas, I. R., et al., Mol. Cell. Biol., 11:5848–5859 (1991); BiP protein [Macejak and Sarnow, Nature 353:91 (1991)]; the Antennapedia gene of *Drosophila* (exons d and e) [Oh, et al, *Genes & Development,* 6:1643–1653 (1992)] as well as those in polio virus (PV) [Pelletier and Sonenberg, *Nature* 334: 320–325 (1988); see also Mountford and Smith, TIG 11, 179–184 (1985)].

According to WO-A-97/14809, IRES sequences are typically found in the 5' non-coding region of genes. In addition to those in the literature they can be found empirically by looking for genetic sequences that affect expression and then determining whether that sequence affects the DNA (i.e. acts as a promoter or enhancer) or only the RNA (acts as an IRES sequence).

IRES elements from PV, EMCV and swine vesicular disease virus have previously been used in retroviral vectors (Coffin et al, as above).

The term "IRES" includes any sequence or combination of sequences which work as or improve the function of an IRES.

The IRES(s) may be of viral origin (such as EMCV IRES, PV IRES, or FMDV 2A-like sequences) or of cellular origin (such as FGF2 IRES, NRF IRES, Notch 2 IRES or EIF4 IRES). Examples of IRES elements and references in which they are described are set forth below.

include the use of multiple internal promoters in the vector (Overell et al., Mol Cell Biol. 8: 1803–8 (1988)), or the use of alternate splicing patterns leading to multiple RNA species derived from the single viral genome that expresses the different genes. This strategy has previously been used by itself for two genes (Cepko et al. Cell 37: 1053 (1984)).

Transduced Cells

The present invention also relates to a cell which has been transduced with a vector system comprising a viral genome according to the first aspect of the invention.

Transduction with the vector system of the present invention may confer or increase the ability of the cell to produce catecholamines. It may, for example, confer or increase the ability of the cell to convert tyrosine to L-dopa and/or L-dopa to dopamine. Release of catecholamines can be measured by techniques known in the art, for example by using an electrochemical detector connected to an analytical

| Virus/gene type | Virus/gene | Reference |
|---|---|---|
| Viral RNAs | | |
| Picornaviruses | Poliovirus (PV) | Pelletier & Sonenberg (1988) |
| | Encephalomyocarditis virus (EMCV) | Jang et al. (1988) |
| | Foot-and-mouth disease virus (FMDV) | Kühn et al. (1990) |
| Flavivirus | Hepatitus C virus (HCV) | Reynolds et al. (1995) |
| Pestivirus | Classical swine fever virus (CSFV) | Pestova et al. (1998) |
| Retrovirus | Murine leukemia virus (MLV) | Berlioz & Darlix (1995) |
| Lentivirus | Simian immunodeficiency virus (SIV) | Ohlmann et al. (2000) |
| Cellular mRNAs | | |
| Translation initiation factors | eIF4G | Johannes & Sarnow (1998) |
| | DAP5 | Henis-Korenblit et al. (2000) |
| Transcription factors | c-Myc | Stoneley et al. (2000) |
| | NF-κB-repressing factor (NRF) | Oumrad et al. (2000) |
| Growth factors | Vascular endothelial growth facter (VEGF) | Huez et al. (1998) |
| | Fibroblast growth factor 2 (FGF-2) | Vagner et al. (1995) |
| | Platelet-derived growth factor B (PDGF B) | Bernstein et al. (1997) |
| Homeotic genes | Antennapedia | Oh et al. (1992) |
| Survival proteins | Apaf-1 | Coldwell et al. (2000) |
| Miscellaneous | BiP | Macejak & Sarnow (1991) |

In order for the IRES to be capable of initiating translation of each NOI, it should be located between or prior to NOIs in the vector genome. For example, for a multicistronic sequence containing n NOIs, the genome may be as follows:

[(NOI$_1$-IRES$_1$] . . . NOI$_n$ n=1→n

For bi and tricistronic sequences, the order may be as follows:

NOI$_1$-IRES$_1$-NOI$_2$
NOI$_1$-IRES$_1$-NOI$_2$-IRES$_2$-NOI$_3$

Alternative configurations of IRESs and NOIs can also be utilised. For example transcripts containing the IRESs and NOIs need not be driven from the same promoter.

An example of this arrangement may be:

IRES$_1$-NOI$_1$-promoter-NOI$_2$-IRES$_2$-NOI$_3$.

In a preferred embodiment, in any construct utilising an internal cassette having more than one IRES and NOI, the IRESs may be of different origins, that is, heterologous to one another. For example, one IRES may be from EMCV and the other IRES may be from polio virus.

Other Methods of Expressing Multiple Genes from One Vector

Although IRESs are an efficient way to co-express multiple genes from one vector, other methods are also useful, and may be used alone or in conjunction with IRESs. These cell. In addition of the catecholamines themselves, biproducts associated with catecholamine release (such as DOPAC, a specific degradation product of dopamine) may also be detected.

The cell may be transduced in vivo, in vitro or ex vivo. For example, if the cell is a cell from a mammalian subject, the cell may be removed from the subject and transduced ready for reimplantation into the subject (ex vivo transduction). Alternatively the cell may be transduced by direct gene transfer in vivo, using the vector system of the present invention in accordance with standard techniques (such as via injection of vector stocks expressing the NOIs). If the cell is part of a cell line which is stable in culture (i.e. which can survive numerous passages and can multiple in vitro) then it may be transduced in vitro by standard techniques, for example by exposure of the cell to viral supernatants comprising vectors expressing the NOIs.

The cell may be any cell which is susceptible to transduction. If the vector system is capable of transducing non-dividing cells (for example if it is a lentiviral system) then the cell may be a non-dividing cell such as a neuron.

In a preferred embodiment the transduced cell forms part of a genetically modified neuronal cell line. Such a cell line may, for example, be transplanted into the brain for the treatment of Parkinson's disease.

In a further embodiment the cell is a neuronal stem cell. Such a cell line may, for example, be transplanted into the brain for the treatment of Parkinson's disease.

In a further embodiment the cell is a cell in the striatum of a subject, such as a neuron or glial cell. Direct gene transfer in vivo to such a cell may, for example, convert it into a dopamine-producer cell.

Cassettes

The present invention also provides multicistronic cassettes comprising two or more NOIs operably linked by an IRES. These cassettes may be used in a method for producing the vector genome in a producer cell.

The present invention also provides an expression vector comprising such a cassette. Transfection of a suitable cell with such an expression vector should result in a cell which expresses each POI encoded by the NOI in the cassette. The present invention also provides such a transfected cell.

Cloning of the cassette into an expression vector and transfection of cells with the vector (to give expression of the cassette) can be carried out by techniques well known in the art (such as those described in Sambrook et al. (Molecular Cloning: A Laboratory Manual, 2nd Edition, Cold Spring Harbor Laboratory press (1989)), and other laboratory textbooks).

Preferably the cassette comprises a promoter. In a highly preferred embodiment the cassette is bicistronic or tricistronic and comprises the following elements:

Promoter-(NOI$_1$)-(IRES$_1$)-(NOI$_2$)

Promoter-(NOI$_1$)-(IRES$_1$)-(NOI$_2$)-(IRES$_2$)-(NOI$_3$)

In a particularly preferred embodiment the cassette is bicistronic and comprises an NOI encoding tyrosine hydroxylase (or a mutant, variant or homologue thereof) and an NOI encoding GTP-cyclohydrolase I (or a mutant, variant or homologue thereof) in either order. In another particularly preferred embodiment the cassette is bicistronic and comprises an NOI encoding Aromatic Amino Acid Dopa Decarboxylase and an NOI encoding Vesicular Monoamine Transporter 2, in either order.

In another particularly preferred embodiment the cassette is tricistronic and comprises an NOI encoding tyrosine hydroxylase (or a mutant, variant or homologue thereof), an NOI encoding GTP-cyclohydrolase I (or a mutant, variant or homologue thereof) and an NOI encoding Aromatic Amino Acid Dopa Decarboxylase (or a mutant, variant or homologue thereof) in any order.

Pharmaceutical Compositions

The present invention also provides the use of a retroviral vector genome as defined in the first aspect of the invention in the manufacture of a pharmaceutical composition. The pharmaceutical composition may be used for treating an individual by gene therapy, wherein the composition comprises a therapeutically effective amount of a retroviral vector particle according to the present invention.

The pharmaceutical composition may be used to treat a human or animal subject. Preferably the subject is a mammalian subject. More preferably the subject is a human. Typically, a physician will determine the actual dosage which will be most suitable for an individual subject and it will vary with the age, weight and response of the particular patient.

The composition may optionally comprise a pharmaceutically acceptable carrier, diluent, excipient or adjuvant. The choice of pharmaceutical carrier, excipient or diluent can be selected with regard to the intended route of administration and standard pharmaceutical practice. The pharmaceutical compositions may comprise as (or in addition to) the carrier, excipient or diluent, any suitable binder(s), lubricant(s), suspending agent(s), coating agent(s), solubilising agent(s), and other carrier agents that may aid or increase the viral entry into the target site (such as for example a lipid delivery system).

Where appropriate, the pharmaceutical compositions can be administered by any one or more of: inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intracavernosally, intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

Preferably the viral vector particles of the present invention are administered by injection into the caudate putamen.

Diseases

The retroviral vector genome and vector particles of the present invention are particularly useful for the treatment and/or prevention of neurodegenerative diseases.

Diseases which may be treated include, but are not limited to: Parkinson's disease; motor-neuron disease, Huntington's disease and disorders of movement which are responsive to L-dopa, such as distonias.

In particular, the present invention is useful in treating and/or preventing Parkinson's disease.

Treatment by gene therapy with vectors capable of delivering, for example, TH, GTP-CH1 and optionally AADC or AADC and VMAT2,, is likely to be particularly useful for the late stages of PD patients which do not respond significantly to L-dopa treatment. Treatment using AADC or AADC and VMAT2, in combination with L-dopa administered peripherally may also be useful for late stage PD patients.

The present invention will now be described only by way of example, in which reference will be made to the following Figures and Tables FIG. 1: Oligonucleotide sequences of the primers (SEQ ID NOS: 8–11) used for cloning the human Tyrosine Hydroxylase Type 2 cDNA (Accession Number X05290). Restriction endonuclease recognition sites (BamHI and HindIII) appear underlined, consensus Kozak sequence in italics, and c-myo eptitope in bold.

FIG. 2: Plasmid map of pNE4. A mammalian expression plasmid derived from pcDNA3.1/Zeo that expresses the c-myc tagged human Tyrosine Hydroxylase Type 2 (cmyc-hTH).

FIG. 3: Oligonucleotide sequences of the primers (SEQ ID NOS: 12 and 13) used for cloning the human Aromatic Amino Acid Dopa Decarboxylase cDNA (Accession number M76180 M30772). Restriction endonuclease recognition sites (Bgl and HindIII) appear underlined, consensus Kozak sequence in italics, and HA epitope in bold.

Figure 4:
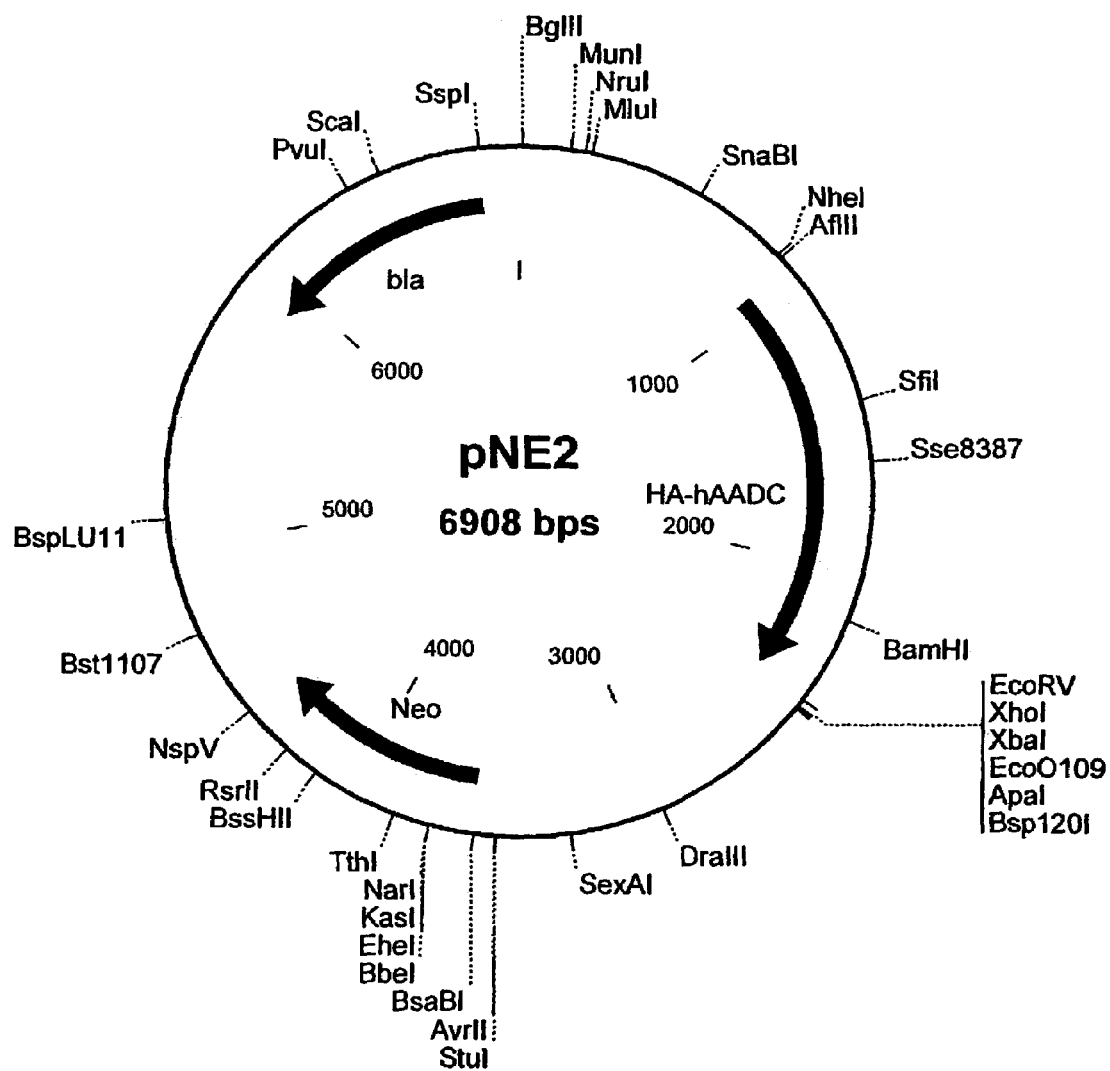

FIG. 4: Plasmid map of pNE2. A mammalian expression plasmid derived from pcDNA3.1/Neo that expresses the HA tagged human Aromatic Amino Acid Dopa Decarboxylase (HA-hAADC).

FIG. 5: Oligonucleotide sequences of the primers (SEQ ID NOS: 14 and 15) used for cloning the human GTP-cyclohydrolase 1 cDNA (Accession number U19523). Restriction endonuclease recognition sites (Bgl II and HindIII) appear underlined, consensus Kozak sequence in italics, and FLAG epitope in bold.

Figure 6:
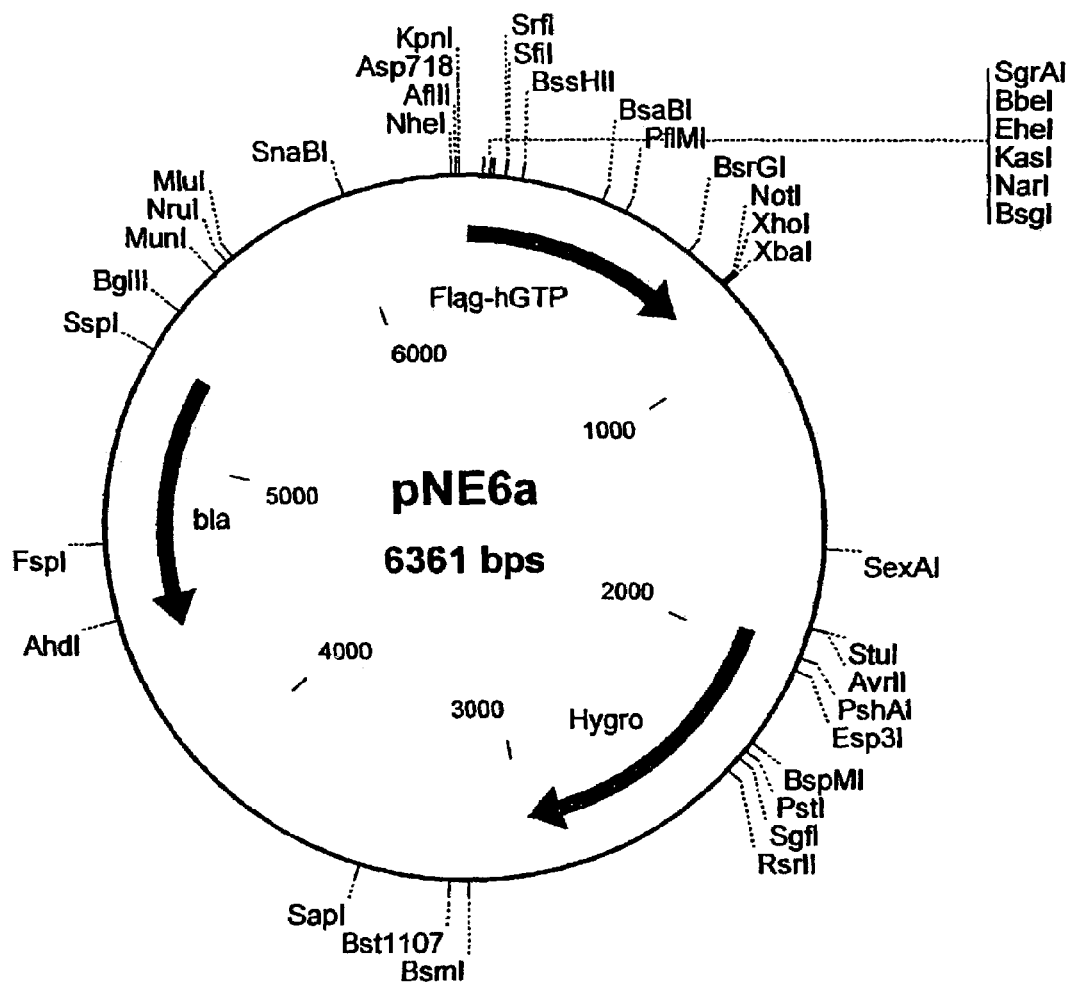

FIG. 6: Plasmid map of pNE6. A mammalian expression plasmid derived from pcDNA3.1/Hygro that expresses the FLAG tagged human GTP-cyclohydrolase 1 (FLAG-hGTP).

FIG. 7: Oligonucleotide sequences of the primers (SEQ ID NOS: 16 and 17) used for cloning a truncated form of the human Tyrosine hydroxylase Type 2. Restriction endonuclease recognition sites (BamHI, HindIII and EcoRI) appear underlined, consensus Kozak sequence in italics, and c-myc epitope in bold.

Figure 8:
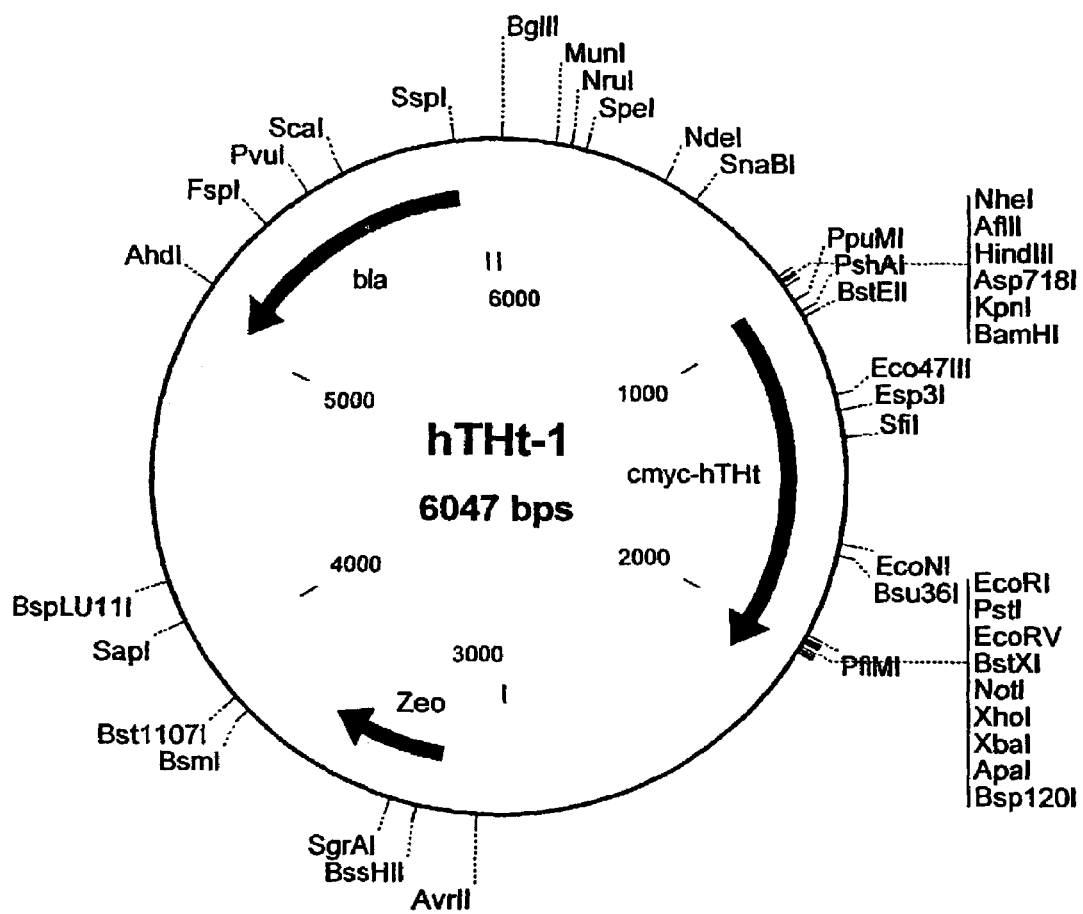

FIG. 8: Plasmid map of phTHt-1. A mammalian expression plasmid derived from pcDNA3.1/Zeo that expresses the truncated form of hTH tagged with the c-myc epitope (cmyc-hTHt).

Figure 9:
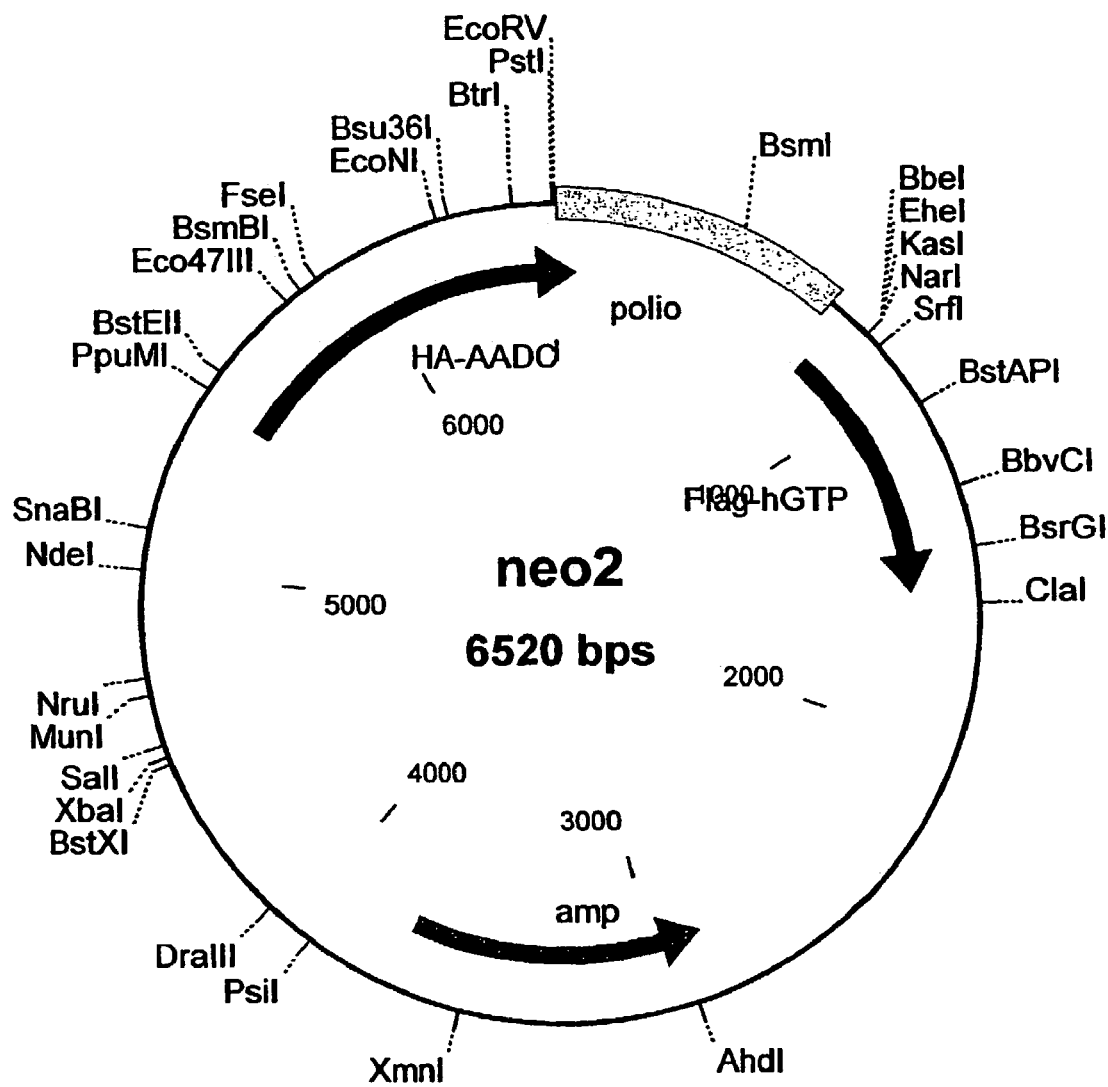

FIG. 9: Plasmid map of pneo2. A mammalian expression plasmid derived from BL-EP (Science (1995) 269:847) that expresses cmyc-hTHt and FLAG-hGTP as a bicistronic cassette. The polio virus IRES is located downstream the cmyc-hTHt gene.

Figure 10:
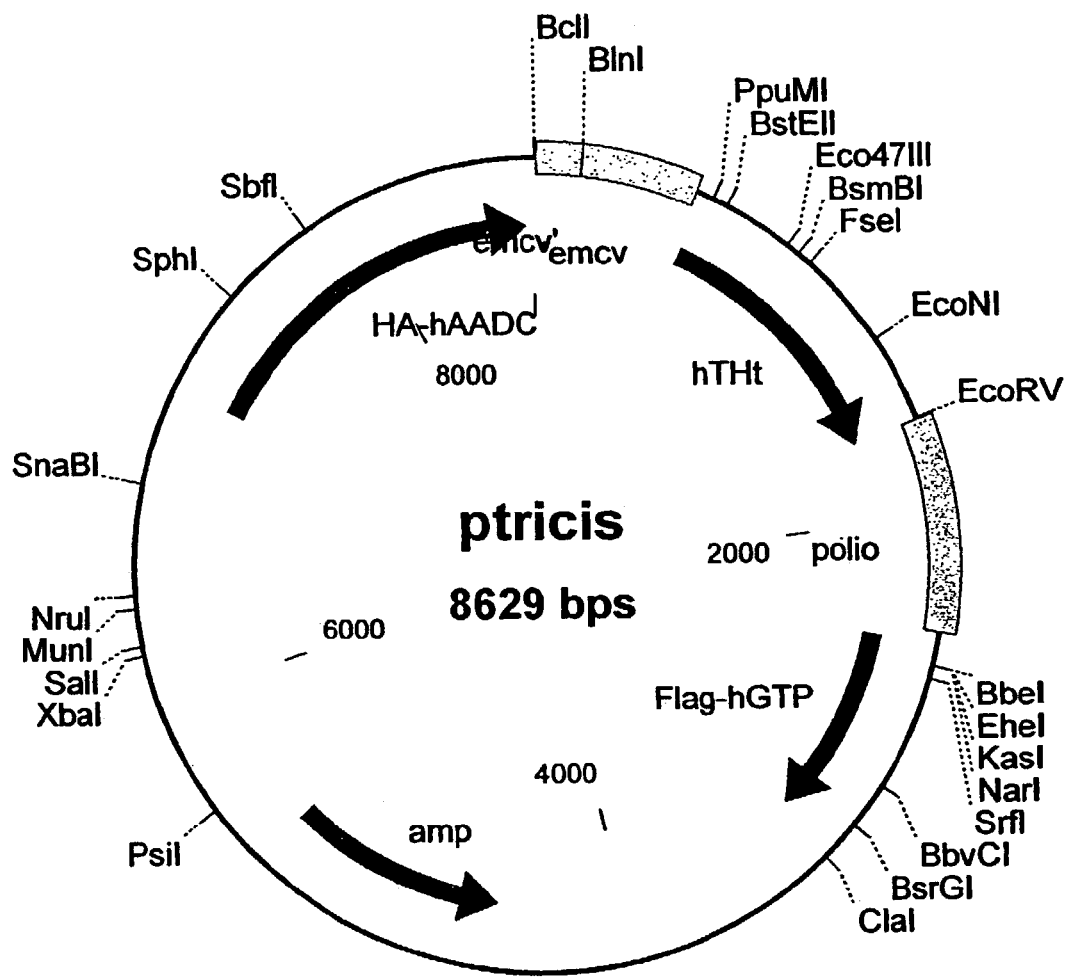

FIG. 10: Plasmid map of ptricis. A mammalian expression plasmid derived from BL-EP (Science (1995) 269:847) that expresses HA-hAADC, cmyc-hTHt and FLAG-hGTP as a tricistronic cassette. The EMCV IRES is located downstream the HA-hAADC gene and polio virus IRES downstream the cmyc-hTHt gene.

Figure 11:
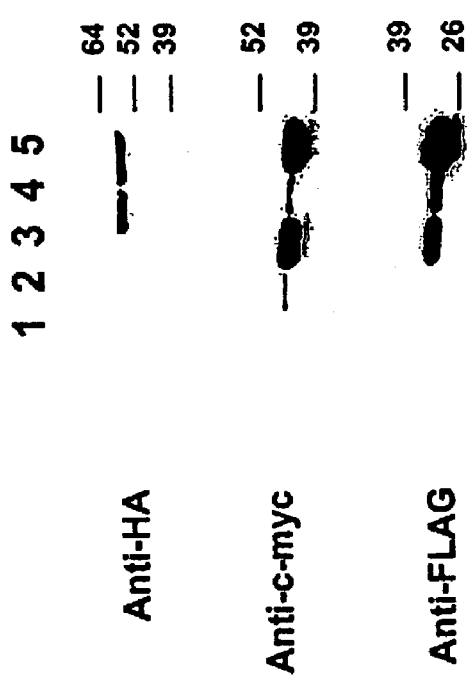

FIG. 11: Transient expression of the Bicistronic and Tricistronic cassettes in HEK 293T cells. Western Blot probed with specific mouse monoclonal antibodies. The tagged proteins bound to the antibodies are detected with a horse radish peroxidase (HRP) conjugated anti mouse rabbit IgG. Lanes; 1, Mock; 2, phTHt; 3, Bicistronic plasmid (pneo2); 4, Tricistronic plasmid (ptricis) and 5, the three monocistronic plasmids (phTHt, pNE2 and pNE6).

Figure 12:
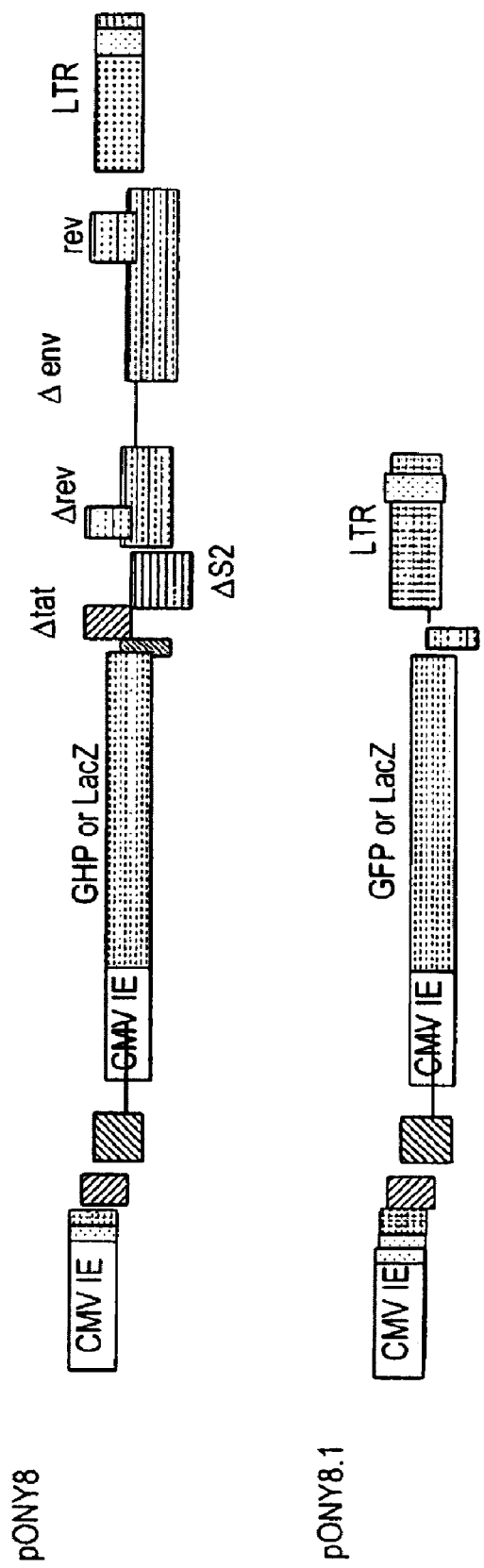

FIG. 12: A schematic diagram of EIAV minimal vectors.

Figure 13:
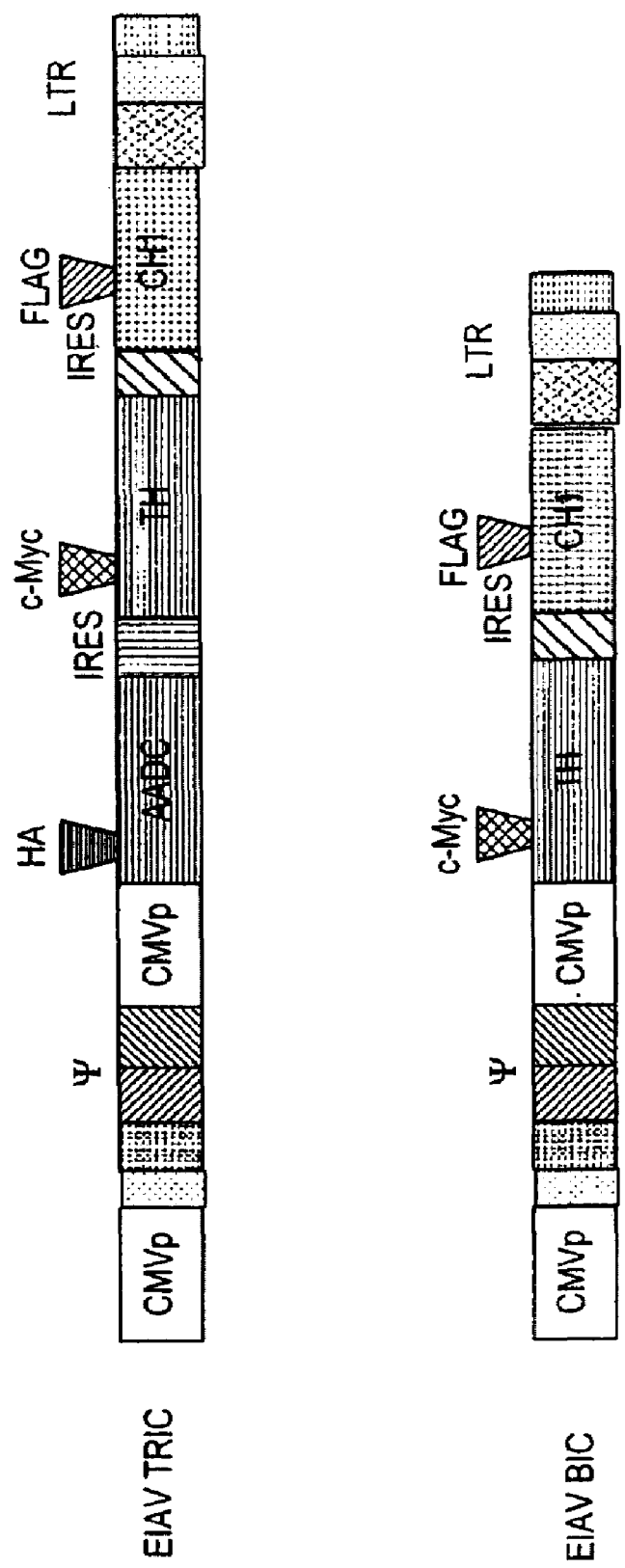

FIG. 13: A schematic diagram of EIAV BIC and EIAV TRIC vectors.

Figure 14:
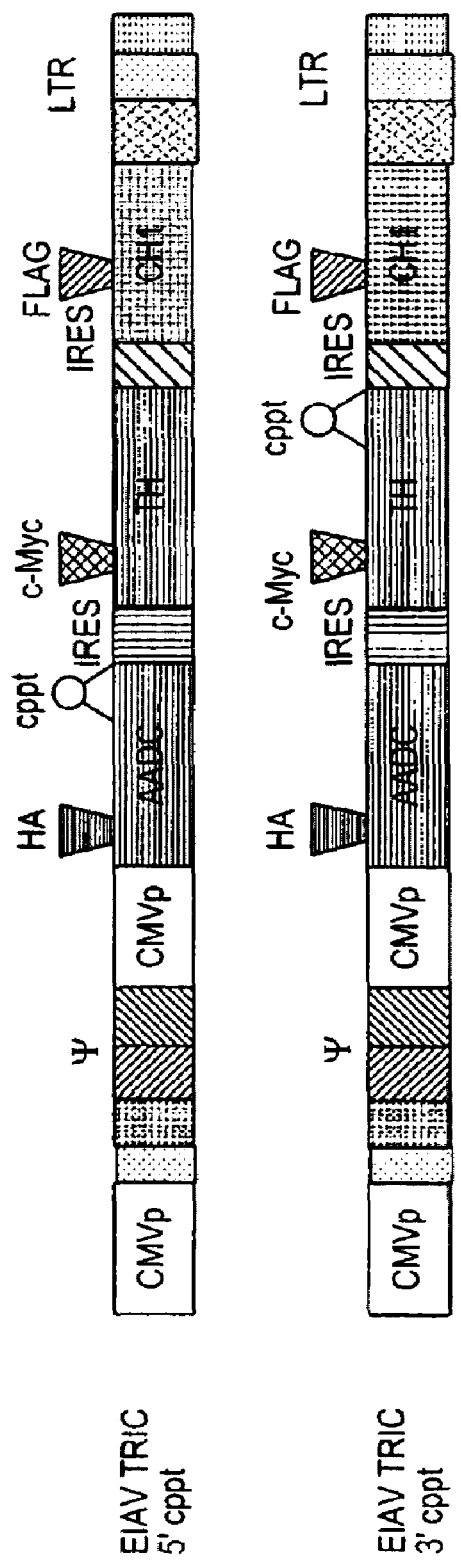

FIG. 14; A schematic diagram of EIAV TRIC vectors containing the central polypurine tract (cppt).

Figure 15:
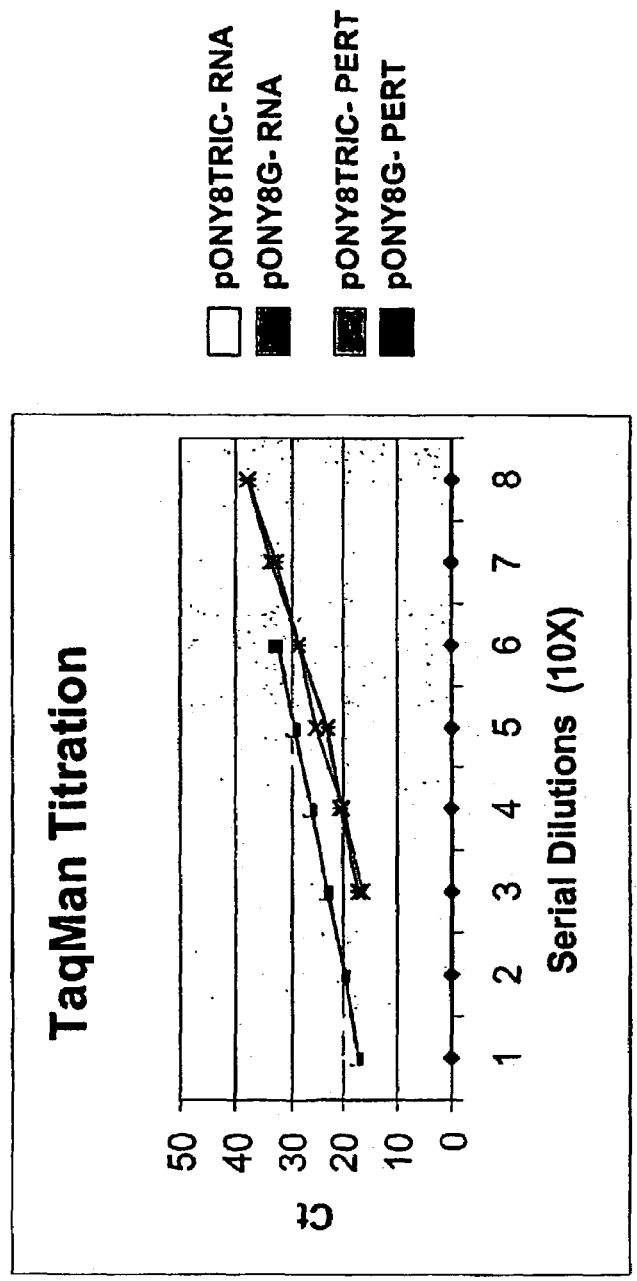

FIG. 15: PERT and viral RNA content of EIAV vectors

Figure 16:
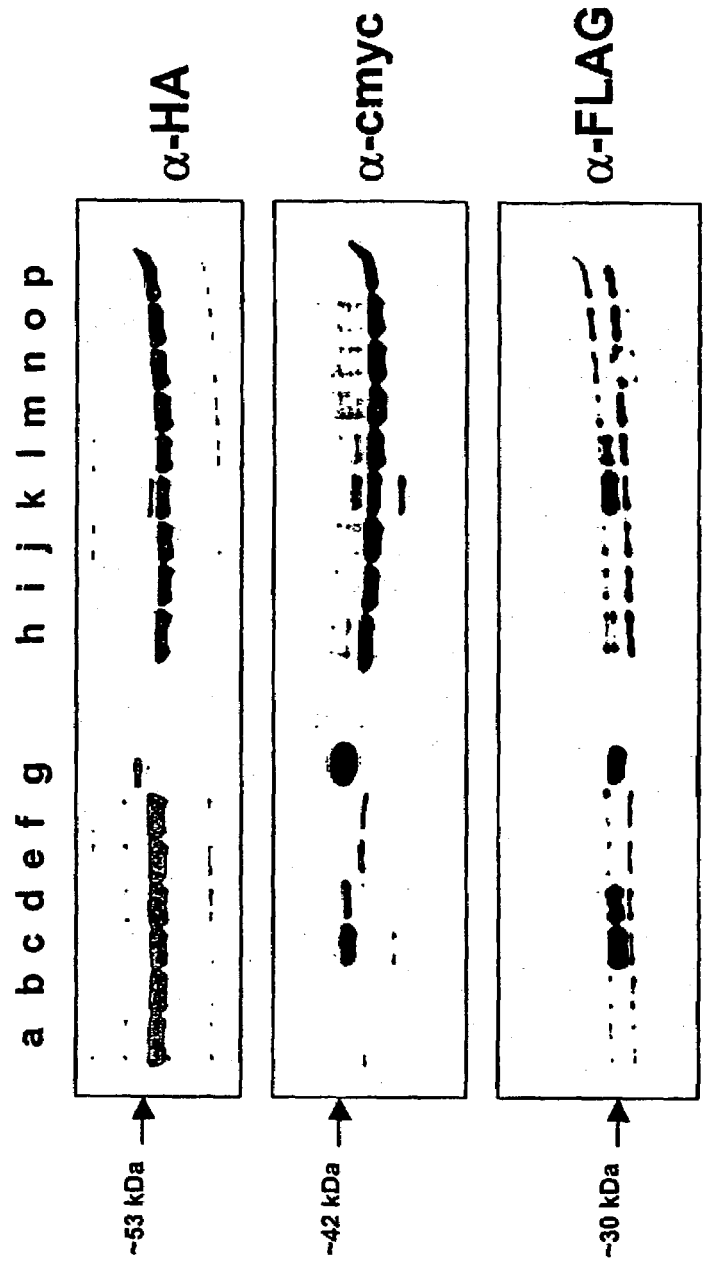

FIG. 16: Expression of EIAV BIC and EIAV TRIC vectors in D17 cells transduced at different MOIs (MOI). Western Blot probed with specific mouse monoclonal antibodies. The tagged proteins bound to the antibodies are detected with a horse radish peroxidase (HRP) conjugated anti mouse rabbit IgG. Lanes: a, pONY8G (100×); b, pONY8.1Z (100×); c, pONY8.1BIC (100×); d, pONY8.1BIC (10×); e, pONY8BIC (1×); f, untransduced cells; h, pONY8.1TRIC (100×); i, pONY8.1TRIC (10×); j, pONY8.1TRIC (1×); k, pONY8TRIC (100×); l, pONY8TRIC (10×); m, pONY8TRIC (1×); n, pONY8.1TRIC-B(100×); o, pONY8.1TRIC-B (10×); p, pONY8.1TRIC-B (1×); and g, HEK 293T cells transfected with the monocistronic plasmids (see FIG. 11).

Figure 17:
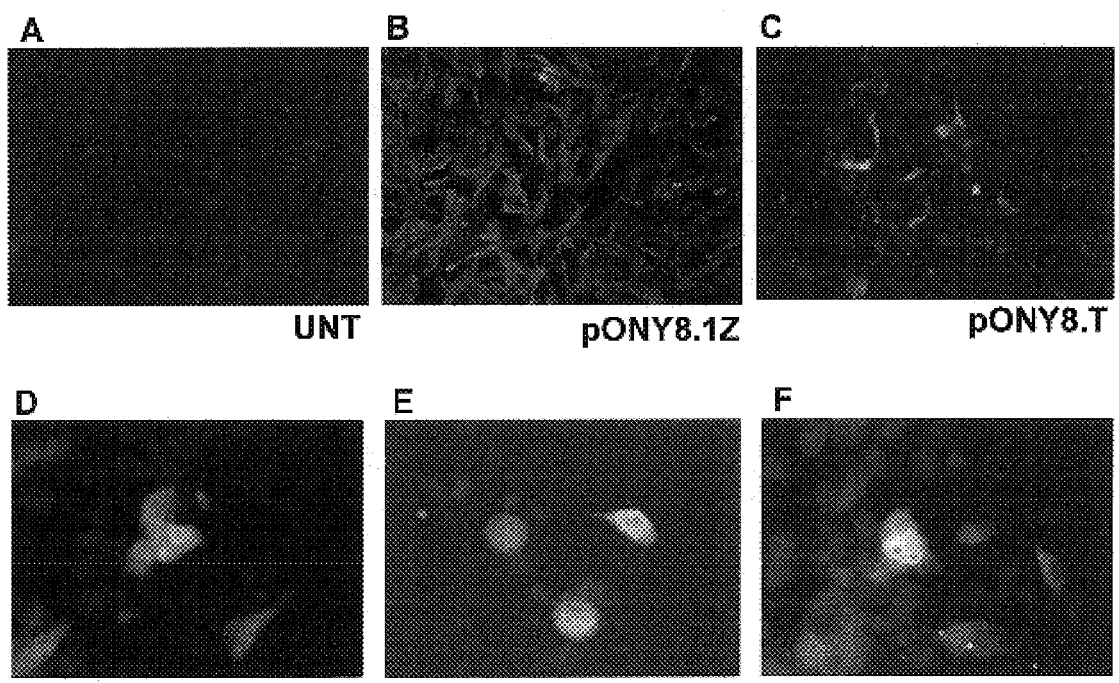

FIG. 17: Expression of EIAV TRIC vectors in D17 cells transduced at an MOI~100. FIGS. 17A–17C show immunostaing of D17 cells transduced with EIAVlacZ or EIAV TRIC vectors using rabbit polyclonal anti LacZ or mouse monoclonal anti-HA, respectively. The antibody bound to the native proteins was detected with Alexa 488 (green) conjugated to goat ant-rabbit or goat anti-mouse IgG (Magnification ~10×). FIGS. 17D–17F show immunostaining of D17 cells transduced with EIAV TRIC vectors. Immunostaining as in FIGS. 17A–17C + propidium iodide (red) that stains the nuclei (Magnification ~40×).

Figure 18:
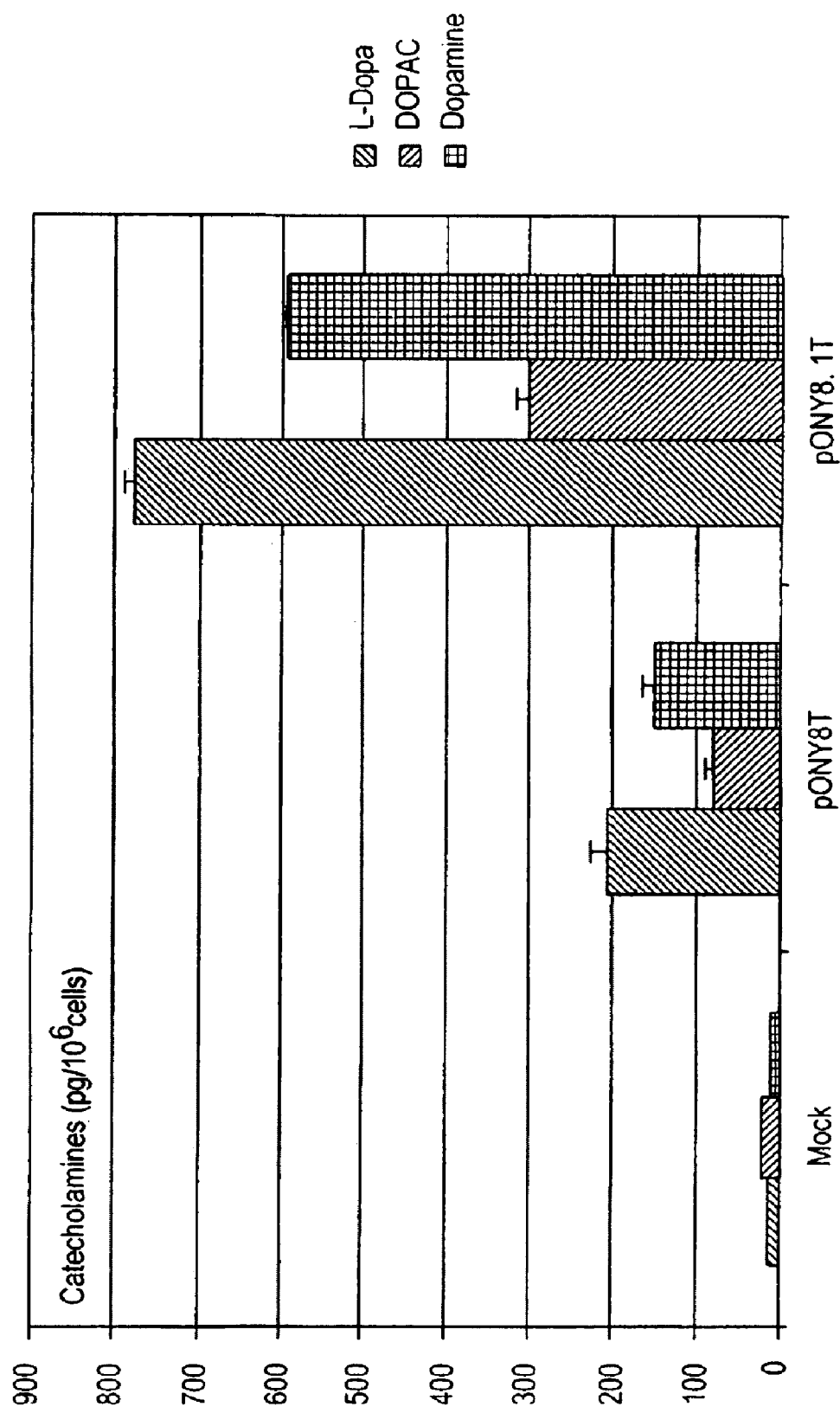

FIG. 18: Catecholamines (pg/$10^6$ cells) produced by HEK 293T cells transduced with EIAV TRIC vectors.

Figure 19:
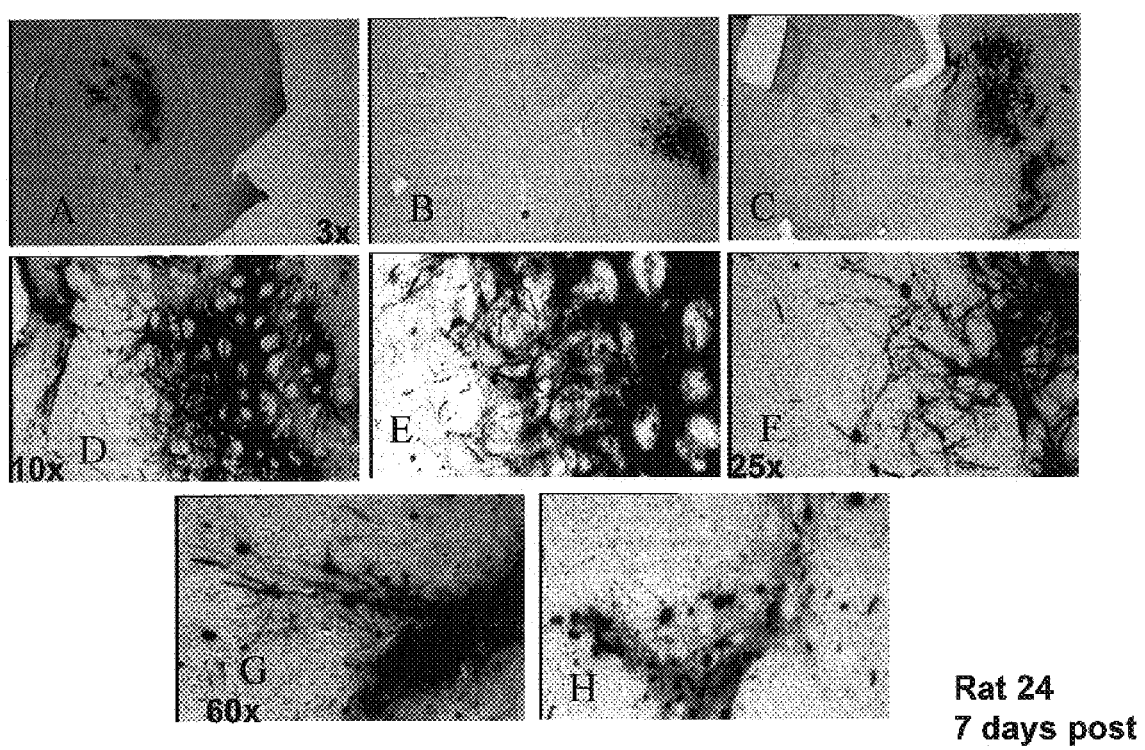

FIG. 19: Transduction of the adult rat striatum with EIAV lacZ vectors. Panels A–C correspond to 3 independent 50 μm coronal sections stained with X-gal. About fifty of such sections are stained per animal, indicating that the transduction spans the rat striatum. Panels D–H represent higher magnification of the section in C showing that many of the cells transduced have neuronal morphology both within striatum (D–F) and in nucleus accumbens (G–H).

Figure 20:
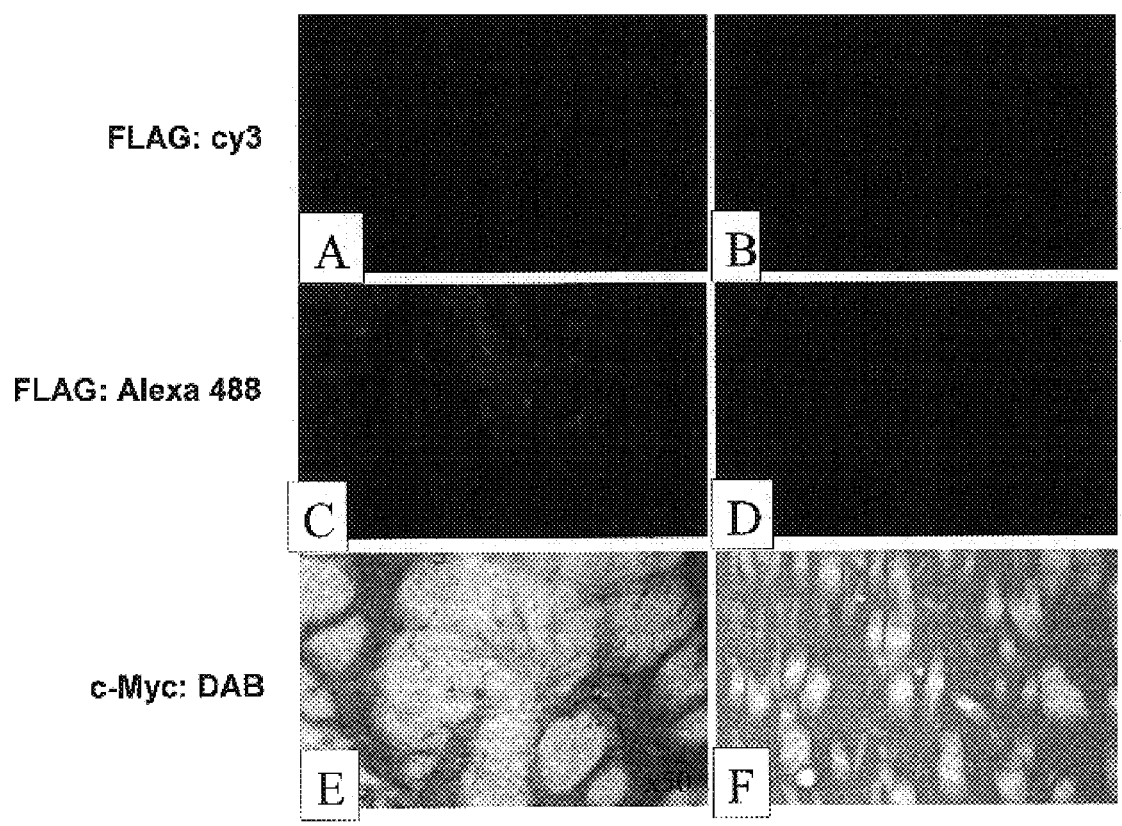

FIG. 20: Transduction of the adult rat striatum with EIAV TRIC vectors. Panel A represents 50 μm coronal sections stained with mouse monoclonal HA antibody. Immunofluorescent detection with a FITC secondary antibody indicates expression of AADC. Panel C represents 50 μm coronal sections stained with mouse monoclonal FLAG antibody. Immunofluorescent detection with Alexa 488 indicates expression of GTP-CH1. No expression is detected on the contralateral striatum (Panels B and D). Panel E represents staining with mouse monoclonal c-myc antibody detected with DAB immunohistochemistry. The results indicate that TH is expressed in the ipsilateral but not in the contralateral striatum (panel F). The cell specificty of the expression of these proteins in the transduced side is further confirmation of effective transduction.

Figure 21:
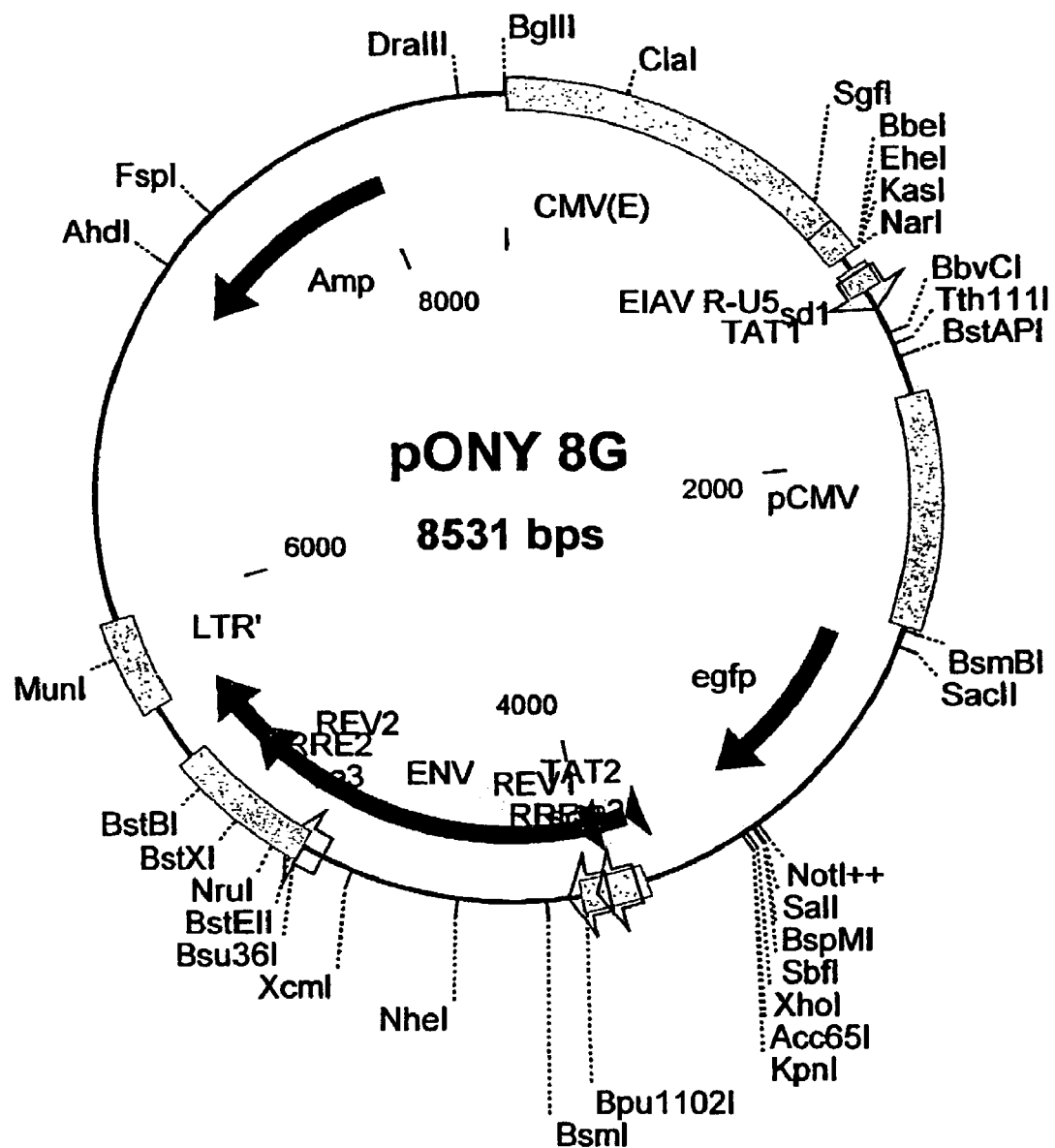

FIG. 21: Plasmid map of pONY8G

Figure 22:
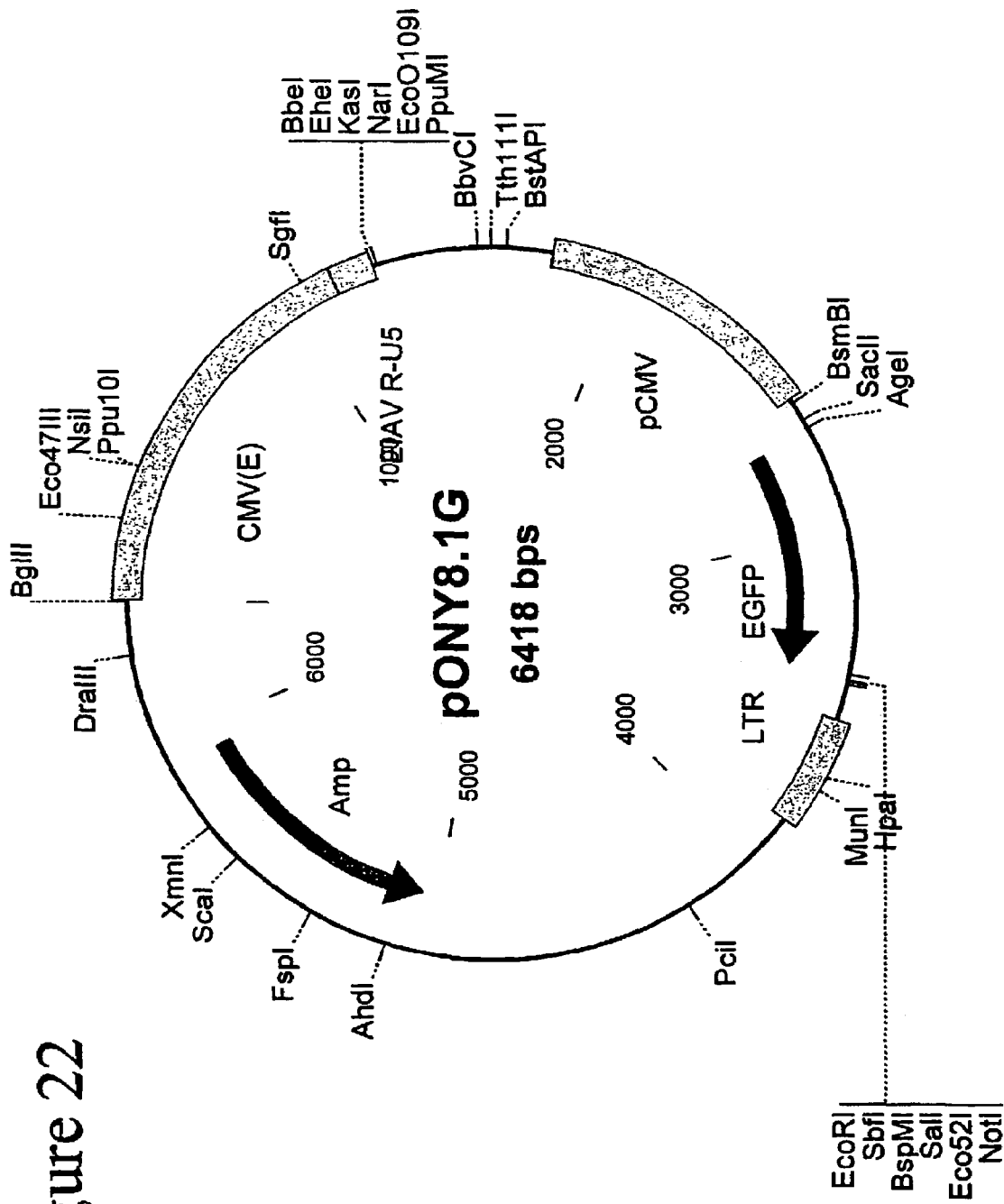

FIG. 22: Plasmid map of pONY8.1G

Figure 23:
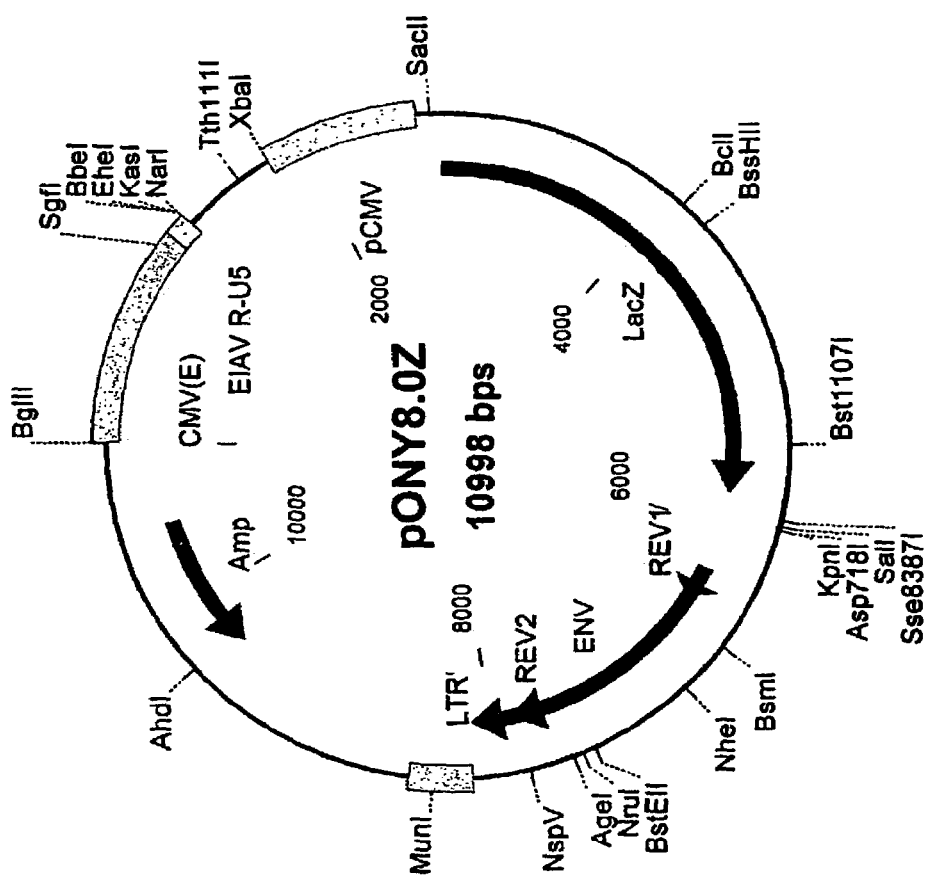

FIG. 23: Plasmid map of pONY8Z

FIG. 24. (A) Histogram showing the change in turns/minute induced by apomorphine stimulation (0.05 mg/kg) in 6-OHDA lesioned rats after injection of pONY8.1Z. or pONY8.1T. pONY8.1Z n=5, pONY8.1T n=2. (B) Apomorphine-induced rotational behavior in the 6-OHDA lesioned rats following injection of pONY8.1 Z (n=4) or pONY8.1T (n=7).

FIG. 25. Tyrosine hydroxylase (TH) immunoreactivity in the substantia nigra (A) and the striatum (B) of 6-OHDA lesioned rats injected with EIAV TRIC vectors. Note that there is no TH immunoreactivity on the ipsilateral side, compared with the contralateral side (control), indicating that the 6-OHDA has affected the dopaminergic neurons in substantia nigra pars reticulata (SNr).

FIG. 26: Catecholamines (ng/mg wet tissue) content in the normal and denervated striata of 6-OHDA lesioned rats injected with EIAV TRIC vectors. The amount of catecholamines detected in the denervated striatum confirm that the 6-OHDA lesion has affected most of the dopaminergic neurons of the nigra. The amount of dopamine produced by EIAV TRIC varies between 5–8% compared to the unlesioned striatum.

FIG. 27: DOPAC/Dopaine ratios in the normal and denervated striata of 6-OHDA lesioned rats injected with EIAV TRIC vectors. Note that the injected animals that had more pronounced reduction in drug-induced rotations are the animals where the DOPAC/Dopamine ratio (dopamine turnover) in the denervated striatum was lower.

FIG. 28A shows the amino acid sequence of codon-optimised GTP-cyclohydrolase I (SEQ ID NO:18). FIG. 28B shows the nucleotide sequence of codon-optimised GTP-cyclohydrolase I (SEQ ID NO:19). FIG. 28C shows the amino acid sequence of wild type GTP-cyclohydrolase I (SEQ ID NO:20). FIG. 28D shows the nucleotide sequence of wild type GTP-cyclohydrolase I (SEQ ID NO:21).

FIG. 29A shows the amino acid sequence of codon-optimised truncated tyrosine hydroxylase, type 2, from 8.9.4 MV opti Y (SEQ ID NO:22). The tyrosine hydroxylase sequence starts at position 3. MV is a "leader" required for efficient translation. FIG. 29B shows the nucleotide sequence of codon-optimised truncated tyrosine hydroxylase, type 2, from 8.9.4 MV opti Y (SEQ ID NO:23). FIG. 29C shows the amino acid sequence of codon-optimised truncated tyrosine hydroxylase, type 2 with serine at position 211 (SEQ ID NO:24). FIG. 29D shows the nucleotide sequence of codon-optimised tyrosine hydroxylase, type 2 with seine encoded by nucleotides 631–633 (SEQ ID NO:25). FIG. 29E shows the amino acid sequence of wild type truncated tyrosine hydroxylase, type 2 with tyrosine at position 211 (SEQ ID NO:26). FIG. 29F shows the nucleotide sequence of truncated wild type tyrosine hydroxylase, type 2, with tyrosine encoded by nucleotides 631–633 (SEQ ID NO:27). FIG. 29G shows the amino acid sequence of full-length tyrosine hydroxylase, type 2, with tyrosine at position 374 (SEQ TD NO:28). FIG. 29H shows the nucleotide sequence of full-length tyrosine hydroxylase, type 2, which encodes tyrosine with nucleotides 1120–1122 (SEQ ID NO:29).

FIG. 30A shows the amino acid sequence of codon-optimised aromatic amino acid decarboxylase in pONY8.9.4 MV opti Y (SEQ ID NO:30). FIG. 30B shows the nucleotide sequence of codon-optimised aromatic amino acid decarboxylase in pONY8.9.4 MV opti Y (SEQ ID NO:31). FIG. 30C shows the amino acid sequence of wild type aromatic amino acid decarboxylase (SEQ ID NO:32). FIG. 30D shows the nucleotide sequence of wild type aromatic amino acid decarboxylase (SEQ ID NO:33).

FIG. 31 shows a plasmid map of pONY8.9.4 MV opti Y.

Table 1: Catecholamines (ng/hour/$10^6$ cells) released by HEK 293T cells transfected with either the monocistronic, bicistronic or tricistronic plasmids (n.d., no detectable).

Table 2: Catecholamines (ng/$10^6$ cells) produced by HEK 293T cells transfected with either the monocistronic, bicistronic or tricistronic plasmids (n.d., no detectable).

Table 3: Integration efficiency of EIAV vectors.

EXPERIMENTAL

Example 1

Cloning of the Human Tyrosine Hydroxylase-1 Type 2 cDNA

The human Tyrosine Hydroxylase 1 Type 2 cDNA (Accession number X05290) is amplified by RT-PCR from human Substantia nigra poly $A^+$ mRNA (Clontech) and epitope tagged with the c-myc epitope using the primers described in FIG. 1. A 169 bp fragment corresponding to the 5' end of the gene is amplified using 5'hTH2 and 3'hTH2 primers (FIG. 1) whilst the 1418 bp 3' end fragment of the tyrosine hydroxylase cDNA is obtained using primers 5'hTH3 and 3'hTH1 (FIG. 1).

Titan One Tube RT-PCR kit (Boehringer) was used to perform the RT-PCR reaction. Typically the reaction is composed of two solutions.

Solution A
Contains 0.2 µg of human substantia nigra poly A+ RNA, 32 µM each dNTPs, 10 mM DTT, 1 µl RNAse Inhibitor (RNAsin, Promega), ~100 ng each primer and water, up to 25 µl.

Solution B
Contains 10 µl of 5×RT-PCR Buffer, 1 µl Enzyme mix, and water up to 25 µl.

Solutions A and B are mixed and the RT-PCR conditions set.

1.1. Amplification of the 169 bp product is carried out at 50° C., 30 min, to allow the RT reaction to take place, followed by 2 min at 94° C., and 35 cycles of 30 sec at 94° C., 30 sec at 60° C. and 45 sec at 68° C.

1.2. Amplification of the 1418 bp product is performed at 50° C., 30 min, to allow the RT reaction to take place, followed by 2 min at 94° C., and 35 cycles of 1 min at 94° C., 1 min at 60° C. and 2 min at 68° C.

Both fragments are purified and used as template in a third PCR reaction to obtain the full length Tyrosine Hydroxylase (TH) cDNA. The recombinant PCR reaction is carried out using primers 5'hTH2 and 3'hTH1 (FIG. 1) and a KlenTaq kit (Clontech) according to the instructions of the manufacturer. The PCR conditions are set up as follows: 35 cycles of 1 min at 94° C., 1 min at 60° C. and 2 min at 68° C. The recombinant PCR product is clone into pGEM-Teasy vector (Promega) to create pNE3.

The TH cDNA is then excised from pNE3 as a BamHI-EcoRI 1.57 kb fragment and ligated to pcDNA3.1/Zeo (Invitrogen) previously digested with the same enzymes. The newly generated mammalian expression plasmid is called pNE4 (FIG. 2).

Example 2

Cloning of the Human Aromatic Amino Acid Dopa Decarboxylase 1 cDNA

The human Aromatic Amino Acid Dopa Decarboxylase (AADC) cDNA (Accession number M76180 M30772) is amplified from a human liver cDNA expression library (Clontech) and epitope tagged with the HA epitope using the primers 5'hAADC and 3'hAADC, described in FIG. 3. The PCR reaction was performed using a KlenTaq kit (Clontech) following the instructions of the manufacturer. The reaction contains 4 µl human liver cDNA and 1 µM of each primer, in a final volume of 50 µl. The PCR conditions are as follows: A first step, 30 sec at 94° C.; a second step, 5 cycles of 30 sec at 94° C., 30 sec at 58° C. and 2 min at 68° C. and a third step, 30 cycles of 30 sec at 94° C., 30 sec at 55° C. and 2 min at 68° C.

The PCR amplifies the two expected bands, 1.485 kb and 1.36 kb, corresponding to the two transcripts of the Aromatic Amino Acid Dopa Decarboxylase (AADC). The 1.485 kb band is purified and cloned into pGEM-Teasy vector (Promega) to generate the plasmid called pNE1. The human AADC full-length cDNA is excised from pNEI as a ~1.5 kb BglII-SalI fragment and ligated to pcDNA3.1/Neo digested previously with BamHI and XhoI enzymes. The new plasmid generated is called pNE2 (FIG. 4).

Example 3

Cloning of the Human GTP-cyclohydrolase 1 cDNA

The human GTP-cyclohydrolase I (GTP-CH1) cDNA (Accession number U19523) is amplified from Poly A+ mRNA from human Substantia nigra and epitope tagged with the FLAG epitope using the primers 5'hGTP and 3'hGTP (FIG. 5). Titan One Tube RT-PCR kit (Boehringer) was used to perform the RT-PCR reaction. Typically the reaction is composed of two solutions, as described above in Example 1. Solutions A and B are mixed and the RT-PCR conditions set as follows: 50° C., 30 min, to allow the RT reaction to take place, followed by 30 sec at 94° C., and 35 cycles of 30 sec at 94° C., 30 sec at 60° C. and 1 min at 68° C.

The RT-PCR product (~0.75 kb) is purified and cloned into pGEM-Teasy vector (Promega) to generate plasmid-pNE5. The GTP-CH cDNA is excised from pNE5 as a ~0.75 kb BglII-NotI and ligated to pcDNA3.1/Hygro digested with BamHI and NotI enzymes to generate pNE6 (FIG. 6).

Example 4

Cloning of a Truncated Form of the Human Tyrosine Hydroxylase I Type 2

To avoid feed-back inhibition by dopamine on the TH enzyme it was decided to use the truncated form of TH type 2 lacking the regulatory domain. TH is activated by phosphorylation at sites located in this N-terminal domain and undergoes feedback end-product inhibition mediated by at least one of this phosphorylation sites (J. Biol. Chem. (1992) 267:25754–25758; Adv. Exp. Med. & Biol. (1993) 338: 87–92). This truncated TH (hTHt) is epitope tagged with the c-myc epitope and amplified by PCR using the primers 5'hTHt and 3'hTHt (FIG. 7) and plasmid pNE4 as template. The PCR reaction is carried out using Pfu I Polymerase (Stratagene) at 95° C., 1 min and 30 cycles of 1 min at 95° C., 1 min at 60° C. and 1 min at 72° C. A ~1.04 kb band is amplified, digested with BamHI and EcoRI enzymes and ligated to pcDNA3.1/Zeo previously digested with the same enzymes. The new plasmid generated is called phTHt (FIG. 8).

Example 5

Cloning of TH, AADC and GTP-CH into a Mammalian Expression Vector

The hTHt cDNA is cloned into BL-EP plasmid (Science, 269:847 (1995)) downstream the EMCV IRES. To achieve this, CMVp-hTHt fragments from phTHt is excised as a BglII-EcoRV and cloned into BLEP digested with BamHI-EcoRV to generate pneo1. The CMVp-DC fragment is excised from pNE2 as a BglII-EcoRV and ligated to BLEP cut with SmaI-BamHI to generate BLEP-CMV-DC.

To create a mammalian expression cassette comprising the hTHt and GTP-CH1 genes (bicistronic cassette), the GTP-CH1 cDNA is cloned downstream of the polio IRES as follows. The GTP-CH1 cDNA is excised from pNE6 as a ~0.75 kb NheI-XbaI fragment and cloned into BLEP-THt digested with the same enzymes. The new plasmid is called BLEP-THt-CH1. The CMVp-THt fragment is excised from pneo1 as a XbaI-EcoRV fragment and ligated to BLEP-hTHt-CH1 digested with the same enzymes to generate pneo2 (pbicis) (FIG. 9).

To create a tricistronic cassette comprising the hTHt, GTP-CH1 and AADC genes, BLEP-CMVp-DC and BLEP-hTHt-CH1 are digested with BlnI-ClaI to generate ptricis (FIG. 10). This creates a cassette which has the CMV promoter, DC, hTHt and GTP-CH1 in that order.

Example 6

Transient Expression from the Bicistronic and Tricistronic Cassettes in Heterologous Human Cells Human embryonic kidney 293T (HEK293T) cells do not synthesise any catecholamines and they do not express any catecholaminergic enzymes. They are chosen to determine if the bicistronic and tricistronic expression cassettes are functional HEK 293T cells are seeded in a 6× well plates at a density of ~2–3×10$^5$ cells/well. Twenty-four hours post-plating the cells are transfected with 2 µg of plasmid DNA using Fugene™ (Roche) in serum-free medium, following the instructions of the manufacturer. As control of transfection 0.2 µg ($^1/_{10}{}^{th}$) of the GFP expressing plasmid pEGFP-C1 (Clontech) is added to the DNA-Fugene™ mix.

Approximately 48 h post-transfection the cells are washed in Phosphate Buffer Saline (PBS) and harvested. Total cell extracts are prepared using Lysis buffer (Promega). Approximately 10 µg of total protein are loaded onto three 10% SDS-PAGE gel and the proteins are separated and transferred to a nitrocellulose ECL-western membrane (Amersham-Pharmacia). The membranes are probed with $^1/_{1000}{}^{th}$ dilution of either mouse anti-HA (Roche), mouse anti-cmyc (Roche) or mouse anti-FLAG (Sigma) antibodies. The secondary antibody was a $^1/_{2000}{}^{th}$ dilution of HRP-labelled rabbit anti-mouse (Dako). The antibodies bound to the membranes are detected using an ECL-Western detection kit.

Proteins of the appropriate apparent molecular weight are detected in the transfected cells and not in the mock control: HA-hAADC, ~53 kDa; cmyc-hTHt, ~42 kDa and FLAG-GTP/CH1, ~30 kDa. The bicistronic and tricistronic cassettes express two or three of the enzymes, respectively (FIG. 11).

Example 7

Production of Catecholamines in Transiently Transfected Human Cells

As described in example 6, HEK 293T cells are seeded in a 6× well plates at a density of ~2–3×10$^5$ cells/well. Twenty-four hours post-plating the cells are transfected with 2 µg of plasmid DNA using Fugene™ (Roche) in serum-free medium, following the instructions of the manufacturer. As control of transfection 0.2 µg ($^1/_{10}{}^{th}$) of the GFP expressing plasmid pEGFP-C1 (Clontech) is added to the DNA-Fugene™ mix.

Approximately 48 h post-transfection the cells are washed in Phosphate Buffer Saline (PBS). To measure the catecholamines release into the medium, 0.5 ml of 'Release Buffer' (Hank's Balanced Salt Solution, 25 mM Hepes pH 7.4, 0.25% BSA and 1 nM tyrosine) is added to the transfected cells. These cells are incubated at 37° C. for 30 min. No tetra-hydrobiopterin (BH$_4$), the TH cofactor, is added to the cells in this experiment. The catecholamines present in the buffer are extracted with the same volume of 0.8M perchloric acid (PCA) and 0.2 mM EDTA. Cell debris is removed by spinning down in a microfuge at 4° C., 10,000 rpm, for 15 min. The release step can be repeated for another 30 min. The catecholamines produced in the cells are extracted in 0.5 ml 0.4M PCA and 0.1 mM EDTA.

The catecholamines are separated in a reverse phase C18 column (ESA Analytical) by HPLC (Dionex) using Cat-A-Phase mobile phase (ESA Analytical) at a flow rate of 1.5 ml/min for 15 min. Approximately 20 µl are injected in the system. The catecholamines are detected in an electrochemical detector (ESA Analytical) connected to an Analytical cell (model 5144, ESA Analytical) with input potentials as follows: Guard cell, +250 mV; Channel 1, 10 mV and Channel 2, −250 mV. The amount of catecholamines in the samples is calculated by integrating the area of the peaks to known standards separated following the same protocol. This method allows the detection of L-dopa, Dopamine and DOPAC, a specific degradation product of dopamine.

The detection of catecholamines released (Table 1) and/or produced (Table 2) by heterologous cells independent of $BH_4$ confirms that the enzymes are functional. As expected, L-dopa is produced by mono-, bi- and tricistronic expression cassettes whilst dopamine is only produced by the tricistronic cassette. The bicistronic makes far greater amount of L-dopa than TH alone confirming the utility of GTP-CH1 for providing $BH_4$ in these cells. Dopamine is also produced by the bicistronic in combination with AADC, DOPAC, the specific degradation product of dopamine is only detected when high amounts of dopamine are produced.

Example 8

Construction of Lentiviral Vector Expressing the Bicistronic and Tricistronic Cassettes Lentiviral vectors are particularly useful for gene transfer to non-dividing cells. Amongst many important non-dividing target cells are the neurons of the human brain. These cells might be target cells for the delivery of TH, AADC and GTP-CH1 for the treatment of Parkinson's disease. Here we describe the construction of minimal EIAV based vectors that will deliver and express TH, MDC and GTP-CH1 and will be capable of producing the neurotransmitter (dopamine) missing in the severely affected Parkinsonian brain. This therapy will be appropriate for late stages of PD patients that do not respond to L-DOPA treatment. The structure of the general minimal EIAV vectors is shown in FIG. 12 pONY8G Construction pONY8G was derived from pONY8.0Z by exchange of the LacZ reporter gene for the enhanced green fluorescent protein (GFP) gene. This was done by transferring the SalI-KpnI fragment corresponding to the GFP gene and flanking sequences from pONY2.13GFP (WO99/32646) into pONY8.0Z cut with the same enzymes pONY8.0Z was derived from pONY4.0Z (WO99/32646) by introducing mutations which 1) prevented expression of TAT by an 83 nt deletion in the exon 2 of tat) prevented S2 ORF expression by a 51 nt deletion 3) prevented REV expression by deletion of a single base within exon 1 of rev and 4) prevented expression of the N-terminal portion of gag by insertion of T in ATG start codons, thereby changing the sequence to ATTG from ATG. With respect to the wild type EIAV sequence Acc. No. U01866 these correspond to deletion of nt 5234–5316 inclusive, nt 5346–5396 inclusive and nt 5538. The insertion of T residues was after nt 526 and 543.

The Bicistronic cassette expressing the human THt and GTP-CH1 genes is excised from pneo2 as a XhoI-XbaI fragment and ligated to pONY8G (SEQ ID NO 1, FIG. 21), the construction of which is described above, digested with the same enzymes. In this case the CMVp-GFP cassette is replaced by the CMVp-hTHt-CH1 cassette. The new plasmid is called pONY8-BIC (SEQ ID No 4).

The Tricistronic cassette expressing the human AADC, THt and GTP-CH1 genes is excised from pTricis as a XhoI-XbaI fragment and ligated to the backbone of pONY8G (SEQ ID NO 1, FIG. 21), the construction of which is described above. The new plasmid is called pONY8TRIC (SEQ ID NO 5). The resulting vector RNA genome size of this vector is 8.8 kb and therefore 10% longer than that of the 8 kb EIAV RNA genome.

pONY8.1Z and pONY8.1G Construction pONY8.1Z was obtained directly from pONY8.0Z by digestion with SalI and partial digestion with SapI. Following restriction the overhanging termini of the DNA were made blunt ended by treatment with T4 DNA polymerase. The resulting DNA was then religated. This manipulation results in a deletion of sequence between the LacZ reporter gene and just upstream of the 3'PPT. The 3' border of the deletion is nt 7895 with respect to wild type EIAV, Acc. No. U01866. Thus pONY8.1Z does not contain sequences corresponding to the EIAV RREs. pONY8.1G was derived from pONY8G using the same strategy.

Both the Bicistronic and Tricistronic cassettes are excised as NsiI-XhoI fragments from pONY8BIC (SEQ ID NO: 4) or pONY8TRIC (SEQ ID NO: 5) respectively and ligated to the backbone of pONY8.1G (construction described above, SEQ ID NO 2, FIG. 22) digested with the same enzymes. The two new plasmids are called pONY8.1BIC and pONY8.1TRIC (FIG. 13).

The presence of a sequence termed the central polypurine tract (cPPT) may improve the efficiency of gene delivery to non-dividing cells. The cis-acting element is located in the EIAV polymerase coding region element and can be obtained as a functional element by using PCR amplification using any plasmid that contains the EIAV polymerase coding region (for example pONY3.1, which is described in WO 99/32646 (e.g. See example 9, FIG. 6)) as follows. The PCR product includes the cPPT and the central termination sequences (CTS). The oligonucleotide primers used in the PCR reaction were:

```
EIAV cPPT PD POS:
5'-CGG ATC AGA TCTTGA TCA CTG CAG GCT CTC AlT ACT TGT AAC AAA GGG AG-3'
(SEQ ID NO: 6)

EIAV cPPT PD NEG:
5'-AG CTC GGA TCC CTG CAG CAT GTT CAC CAG GGA TTT TG-3'
(SEQ ID NO: 7)
```

The recognition site for BglII is underlined, for BclI in italic, for BamHI in bold italic and PstI in bold. The introduction of the cPPT/CTS into a position upstream of the EMCV IRES or PV IRES was achieved by subcloning the unique BclI-BssHII fragment of pONY8TRIC into pSL-1180 (Pharmacia) using the same sites in the vector. This was termed pSL-1180-PD. Digestion of the cPPT/CTS PCR product with BglII and BamHI allowed the insertion into the BclI site upstream of the EMCV IRES or with PstI, into the unique PstI site upstream of the polio IRES, to generate pSL-1180-PD-5'cPPT or pSL-1180-PD-3'cPPT, respectively. The orientation of the fragment cloned into pSL-1180-PD was confirmed by DNA sequencing. The BclI-BssHII fragment from these two clones was ligated into pONY8TRICdelCTS, a modified form of pONY8TRIC. PONY8TRICdelCTS was constructed by ligating the SalI-PinAI fragment from pONY8ZdelCTS (described below) into pONY8TRIC digested with XhoI and PinAI. The two new vector genomes are called pONY8TRIC5'cPPT and pONY8TRIC3'cPPT. A schematic representation of these vector genomes is shown in FIG. 14.

Construction of pONY8ZdelCTS pONY8Z (SEQ ID NO 3, FIG. 23) is modified to remove the CTS which already is present the pONY8Z vector. This is achieved by subcloning the SalI to ScaI fragment encompassing the CTS and RRE region from pONY8Z into pSP72, prepared for ligation by digestion with SalI and EcoRV. The CTS region is then removed by digestion with KpnI and PpuMI, the overhanging ends 'blunted' by T4 DNA polymerase treatment and then the ends religated. The modified EIAV vector fragment is then excised using SalI and NheI and ligated into pONY8Z prepared for ligation by digestion with the same enzymes. This new EIAV vector is termed pONY8Z del CTS.

Construction of pONY 8.9.4 MV opti Y pONY8.9.4 MV opti Y (SEQ ID NO:34, FIG. 31) is a derivative of pONY8Z (SEQ ID NO:3, FIG. 23) obtained as a result of multiple routine molecular biological manipulations.

The features of the plasmid are as follows:
1) Immediate early promoter of human cytomegalovirus: nucleotides (nt) 1–1108;
2) EIAV R-U5-packaging signal region: nt 1109–1748. This sequence corresponds to 268 to 897 from EIAV Gen bank Accession No. U01866 except that there is an additional C residue present after nucleotides 270 and 8178. These correspond to the $4^{th}$ position of the R region, and these additional residues are incorporated into the genome of pONY8.9.4 MV opti Y. The vector sequence also contains alterations in the EIAV Gag encoding region, which alter all ATG codons to ATTG;
3) A linker region including a Kozak consensus sequence for efficient initiation of translation: nt 1749–1791;
4) Neomycin phosphotransferase gene: nt 1792–2586;
5) A linker region: nt 2587–2663;
6) Immediate early promoter of human cytomegalovirus (CMV): nt 2664–3389, corresponding to human herpesvirus 5 strain AD169, complete genome. BK000394 nt 175388–174652;
7) 5' untranslated region, which includes a Kozak consensus sequence for efficient initiation of translation: nt 3390–3508;
8) Codon-optimised truncated tyrosine hydroxylase (TH) gene (SEQ ID NO:23): nt 3509–4525, including stop codon. The sequence of the gene differs from that of the wild type TH type 2 (SEQ ID NO:27);
9) Linker region: nt 4526–4549;
10) Encephalomyocarditis virus (EMCV) sequence which acts as an internal ribosome entry site (IRES): nt 4550–5126;
11) Linker: nt 5127–5128. The last two bases of the EMCV IRES before AUG 11 (AT) are changed to (CC) to introduce an NcoI site;
12) Codon-optimised aromatic amino acid decarboxylase gene (SEQ ID NO:31): nt 5129–6571, which includes the stop codon;
13) Linker: nt 6572–6675;
14) Poliovirus sequence which acts as an internal ribosome entry site: nt 6676–7407. This sequence is derived from poliovirus type II (Lansing strain), however IRESs from other polioviruses could be substituted;
15) Linker: nt7408–7428;
16) Codon-optimised GTP-cyclohydrolase I sequence (SEQ ID NO:19): nt 7429–8181, which includes the stop codon;
17) Linker: nt 8182–8205;
18) Modified form of the woodchuck hepatitis virus post-transcriptional regulatory element (WPRE): 8206–8795. The modifications ablate expression of the X-protein of the hepatitis virus and any peptides derived from it. This element boosts expression 2–3fold in 293T cells and is optional;
19) Linker: nt 8796–8809;
20) EIAV sequence including the 3'PPT and approximately 25 nucleotides from the 5' end of the U3 region: nt 8809–8902;
21) EIAV sequence including approximately 5 nucleotides from the extreme 3' end of the U3 sequence and the R-U5 sequence: nt 8910–9030; and
22) Sequences derived from the backbone of pBS II KS+: nt 9031–11622.

Example 9

Production of Lentiviral Vector Stocks Expressing Therapeutic Genes

The three plasmids transfection method as described previously (Soneoka et al., 1995) was used to generate pseudotyped lentiviral vectors. Transfections are carried out in HEK 293T cell line (Soneoka et al., 1995) to produce the vector virions. Culture supernatants were harvested 48 h post-transfection and filtered through 0.45 μm pore-size filters (Millipore). The viral supernatant is concentrated 100–1000 fold by ultracentrifugation (Burns et al., 1993 PNAS 90:8033–8037) and resuspended in PBS.

The number of particles in the viral stocks were titered by Performance Enhanced Reverse Transcriptase (PERT) assays and compared to a standard pONY8G viral prep with known biological titer. The biological titter is evaluated by transducing D17 cells, a dog osteosarcoma cell line. The titer is expressed in transducing units per ml (t.u./ml). For this purpose, cells were seeded into 12×well tissue culture plates the day before infection at $1 \times 10^5$ cells per well. Viral supernatants prepared by transfecting 293T cells with appropiate plasmids, as described above, are added to the target cells. Polybrene (8 μg/ml) is added to each well at the time of transduction into 0.5 ml of the culture supernatant used for infection. Approximately 2–5 hours post-transduction, the culture supernatant is replaced by fresh medium. Cells expressing GFP (green) are viewed under UV light and counted.

The PERT assay uses real time quantitative RT-PCR technology to detect a specific PCR product from MS2 RNA and the retroviral reverse transcriptase present in the viral particles (in this case EIAV RT). Briefly, the viral particles are disrupted by mixing 1:1 volumes of viral vector stocks and disruption buffer (40 mM Tris-HCl pH 7.5, 50 mM KCl, 20 mM DTT and 0.2% NP-40). Serial dilutions of the disrupted particles are carried out prior to adding them to the RT-PCR TaqMan reaction mix (Perkin-Elmer). In addition, the reaction mix contains $1/10^{th}$ volume of disrupted viral particles, 300 nM PERT forward primer, 300 nM PERT reverse primer, 150 nM PERT probe, $1/10^{th}$ of 0.8 mg/ml MS2 RNA. The RT-PCR conditions are as follows: Hold, 48° C. for 30 min; hold, 95° C. for 10 min; forty cycles, 95° C. for 15 sec and 60° C. for 1 min. The data is analysed using ABI PRISM$^R$ Sequence Detection System (Perkin-Elmer).

Similarly, the RNA content of the viral preps is also estimated by RT-PCR comparing to a standard pONY8G viral prep. Viral RNA is isolated from the viral stocks using a Qiagen viral RNA kit (Qiagen) and DNAse I treated (Ambion). Serial dilutions of the viral RNA are used as template in the RT-PCR reaction. Two reaction mixtures are prepared, +RT and −RT, containing $1/10^{th}$ volume of viral RNA template and the specific forward and reverse primers and probe. The RT-PCR conditions are as follows: Hold, 48° C. for 30 min; hold, 95° C. for 10 min; forty cycles, 95° C. for 15 sec and 60° C. for 1 min. The data is analyse using ABI PRISM$^R$ Sequence Detection System (Perkin-Elmer). FIG. 15 shows the PERT assay results and the viral RNA content of EIAV TRIC and EIAV GFP vectors. EIAV TRIC vectors seem to have similar number of particles per prep, but ~4 times less RNA than EIAV GFP.

The efficiency of integration of the EIAV-TRIC vector genomes is measured by quantitative real-time PCR of total genomic DNA from transduced cells. For this purpose, target cells such as D17 or HT1080 cells are transduced with EIAV-TRIC or EIAV-GFP at different MOI(s) as described previously. The transduced cells are split at least three times prior to isolating total DNA from them. Approximately 100 ng of total DNA is used as template in the PCR reaction. Amplification of the EIAV packaging signal fragment is quantified by comparing to the amplification of a housekeeping gene, such as beta-actin or GAPDH. Real time quantitative PCR conditions are as follows: hold, 95° C. for 10 min; forty cycles, 95° C. for 15 sec and 60° C. for 1 min. The data is analysed using ABI PRISM$^R$ Sequence Detection System (Perkin-Elmer). Table 3 shows the integration efficiency of EIAV vectors.

Example 10

EIAV-BIC and -TRIC Vectors Yield Expression of TH, AADC and GTP-CH1 in Heterologous Cells in Culture Heterologous cells, such as D17 or HEK 293T cells are transduced with EIAV-TRIC vectors at different multiplicity of infection (MOI). Viral supernatants are prepared by transfecting 293T cells with the appropriate plasmids and added to the target cells as described in previous examples. The cells are split at least three times before analysing them to ensure that there is no pseudotransduction. Expression of the TH, AADC and GTP-CH1 genes is analysed by Western blot (FIG. 16) and immunocytochemistry (FIG. 17). Bands of the appropriate apparent molecular weight are detected in cell extracts of transduced D17 cells: HA-hAADC, ~53 kDa; cmyc-hTHt, ~42 kDa and FLAG-GTP/CH1, ~30 kDa. Mouse monoclonal antibodies that recognise the tagged proteins have been used as described before. The antibodies bound to the proteins are detected with an HRP conjugated rabbit anti-mouse IgG. The bicistronic and tricistronic cassettes express two or three of the enzymes, respectively (FIG. 16).

The transduction of D17 cells is determined by immunocytochemistry using mouse monoclonal HA antibody (Roche) and Alexa 488 conjugated goat anti-mouse IgG (Molecular Probes) (FIG. 17). As control, D17 cells were transduced with EIAV lacZ.

The catecholamines produced in the transduced cells are extracted in 0.5 ml 0.4M PCA and 0.1 mM EDTA, separated by HPLC and detected electrochemically as previously described in the above examples. L-dopa, Dopamine and DOPAC are produced by HEK 293T cells transduced with EIAV TRIC vectors (FIG. 18).

Example 11

EIAV Vectors Yield Expression of TH, AADC and GTP-CH1 in the Caudate Nucleus of Adult Rats.

Parkinson's disease (PD) is a neurodegenerative disorder characterized by the loss of the nigrostriatal pathway and is responsive to treatments that facilitate dopaminergic transmission in caudate-putamen. In experimental animals, genetically modified cells that express tyrosine hydroxylase, and thereby synthesize dihydroxyphenylalanine (L-dopa), induce behavioural recovery in rodent models of PD (Wolff et al (1989) PNAS (USA) 86:9011–14; Freed et al (1990) Arch. Neurol. 47:505–12; Jiao et al. (1993) Nature. 262: 4505). An alternative approach is that of direct in vivo somatic cell gene transfer whereby the cells of the striatum are converted into dopamine producer cells by transduction with a vector expressing TH, AADC and GTP-CH1.

In order to examine virally encoded gene expression EIAV-TRIC and EIAVlacZ are stereotaxically microinjected into the adult rat striatum as follows. Rats are anesthesized with hypnorm and hypnovel (Wood et al., (1994) Gene Therapy 1:283–291) and injected with 2×1 μl of viral stocks (for EIAV lacZ is typically 1–5×10$^9$ t.u./ml) into the striatum, at coordinates: Bregma 3.5 mm lateral, 4.75 mm vertical from dura, and 1 mm rostral, 3.5 mm lateral 4.75 mm vertical using a fine drawn glass micropippette over a period of 2 min. The pippette was pulled up 1 mm and left for another 2 min before retracting slowly to the surface. Animals are analysed 1 and 2 weeks following injection. Rats are perfused with 4% paraformaldehyde (PFA) containing 2 mM MgCl$_2$ and 5 mM-ethylene glycol bis (beta-aminoethylether)-N,N,N',N'-tetraacetic acid. Brains are removed and placed in fixative overnight, submersed in 30% sucrose at 4° C. overnight and frozen on Tissue-Tech OCT embedding compound (Miles Ind. USA). Fifty-micrometer sections are cut on a freezing microtome and floated briefly in PBS-2 mM MgCl$_2$ at 4° C. as a wash. Expression of lacZ is determined by placing the sections in X-gal staining solution for 3–5 hours. EIAV TRIC is injected into the rat striatum using the same coordinates as described above. In addition two more injection sites at Bregma 2.5 mm lateral, 4.75 mm vertical and 1.8 mm rostral, 2.5 mm lateral and 5 mm vertical were performed. Expression of AADC, TH and GTP-CH1 is detected by immunohistochemistry using mouse monoclonal antibodies raised against the epitope tags, HA, c-myc and FLAG respectively. These antibodies will distinguish between the rat and the human proteins. Brains sections are incubated with mouse anti-HA (Santa Cruz), anti-c-myc (Santa Cruz) or anti-FLAG (Sigma) antibodies (1:100$^{th}$ dilutions) at 4° C. overnight in PBS-10% goat serum and 0.5% TritonX-100. Sections are washed with PBS and then incubated with Alexa 488 (Molecular Probes) or FITC (Jackson Laboratories) conjugated goat anti-mouse or anti-rabbit IgG ($1/1000^{th}$ dilutions) at room temperature for 2–3 hours. After washing the sections are examined under a fluorescence microscope. For DAB staining sections were developed using the avidin-biotin system (Vectastain kit (Vactor Laboratories)).

TH is not expressed within either neurons or glia of the rat striatum (Chatterjee et al. (1992) Science 258:1485–88). Endogenous TH immunoreactive (TH-IR) within the striatum is limited to the dopaminergic terminals of afferent fibers from substantia nigra. To determine whether the cells transduced are neurons or glial-cells a TH antibody is used in conjuction with antibodies that recognise either neuronal (NeuN) or glial (GFAP) markers. Double immunostaining is carried out on brain sections. Sections are incubated with rabbit polyclonal TH antibody ($1/100^{th}$; Affinitti) and mouse monoclonal neurofilament (NeuN) antibody ($1/50^{th}$; Chemicon), or mouse monoclonal GFAP ($1/50^{th}$; Chemicon) at 4° C. overnight in PBS-10% goat serum and 0.5% TritonX-100. Sections are washed with PBS and then incubated with Alexa 488 conjugated goat anti rabbit IgG ($1/200^{th}$; Molecular Probes) or CY3 conjugated goat anti-mouse IgG ($1/200^{th}$; Jackson Laboratories) at room temperature for 2–3 hours. After washing the sections are examined under a fluorescence microscope.

FIG. 19 shows transduction of the adult rat striatum with pONY8Z seven days following injection. FIG. 20 shows transduction of the rat striatum with pONY8TRIC two weeks following injection.

Example 12

Efficacy of EIAV-TRIC Vectors in a Rodent Model of Parkinson's Disease: Apomorphine-Induced Rotational Behavior The aim of the present study is to replace dopamine in the striatum of animal model of Parkinson's disease. Rats receive 6-OHDA lesions of the right medial forebrain bundle (MFB). Stereotaxic injections are performed under anesthesia using 10 μd Hamilton syringe with 33-gauge blunt tip needle. Each rat receives 4 μl of 4 μg/μl 6-OHDA HCl (Sigma) dissolved in 2 mg/ml ascorbate-saline (0.2% ascorbic acid, 0.9% NaCl). The solution is slowly infused at the speed of 0.5 μl/min. Three weeks following 6-OHDA lesion, rats are tested for amphetamine-induced rotation. Animals are injected i.p. with 2.5 mg/kg D-amphetamine (Sigma). Amphetamine is diluted in PBS. Rotational asymmetry is monitored over 90 minutes. Only rats with >7 turns per minute are used for the following experiment. For apomorphine-induced rotation, animals are tested twice on 0.05 mg/kg sc 4 days apart Fifteen rats show good homogeneity as to the extent of the 6-OHDA lesions. Two experiments are performed with EIAV-TRIC vectors. Three weeks after 6-OHDA lesions, EIAV-based lentiviral vectors carrying the genes involved in the dopamine synthesis are unilaterally injected into the striatum (ipsilateral to the lesion). Two groups of animals are included in each study: in the first experiment pONY8.1Z n=5; pONY8.1T n=4; in the second study pONY8.1Z n=4; pONY8.1T n=7. In order to assess a possible functional benefit of the treatment, apomorphine-induced rotation is tested weekly after the viral injection (FIG. 24.A). Two pONY8.1T-injected animals (C3R5 & C5R4) showed reduction in contralateral rotation than the pre-apo2 rotation during the whole experiment period, reaching a 65 and 70% decrease 3 weeks after viral injection (The present inventors suggest that the 70% is probably an artefact since one rat slipped out of the harness during this rotation). A 60 and 35% decrease is observed 10 weeks following injection of the viral solution for these two rats. In the second study, dopamine replacement did reduce the number of apomorphine-induced rotations experienced in 6 animals (from 7 rats) injected with pONY8.1T (FIG. 24.B). The average of reduction in rotations 6 weeks after viral injection is about 45% compared to pre-apomorphine 2.

At the end of each experiment, rats are perfused with ice-cold PBS containing 0.02% ascorbic acid and 5000 units of heparin followed by 4% paraformaldehyde solution. The brains are dissected and placed overnight in 4% paraformaldehyde solution followed by the cryoprotection in 30% sucrose solution. TH-immunohistochemical labeling is performed on nigral and striatal sections to test the extension of the lesion. TH-immunostaining is performed using polyclonal Rabbit anti-TH antibodies on nigral (FIG. 25.A) and striatal (FIG. 25.B) sections. Catecholamines produced by EIAV TRIC vectors in the denervated striata of 6-OHDA rats are determined by HPLC and electrochemical detection, as described in the previous examples. The results are shown in FIGS. 26 and 27.

Example 13

EIAV-TRIC Vectors Used for Correcting the 6-OHDA Primate Model of Parkinson's Disease This model comprises unilateral injection of 6-hydroxydopamine (6-OHDA) into the nigrostriatal bundle of the small New World monkey the common marmoset (*Callithrix jacchus*). As in the rodent model, the asymmetry caused by the toxin in receptor sensitivity between the denervated and intact striatum results in rotational behaviour upon i.m. administration of domapinergic factors, such as apomorphine (Annett et al., (1997). The rate of amphetamine-induced rotations is directly related to the striatal dopaminergic dysfunction and is used to evaluate the therapeutic efficacy of different treatments for PD (Annett et al. (1994) Exp Neurol. 125:228–246; Annett et al. (1992) Brain, 115:825–856). Marmosets aged 18–24 months are lesioned under anesthesia by delivery of 4 mg/ml free base weight 6-OHDA (Sigma) dissolved in 0.01% ascorbate-saline. 6-OHDA was injected stereotaxically into five sites in the nigrostriatal bundle on one side of the brain (coordinates: AP+6.5; L+/−1.2, V+6 and +7: L+/−2.2, V+6.5 and V+7.5, L+/−3.2, V+7.5, as described in Stephan et al. (1980) Berlin: Springer-Verlag). Three microlitres are injected in the most lateral site and two microlitres in the other four sites. The 6-OHDA lesioned animals are examined for rotational behaviour prior to the lesion, after the lesion before the viral vectors injection and one month after the vectors are injected. Rotations are recorded during 30 min sessions starting 30 min after the injection of the drug. The marmosets are filmed while in a transparent Perspex box and the number of complete turns are counted.

Four 6-OHDA lesioned animals are injected with 30 μl of EIAV-TRIC or EIAVlacZ viral stocks into the Caudate Putamen at 6 sites (5 μl/site). Behavioural assessment of the monkeys on reaching tasks and apomorphine-induced rotations tests will be made one month post-injection and at regular interval for several months for long-term follow-up. Animals are sacrificed and brain tissue sections are analysed for TH immunoreactivity as described previously. The level of catecholamines in the denervated striatum is determined by HPLC and electrochemical detection (as described above).

Example 14

EIAV-TRIC Vectors Used for Correcting the MPTP Primate Model of Parkinson's Disease.

The primate model of Parkinson's disease is considered the gold-standard model for evaluation of potential therapies prior to entering human clinical trials. This model is originally developed from the observation in the early 1980s that groups of younger people are developing a neurodegenerative disorder strikingly similar to idiopathic Parkinson's disease. The source of this disorder is traced to the use of a street drug, and specifically to the chemical known as 1-methyl-4-phenyl-1,2,3,6-tetrahydropyridine (MPTP) (Langston (1985) Trends in Pharmacol. Sci. 6:375–378). When MPTP is given to primates, the animals developed a parkinsonian disorder that has become the principle model for testing anti-parkinsonian agents. Peripherally administered MPTP will cross the blood brain barrier, whereupon is converted into MPP+ by monoamine oxidase B (MAO-B). MPP+ is a potent neurotoxin that eventually causes the degeneration of nigro-striatal dopamine pathway, as seen in Parkinson's disease.

Cynomolgus monkeys (*Macaca fascicularis*) are rendered parkinsonian by weekly intravenous injections of 0.5–1 mg/kg MPTP for ten consecutive months. Animals are trained to perform fine motor tasks prior to the administration of MPTP. The parkinsonian monkeys are tested for marked reduction of spontaneous activity, bilateral action tremor, freezing and posture and balance impairment to assess the efficacy of the lesion. Motor deficits are assessed according to a nonhuman primate disability rating scale (Herrero et al., (1993) Neuroscience 56:965–72). In addition, apomorphine (0.1 mg/kg, i.m.) is also given every two weeks to test the appearance of circling behaviour. The monkeys are allowed to recover from the last MPTP administration for 3 months prior to the intrastriatal transduction. Animals are anesthesized with a mixture of ketamine (10 mg/kg) and midazolan (1 mg/kg) and placed in the stereotactic frame. A hole is drilled in the skull at the level of the right frontal ventricle according to the atlas of Szabo and Cowan (Szabo and Cowan (1984) J. Comp. Neurol. 222: 265–300), and a ventriculography is performed by injecting 0.4 ml of Omnigrass into the right ventricle. The intercomisural line (AC-PC line) is measured and the coordinates for the putamen nucleus are adjusted according to the atlas.

EIAV-TRIC and EIAVlacZ viral vectors (5 µl of ~1–5× $10^9$ t.u./ml) are stereotaxically injected unilaterally into the left putamen in two sites along the rostrocaudal axis using a Hamilton syringe. Briefly, 2×5 µl of ~1–5×$10^9$ t.u./ml are injected into the putamen nucleus as follows: rostral putamen, AP+3.4 mm from the midpoint of the AC-PC line; ML 12 mm from the longitudinal sinus, and VD 15 mm below dura mater. Animal receive antibiotics (ampicillin 250 mg/day, i.m.) prophylactically for two weeks and analgesia with nonsteroidal anti-inflammatory drugs (flunixin, 2.5 mg/kg). Animals are followed periodically (every two weeks) for 3–5 months in order to determine whether the therapeutic vectors improve the parkinsonian behaviour (During et al. (1994)). They are tested for motor deficits as described above. At the end of the experimental period, animals are transcardially perfused with 4% PFA in PBS. The brains are fixed overnight in the same fixative at 4° C. and then immersed in 30% sucrose in PBS. Coronal brain sections (30 µm thick) were cut on a freezing microtome and collected in PBS. TH immunoreactivity and levels of catecholamines in the denervated putamen are analysed as described previously.

All publications mentioned in the above specification are herein incorporated by reference. Various modifications and variations of the described methods and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, biology or related fields are intended to be within the scope of the following claims.

TABLE 1

| DNA | L-DOPA | DOPAC | DA |
|---|---|---|---|
| Mock | n.d. | n.d. | n.d. |
| TRIC | 0.745 +/− 0.047 | n.d. | 0.545 +/− 0.055 |
| BIC + AADC | 0.729 +/− 0.045 | 0.531 +/− 0.10 | 11.31 +/− 1.01 |
| BIC | 58.55 +/− 6.20 | n.d. | n.d. |
| hTHt | 0.845 | n.d. | n.d. |

TABLE 2

| DNA | L-DOPA | DOPAC | DA |
|---|---|---|---|
| Mock | n.d. | n.d. | n.d. |
| TRIC | 0.3013 +/− 0.0426 | n.d. | 0.5073 +/− 0.046 |
| BIC + AADC | 0.398 +/− 0.2929 | 0.4567 +/− 0.1836 | 10.244 +/− 1.95 |
| BIC | 133 +/− 19.233 | n.d. | n.d. |
| hTHt | 38 | n.d. | n.d. |

TABLE 3

| | Relative Integration Efficiency | | | | | |
|---|---|---|---|---|---|---|
| MOI | pONY8G | pONY8T-1 | pONY8T-2 | pONY8.1Z | pONY8.1T | Integrase- |
| 100X | 10.61 | 11.44 | 10.6 | 11.6 | 11.6 | 2.1 |
| 10X | 7 | 6.16 | 5.7 | 8.67 | 6.63 | 2.4 |
| 1X | 4.37 | 4.8 | n.d. | 7.09 | 4.6 | n.d. |

D17 cells have been transduced at different MOIs with EIAV vectors. The dCT values represent the ratio of β-actin/EIAV genomes in 100 ng of total DNA (dCt = βactin Ct-CMVp Ct). The PCR reaction amplifies the CMV promoter region present in the integrated EIAV genome. The dCT values of untransduced cells was ~1.85. Similar results are obtained using the EIAV packaging signal.

The invention can be further described by the following numbered paragraphs:

1. A retroviral vector genome comprising two or more NOIs operably linked by one or more Internal Ribosome Entry Site(s).

2. A retroviral vector genome comprising three or more NOIs operably linked by two or more Internal Ribosome Entry Site(s).

3. A genome according to claim 1, wherein each NOI is useful in the treatment of a neurodegenerative disorder.

4. A genome according to any preceding claim, which is a lentiviral vector genome.

5. A lentiviral vector genome comprising two or more NOIs suitable for treating a neurodegenerative disorder.

6. A genome according to claim 5, comprising three or more NOIs suitable for treating a neurodegenerative disorder.

7. A genome according to claim 5, in which the NOIs are operably linked by one or more Internal Ribosome Entry Sites(s).

8. A genome according to any preceding claim, wherein the NOIs encode a protein selected from the following group: Tyrosine Hydroxylase, GTP-cyclohydrolase I, Aromatic Amino Acid Dopa Decarboxylase and Vesicular Monoamine Transporter 2.

9. A genome according to claim 8, wherein the NOIs encode Tyrosine Hydroxylase, GTP-cyclohydrolase I and optionally Aromatic Amino Acid Dopa Decarboxylase or Aromatic Amino Acid Dopa Decarboxylase and Vesicular Monoamine Transporter 2.

10. A lentiviral vector genome encoding tyrosine hydroxylase and GTP-cyclohydrolase I.

11. A lentiviral vector genome according to claim 10, which also encodes Aromatic Amino Acid Dopa Decarboxylase and/or Vesicular Monoamine Trasporter 2.

12. A genome according to claim 10 or 11 which comprises two or more NOIs operably linked by one or more Internal Ribosome Entry sites.

13. A genome according to any preceding claim which is derivable from HIV.

14. A genome according to any of claims 1 to 12 which is derivable from EIAV.

15. A genome according to any of claims 4 to 14, wherein the lentiviral vector is a non-primate lentiviral vector.

16. A genome according to any preceding claim wherein at least one of the NOIs is operably linked to a promoter or promoter element(s).

17. A genome according to any of claims 4 to 16, which lacks the rev responsive element.

18. A genome according to any of claims 4 to 17, which comprises a cPPT sequence.

19. A genome according to any of claims 4 to 18, which comprises a post-transcriptional regulatory element or a translational enhancer.

20. A vector system comprising a gename according to any preceding claim.

21. A vector system according to claim 20, comprising
(i) a genome according to any of claims 4 to 19;
(ii) a nucleotide sequence coding for lentiviral gag and pol proteins;
(iii) nucleotide sequences encoding other essential viral packaging components not encoded by the nucleotide sequence of ii).

22. A lentiviral vector system which is capable of delivering an RNA genome to a recipient cell, wherein the genome is longer than the wild type genome of the lentivirus.

23. A lentiviral vector system according to claim 22, which is an EIAV vector system.

24. A vector system according to any of claims 20 to 23, which is devoid of any functional additional genes.

25. A vector system according to any of claims 20 to 24, which is pseudotyped with at least part of a heterologous env protein.

26. A vector system according to claim 25, in which the heterologous env protein is derivable from Rabies-G or VSV G.

27. A vector genome according to any of claims 1 to 19 or a system according to any of claims 20 to 26 for use in a method of producing lentiviral particles.

28. A method for producing a lentiviral particle which method comprises introducing into a producer cell:
i) a genome as defined in any one of claims 4 to 19,
ii) a nucleotide sequence coding for lentiviral gag and pot proteins; and
iii) nucleotide sequences encoding other essential viral packaging components not encoded by one or more of the nucleotide sequences of ii).

29. A method according to claim 28, wherein the nucleotide sequence coding for gag and pol is codon optimised for expression in the producer cell.

30. A viral particle produced by the system of any one of claims 20 to 26 or by the method of claim 28 or 29.

31. A pharmaceutical composition comprising the genome of any one of claims 1 to 19, the system of any one of claims 20 to 26 or the viral particle of claim 30, together with a pharmaceutically acceptable carrier or diluent.

32. Use of a genome as defined in any one of claims 1 to 19, a system of any one of claims 20 to 26 or a viral particle of claim 30, in the manufacture of a pharmaceutical composition to treat and/or prevent a disease in a subject.

33. A method of treating and/or preventing a disease in a subject in need of same, said method comprising the step of using a of a genome as defined in any one of claims 1 to 19, a system of any one of claims 20 to 26 or a viral particle of claim 30.

34. A method according to claim 33, to treat and/or prevent a neurodegenerative disease.

35. A method according to claim 34, to treat and/or prevent Parkinson's disease.

36. A cell which has been transduced with a system according to any of claims 20 to 26.

37. A method of treating Parkinson's disease in a mammalian subject in need of same, which comprises the step of transplanting a cell according to claim 36 into the brain of the subject.

38. A bicistronic cassette comprising a nucleotide sequence which encodes tyrosine hydroxylase and a nucleotide sequence which encodes GTP-cyclohydrolase I operably linked by one or more IRES(s).

39. A bicistronic cassette comprising a nucleotide sequence which encodes Aromatic Amino Acid Dopa Decarboxylase and a nucleotide sequence which encodes Vesicular Monoamine Transporter 2 operably linked by one or more IRES(s).

40. A tricistronic cassette comprising a nucleotide sequence which encodes tyrosine hydroxylase, a nucleotide sequence which encodes GTP-cyclohydrolase I and a nucleotide sequence which encodes Aromatic Amino Acid Dopa Decarboxylase operably linked by two or more IRES(s).

We claim:

1. A lentiviral vector genome comprising three nucleotides of interest (NOIs) operably linked by one or more Internal Ribosome Entry Site(s) (IRES), wherein the NOIs encode tyrosine hydroxylase (TH), GTP-cyclohydrolase I (GTP-CH1) and aromatic amino acid dopa decarboxylase (AADC).

2. The genome according to claim 1, wherein the lentiviral vector genome is an HIV lentiviral vector genome.

3. The genome according to claim 1, wherein the lentiviral vector genome is a non-primate lentiviral vector genome.

4. The genome according to claim 1, wherein at least one of the NOIs is operably linked to a promoter or promoter element(s).

5. The genome according to claim 1, which lacks the rev responsive element (RRE).

6. The genome according to claim 1, further comprising a cPPT sequence.

7. The genome according to claim 1, further comprising a post-transcriptional regulatory element or a translational enhancer.

8. The genome according to claim 1, wherein at least one of the NOIs is codon optimized.

9. The genome according to claim 3, wherein the non-primate lentiviral vector genome is an EIAV lentiviral vector genome.

10. A vector system comprising a lentiviral vector genome comprising two or more nucleotides of interest (NOIs) operably linked by one or more Internal Ribosome Entry Site(s) (IRES), wherein the vector system further comprises: (i) a nucleotide sequence coding for lentiviral gag and pol proteins; and (ii) nucleotide sequence(s) encoding an env protein, and wherein the lentiviral vector genome is longer than the lentivirus wild type genome.

11. The vector system according to claim 10, which is an EIAV vector system.

12. The vector system according to claim 10, which is devoid of any additional lentiviral functional genes other than the nucleotides encoding lentiviral gag and pol proteins.

13. The vector system according to claim 10, which is pseudotyped with at least part of a heterologous env protein.

14. The vector system according to claim 10, wherein the lentiviral vector genome comprises a packaging signal.

15. A method for producing a lentiviral particle comprising introducing into a producer cell the vector system of claim 10, thereby producing a lentiviral particle.

16. The vector system according to claim 13, in which the heterologous env protein is Rabies-G or VSV G.

17. The method according to claim 15, wherein the nucleotide sequence coding for lentiviral gag and pol is codon optimized for expression in the producer cell.

18. The method according to claim 15, wherein the lentiviral vector genome comprises a packaging signal.

19. A lentiviral particle produced by the method of claim 15, wherein the particle comprises the two or more NOIs, operably linked by one or more IRES(s).

20. A cell in vitro which has been transduced with the lentiviral particle of claim 19.

21. A tricistronic cassette comprising a nucleotide sequence which encodes TH, a nucleotide sequence which encodes GTP-CH1, and a nucleotide sequence which encodes AADC, operably linked to two or more IRES(s).

22. The tricistronic cassette of claim 21, wherein at least one of the nucleotides sequences is codon optimized.

23. The cassette of claim 21, wherein the IRES is a viral IRES.

24. The cassette of claim 21, wherein the IRES is a cellular IRES.

25. The cassette of claim 23, wherein the viral IRES is from a picornavirus.

26. The cassette of claim 25, wherein the picornavirus is encephalomyocarditis virus (EMCV) or poliovirus (PV).

27. The cassette of claim 24, wherein the cellular IRES is FGF2 IRES or NRF IRES.

28. A lentiviral vector genome comprising three or more NOIs operably linked by two or more Internal Ribosome Entry Sites (IRESs), wherein each NOI encodes a protein associated with a neurodegenerative disorder.

29. The genome according to claim 28, wherein the lentiviral vector genome is an HIV lentiviral vector genome.

30. The genome according to claim 28, wherein the lentviral vector genome is a non-primate lentiviral vector genome.

31. The genome according to claim 28, wherein each NOI encodes a protein selected from the group consisting of TH, GTP-CH1, AADC, and VMAT2.

32. The genome according to claim 28, wherein at least one of the NOIs is operably linked to a promoter or promoter element(s).

33. The genome according to claim 28, which lacks the rev responsive element (RRE).

34. The genome according to claim 28, further comprising a cPPT sequence.

35. The genome according to claim 28, further comprising a post-transcriptional regulatory element or a translational enhancer.

36. The genome according to claim 28, wherein the NOIs encode TH, GTP-CH1 and AADC.

37. The genome according to claim 28, wherein the genome is a self-inactivating genome.

38. A vector system comprising the genome according to claim 28, wherein the vector system further comprises (i) a nucleotide sequence coding for lentiviral gag and pol proteins; and (ii) nucleotide sequence(s) coding for an env protein.

39. The genome according to claim 30, wherein the non-primate lentiviral vector genome is an EIAV lentiviral vector genome.

40. The genome according to claim 31, wherein at least one of the NOIs is codon optimized.

41. A vector system comprising the genome according to claim 37.

42. The vector system according to claim 38, wherein the lentiviral vector genome is longer than the lentivirus wild type genome.

43. The vector system of claim 38, which is an EIAV vector system.

44. The vector system according to claim 38, which is devoid of any additional lentiviral functional genes other than the nucleotide sequence coding for lentiviral gag and pol proteins.

45. The vector system according to claim 38, which is pseudotyped with at least part of a heterologous env protein.

46. The vector system according to claim 38, wherein the genome comprises a packaging signal.

47. A method for producing a lentiviral particle comprising introducing into a producer cell the vector system of claim 38, thereby producing a lentiviral particle.

48. The vector system according to claim 45, in which the heterologous env protein is Rabies-G or VSV G.

49. The method according to claim 47, wherein the nucleotide sequence coding for lentiviral gag and pol is codon optimized for expression in the producer cell.

50. The method according to claim 47, wherein the genome comprises a packaging signal.

51. A lentiviral particle produced by the method of claim 47, which comprises the three or more NOIs, operably linked by two or more IRESs, wherein each NOI encodes a protein associated with a neurodegenerative disorder.

52. A cell in vitro which has been transduced with the lentiviral particle according to claim 51.

* * * * *

UNITED STATES PATENT AND TRADEMARK OFFICE
CERTIFICATE OF CORRECTION

| | | |
|---|---|---|
| PATENT NO. | : 7,259,015 B2 | Page 1 of 2 |
| APPLICATION NO. | : 10/408456 | |
| DATED | : August 21, 2007 | |
| INVENTOR(S) | : Alan John Kingsman et al. | |

It is certified that error appears in the above-identified patent and that said Letters Patent is hereby corrected as shown below:

On the Title Page Item (75) should read

ON THE FACE OF THE PATENT

Inventors: Alan John Kingsman, "The Oxford Science Park (GB)" --Oxford, United Kingdom--;

Nicholas D. Mazarakis, "The Oxford Science Park (GB)" -- Oxford, United Kingdom--;

Enca Martin-Rendon, "Sanford-on-Thames (GB)" --Oxfordshire, United Kingdom--;

Mimoun Azzouz, "The Oxford Science Park (GB)" --Sheffield, United Kingdom--

Jonathan Rohll, "The Oxford Science Park (GB)" --Oxford, United Kingdom--

UNITED STATES PATENT AND TRADEMARK OFFICE
CERTIFICATE OF CORRECTION

PATENT NO. : 7,259,015 B2
APPLICATION NO. : 10/408456
DATED : August 21, 2007
INVENTOR(S) : Alan John Kingsman et al.

It is certified that error appears in the above-identified patent and that said Letters Patent is hereby corrected as shown below:

Column 122, line 2 should read

22. The tricistronic cassette of claim 21, wherein at least one of the "nucleotides" --nucleotide-- sequences is codon optimized.

Signed and Sealed this

Eighteenth Day of December, 2007

JON W. DUDAS
*Director of the United States Patent and Trademark Office*